(12) United States Patent
Hayakawa et al.

(10) Patent No.: US 9,617,135 B2
(45) Date of Patent: Apr. 11, 2017

(54) BEVERAGE FILLING METHOD AND APPARATUS

(71) Applicant: DAI NIPPON PRINTING CO., LTD., Tokyo (JP)

(72) Inventors: Atsushi Hayakawa, Shinjuku-ku (JP); Takaharu Hirooka, Shinjuku-ku (JP); Takaki Maekawa, Shinjuku-ku (JP); Hitoshi Takaku, Shinjuku-ku (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 499 days.

(21) Appl. No.: 14/143,637

(22) Filed: Dec. 30, 2013

(65) Prior Publication Data
US 2014/0109520 A1    Apr. 24, 2014

Related U.S. Application Data

(62) Division of application No. 12/993,727, filed as application No. PCT/JP2009/059183 on May 19, 2009, now Pat. No. 9,108,835.

(30) Foreign Application Priority Data

May 20, 2008  (JP) .................................. 2008-131978
Dec. 26, 2008  (JP) .................................. 2008-334563
(Continued)

(51) Int. Cl.
*B65B 55/04*    (2006.01)
*B67C 3/24*     (2006.01)
(Continued)

(52) U.S. Cl.
CPC ............ *B67C 3/242* (2013.01); *B67C 7/0073* (2013.01); *B65B 3/022* (2013.01); *B65B 55/10* (2013.01);
(Continued)

(58) Field of Classification Search
CPC . B67C 1/242; B67C 7/0073; B67C 2003/227; B65B 3/002; B65B 55/10; B65B 55/103
(Continued)

(56) References Cited

U.S. PATENT DOCUMENTS 5,591,462 A    1/1997  Darling et al.
5,844,677 A    12/1998  Dimmick, Sr. et al.
(Continued)

FOREIGN PATENT DOCUMENTS

DE        4427870 A1    2/1996
DE    102005012507 A1    9/2006
(Continued)

OTHER PUBLICATIONS

"Stability of Packaging Line System/Equipment," Beverage Japan No. 187, issued on Jul. 10, 1997.
(Continued)

*Primary Examiner* — Sameh Tawfik
(74) *Attorney, Agent, or Firm* — Sughrue Mion, PLLC

(57) ABSTRACT

Only a bottle properly preliminarily heated is sterilized by hydrogen peroxide. Temperature inspection to the bottle is performed while travelling the bottle. During the inspection, a bottle of which temperature does not reach a predetermined temperature is removed and a bottle of which temperature reaches the predetermined temperature is continuously traveled, hydrogen peroxide condensed mist α is blown toward a mouth portion 1a of the bottle by a spray tube 59 disposed at a predetermined position, and hot air is blown into the bottle from the nozzle while the nozzle 64 following the mouth portion of the bottle. According to such operation, only the bottle properly heated can be sterilized by the hydrogen peroxide, Thereafter, beverage fills the bottle, which is then sealed.

12 Claims, 31 Drawing Sheets

(30) Foreign Application Priority Data

| | | | |
|---|---|---|---|
| Feb. 6, 2009 | (JP) | ................................ | 2009-026035 |
| Feb. 6, 2009 | (JP) | ................................ | 2009-026036 |
| Feb. 17, 2009 | (JP) | ................................ | 2009-033813 |

(51) Int. Cl.
  *B67C 7/00* (2006.01)
  *B65B 55/10* (2006.01)
  *B65B 3/02* (2006.01)
  *B67C 3/22* (2006.01)

(52) U.S. Cl.
  CPC ....... *B65B 55/103* (2013.01); *B67C 2003/227* (2013.01)

(58) Field of Classification Search
  USPC ......................................................... 53/426
  See application file for complete search history.

(56) References Cited

U.S. PATENT DOCUMENTS

| | | | |
|---|---|---|---|
| 6,984,360 B1* | 1/2006 | Feuilloley | A61L 2/208 |
| | | | 141/6 |
| 7,360,345 B2 | 4/2008 | Topf | |
| 7,707,807 B2 | 5/2010 | Py | |
| 7,739,859 B2 | 6/2010 | Colato et al. | |
| 7,900,422 B2 | 3/2011 | Fischer | |
| 7,905,257 B2 | 3/2011 | Py | |
| 9,302,421 B2* | 4/2016 | Wilson | B29C 49/4273 |
| 2001/0010145 A1 | 8/2001 | Tawa et al. | |
| 2002/0159915 A1* | 10/2002 | Zelina | A61L 2/186 |
| | | | 422/3 |
| 2004/0208781 A1 | 10/2004 | Hayashi et al. | |
| 2009/0147082 A1 | 6/2009 | Detrois et al. | |
| 2010/0170867 A1 | 7/2010 | Hayakawa | |

FOREIGN PATENT DOCUMENTS

| | | |
|---|---|---|
| DE | 102006034432 A1 | 1/2008 |
| JP | 3-226444 A | 10/1991 |
| JP | 08-244730 A | 9/1996 |
| JP | 09-328113 A | 12/1997 |
| JP | 11-291331 A | 10/1999 |
| JP | 2001-301721 A | 10/2001 |
| JP | 2001-525542 A | 12/2001 |
| JP | 2003-004648 A | 1/2003 |
| JP | 2006-103803 A | 4/2006 |
| JP | 2006-111295 A | 4/2006 |
| JP | 2007-113923 A | 5/2007 |
| JP | 2008-074438 A | 4/2008 |
| JP | 2008-83005 A | 4/2008 |
| JP | 2008-532866 A | 8/2008 |
| JP | 2008-222428 A | 9/2008 |
| JP | 2010-155631 A | 7/2010 |
| WO | 2006/097796 A2 | 9/2006 |
| WO | 2007/031194 A1 | 3/2007 |
| WO | 2007/132341 A2 | 11/2007 |
| WO | 2007/134803 A2 | 11/2007 |

OTHER PUBLICATIONS

Extended European Search Report dated Aug. 19, 2013 issued in EP Patent Application No. 13177836.
Extended European Search Report dated Aug. 20, 2013 issued in EP Patent Application No. 13177846.6-1707.
Extended European Search Report dated Aug. 19, 2013 issued in EP Patent Application No. 13177853.2-1707.
Extended European Search Report dated Aug. 21, 2013 issued in EP Patent Application No. 13177861.5-1707.
Extended European Search Report dated Aug. 21, 2013 issued in EP Patent Application No. 13177873.0-1707.

* cited by examiner supply preform mount preform to mandrel heat preform blow molding invert bottle upside-down return bottle to normal state inspect bottle shell portion inspect bottle temperature inspect support ring inspect bottle neck upper face inspect bottle bottom portion directly spray hydrogen peroxide air-rinse beverage filling air-rinse hot water rinse

BEVERAGE FILLING METHOD AND APPARATUS

CROSS REFERENCE TO RELATED APPLICATIONS

This is a Divisional of U.S. application Ser. No. 12/993,727 filed Nov. 19, 2010, which is a National Stage Entry of International Application No. PCT/JP2009/059183 filed May 19, 2009, which claims priority from Japanese Patent Application No. 2008-131978 filed May 20, 2008, Japanese Patent Application No. 2008-334563 filed Dec. 26, 2008, Japanese Patent Application No. 2009-026035 filed Feb. 6, 2009, Japanese Patent Application No. 2009-026036 filed Feb. 6, 2009, and finally Japanese Patent Application No. 2009-033813 filed Feb. 17, 2009, the contents of all of which are incorporated herein by reference in their entirety.

TECHNICAL FIELD

The present invention relates to a beverage filling method for continuously performing processes from bottle molding to beverage filling through bottle sterilization by hydrogen peroxide, and also relates to a beverage filling apparatus.

BACKGROUND ART

As a conventional beverage filling apparatus, there is known an apparatus provided with a molding section for molding a bottle from a preform by means of blow molding, a sterilization section for sterilizing the bottle molded in the molding section by mist of hydrogen peroxide, air-rinse section for performing air-rinse treatment to the bottle sterilized in the sterilization section, and a filling section for filling, with beverage, the bottle subjected to the air-rinse treatment in the air-rinse section and then sealing the bottle, these sections being continuously coupled.

The apparatus is also provided with drive means for continuously traveling the bottle from the molding section to the filling section through the sterilization section and the air-rinse section, and a portion extending from the molding section to the filling section is covered by a chamber. According to the beverage filling apparatus mentioned above, the sterilization effect to the bottle by the mist of the hydrogen peroxide generated by utilizing heat added in the bottle molding process (for example, refer to Patent Publication 1).

In addition, there is also known an apparatus in which a bottle molding section and a beverage filling section are coupled and covered by a clean room, and a sterilization section is eliminated by supplying a preform in an aseptic state to the molding section (for example, refer to Patent Publication 2).

Patent Literature 1: Japanese Patent Laid-open Publication No. 2006-111295
Patent Literature 2: Japanese Patent Laid-open HEI 11-291331.

DISCLOSURE OF THE INVENTION

Problems to be Solved by the Invention

The conventional beverage filling apparatus involve the following problems.

(1) A process or treatment from the bottle molding process to the beverage filling process through the bottle sterilization process by the hydrogen peroxide can be continuously performed. However, since all the molded bottles are fed to the sterilization process and the filling process, there is a fear that beverage may fill even defective bottles, which may be then delivered. For example, in a case where the bottles heated to an insufficient temperature are fed to the sterilization process, the sterilization may be incompletely performed, and such defective bottles are filled with the beverage and then delivered. In addition, there is also a fear that damaged bottles filled with the beverage may be delivered.

(2) At a time when the bottles are sterilized and filled with beverage while conveying the bottles, shell portions of the bottles may be contacted to each other, and because of this reason, the hydrogen peroxide may insufficiently adhere to the shell portions of the bottles, which results in defective sterilization of the bottles or damage may be caused to the bottles.

(3) In the conventional beverage filling apparatus, the bottle traveling means is constructed by train or row of wheels and/or turntables, and for example, if any trouble is caused to the bottle molding section, all the wheels and the turntables in the beverage filling apparatus are stopped. However, if all the wheels and the turntables are stopped in operations, normally molded bottles stay in the sterilization section, so that the hydrogen peroxide excessively adheres to the bottles, which may produce defective bottles. Therefore, if the traveling means is stopped by any trouble, all the bottles including normal and defective ones in the beverage filling apparatus will have to be disposed of, thus providing a problem.

(4) In the conventional beverage filling apparatus, since the bottle passes in front of a nozzle through which the hydrogen peroxide mist is ejected, there may cause a case where the mist does not spread to every corner portion of the bottle. Particularly, the mist hardly adheres to the bottom portion inside the bottle and insufficient sterilization may be performed to this portion. In order to obviate such defect, in the conventional technology, a plurality of nozzles is arranged along the bottle conveying path to eject a large amount of mists. In such technology, however, a large volume of hydrogen peroxide may be consumed, thus providing a problem.

In addition, in a case where the travelling speed for feeding the bottles is increased for increasing production efficiency of aseptic packages, it becomes necessary to increase flow rate of the mist, which will result in further increasing of the consumption of the hydrogen peroxide. Although this problem may be considered to be solved by blowing the mist into the bottle while following the nozzle to the bottle, if the nozzle ejecting the mist is moved, the mist is liable to be condensed during the flowing from a mist generating device to the nozzle, and the condensed hydrogen peroxide may drop on the bottle, thus also providing a problem.

Although the condensation may not occur by lowering the concentration of the hydrogen peroxide, in such case, the sterilization effect may be degraded, thus also providing a problem.

(5) In order to enhance the bottle sterilization effect by applying the hydrogen peroxide mist, it may be desirable to preheat the bottle. However, according to a mold for molding the bottle, there may cause a case where the bottle bottom portion is excessively cooled, and in such occasion, insufficiently sterilized bottles may be produced. Such phenomenon is not limited to a case of utilizing a remaining heat in the molding process and may be caused in a case where hot air is blown to a pre-molded bottle, or a bottle is preliminarily heated by approaching a heater to the bottle.

(6) In the conventional beverage filling apparatus, mist of a sterilization agent such as hydrogen peroxide is ejected toward the bottle. However, in such technology, the mist adheres to various components or parts of the beverage filling apparatus and hence corrodes and damages them, thus providing a problem.

(7) In the conventional beverage filling apparatus, although the sterilization performance is enhanced by, for example, utilizing remaining heat in the bottle molding process, heat is easily removed in contact to a guide or like members of the wheel during the bottle conveyance, which may deteriorate the sterilization performance.

Therefore, an object of the present invention is to provide a beverage filling method and apparatus capable of solving the problems encountered in the conventional art mentioned above.

Means for Solving the Problems

In order to solve the above problems, the present invention adopts the following structures.

Further, although the followings are described with reference numerals on the drawings, the present invention is not limited thereto.

In one exemplary embodiment, a beverage filling method includes: forming a bottle (1) from a heated preform (6) through a blow molding process; inspecting the bottle (1) after the molding; blowing hydrogen peroxide mist ($\alpha$) or gas ($\beta$) to the bottle (1) within a time in which heat applied to the preform (6) remains after the inspection; and filling the bottle (1) with beverage (a) and sealing the bottle.

In another aspect of a preferred embodiment, it may be possible that the bottle (1) is subjected to an air rinse treatment after the blowing of the hydrogen peroxide mist ($\alpha$) or gas ($\beta$) to the bottle (1), and the bottle (1) is then filled with the beverage (a) and sealed.

In another aspect of a preferred embodiment, it may be possible that the bottle (1) is subjected to a rinse treatment with heated aseptic water after the blowing of the hydrogen peroxide mist or gas into the bottle, and the bottle is then filled with the beverage and sealed.

In another aspect of a preferred embodiment, it may be possible that the bottle (1) is subjected to a rinse treatment with aseptic water after an air rinse treatment, and the bottle (1) is then filled with the beverage (a) and sealed.

In another aspect of a preferred embodiment, it may be possible that the bottle (1) is subjected to a rinse treatment with aseptic water after the air rinse treatment with aseptic air ($\gamma$) containing hydrogen peroxide gas ($\beta$), and the bottle (1) is then filled with the beverage (a) and sealed.

In another aspect of a preferred embodiment, it may be desired that a travelling path is provided so that the molded bottle (1) is continuously travelled to a section at which the sealing of the bottle is performed, the travelling path being formed from a wheel row (36a and like) around which grippers (28 and like) are arranged, and the bottle (1) is transferred from an upstream side wheel to a downstream side wheel in a state that a neck portion (1a) of the bottle (1) is grasped by the gripper (28 and like) around the respective wheels (36a and like) while revolving.

In another aspect of a preferred embodiment, it may be desired that all the steps of molding the bottle (1) from the heated preform (6) through the blow molding process to the beverage filling and bottle sealing process is performed while continuously travelling the bottle (1), after the molding process and before the sterilization process, a temperature of the bottle (1) to which heat at the preform heating process remains is inspected, a bottle (1) of which temperature does not reach a predetermined temperature is removed, and only a bottle (1) of which temperature reaches the predetermined temperature is sterilized and filled with the beverage.

In another aspect of a preferred embodiment, it may be possible that the inspection process is performed by inspecting the bottle temperature and imaging a shell portion of the bottle (1).

In another aspect of a preferred embodiment, it may be possible that the inspection process is performed by inspecting the bottle temperature and imaging a bottom portion of the bottle (1).

In another aspect of a preferred embodiment, it may be possible that the inspection process is performed by inspecting the bottle temperature and imaging a top face of a neck portion of the bottle (1).

In another aspect of a preferred embodiment, it may be possible that the inspection process is performed by inspecting the bottle temperature and imaging a support ring of a neck portion of the bottle (1).

Furthermore, an aspect of a preferred embodiment can provide a beverage filling apparatus comprising: a molding section (7) for molding a bottle (1) from a heated preform (6) through a blow molding process; a sterilization section (9) for sterilizing the bottle (1) molded in the molding section (7) with hydrogen peroxide mist ($\alpha$) or hydrogen peroxide gas ($\beta$); and a filling section (10) for filling the bottle (1) sterilized in the sterilization section (9) with beverage (a) and then sealing the bottle (1), in which the molding section, the sterilization section and the filling section are coupled with each other, bottle travelling means is disposed for continuously travelling the bottle (1) on a travelling path from the molding section (7) to the filling section (10) through the sterilization section (9), and a portion from the sterilization section (9) to the filling section (10) is covered by a chamber, wherein an inspection section (8) for performing a predetermined inspection to the bottle (1) molded in the molding section (7) is disposed between the molding section (7) and the sterilization section (9) so as to be coupled therewith, the inspection section (8) including discharging means (53a and like) for discharging, from the bottle travelling path, a bottle judged as a defective bottle by the inspection, and positive pressure creating means (84 and like) for creating positive pressure in the inspection section (8) more than pressures in the molding section (7) and the sterilization section (9), and wherein the travelling means is provided with wheels (19a and like) disposed in a row from the molding section (7) toward the filling section (10) and a gripper (28 and like) turning around the wheels (19a and like) while gripping the bottle neck portion (1a) and transferring the bottle (1) from an upstream side wheel to a downstream side wheel, the gripper being controlled in a travelling speed such that a heat applied to the preform (6) and remaining to the bottle (1) is maintained to a temperature necessary for the sterilization of the bottle in the bottle sterilization section (9).

In another aspect of a preferred embodiment, it may be possible that an air rinse section (96) for air-rinsing, with aseptic air ($\gamma$), the bottle sterilized in the sterilization section (9) is further disposed between the sterilization section (9) and the filling section (10).

In another aspect of a preferred embodiment, it may be possible that an aseptic water rinse section (91) for rinsing, with heated aseptic water, the bottle (1) sterilized in the sterilization section (9) is further disposed between the sterilization section (9) and the filling section (10).

In another aspect of a preferred embodiment, it may be possible that an aseptic water rinse section (91) is disposed between the air rinse section (96) and the filling section (10).

In another aspect of a preferred embodiment, it may be possible that air (γ) containing hydrogen peroxide gas (β) is blown against the bottle (1) in the air rinse section (96).

In another aspect of a preferred embodiment, it may be possible that the wheels (36 and like) are sectioned into a desired number of rows, each of which is driven by an independent servo-motor (S1 and like).

In another aspect of a preferred embodiment, it may be possible that the inspection section (8) is provided with temperature inspection means (46 and like) for detecting a temperature of the bottle (1) and judging quality of the bottle (1).

In another aspect of a preferred embodiment, it may be possible that the gripper (28 and like) travelling in the inspection section (8) is effected with matte surface treatment.

In another aspect of a preferred embodiment, it may be possible that gripper interference prevention means (42 and like) is provided for preventing interference between grippers (28 and 37) at a time of stopping one of the molding section side wheel (19b) and the inspection section side wheel (36a) adjacent to the molding section side wheel (19b).

In another aspect of a preferred embodiment, it may be possible that an atmosphere shutoff chamber (79) is disposed between a chamber (8a) of the inspection section (8) and a chamber (9a) of the sterilization section (9), clean air is supplied into the chamber (8a) of the inspection section (8) by air supply means, and air is discharged from the atmosphere shutoff chamber (79) by discharge means.

In another aspect of a preferred embodiment, it may be possible that the discharge means, for discharging outside the hydrogen peroxide mist or gas from the chamber (9a) of the sterilization section (9), is disposed at a portion at which the chamber (9a) of the sterilization section (9) contacts the atmosphere shutoff chamber (79).

In another aspect of a preferred embodiment, it may be possible that an air nozzle (90) forming an air curtain is disposed at a portion at which the chamber (9a) of the sterilization section (9) contacts the atmosphere shutoff chamber (79).

Effects of the Invention

In an aspect of a preferred embodiment, there is provided a beverage filling method comprising the steps of: forming a bottle (1) from a heated preform (6) through a blow molding process; inspecting the bottle (1) after the molding; blowing hydrogen peroxide mist (α) or gas (β) to the bottle (1) within a time in which heat applied to the preform (6) remains after the inspection; and filling the bottle (1) with beverage (a) and sealing the bottle. Accordingly, the beverage (a) can fill only the bottle (1) which was inspected and judged to be normally molded, and hence, proper beverage packaging can be provided to a market.

In addition, since the hydrogen mist or gas is blown to the bottle (1) in a time when heat applied to the preform (6) remains, the bottle (1) can be sterilized by a small amount of the hydrogen peroxide. In the case of a PET bottle, although adsorbing amount of the hydrogen peroxide to the bottle wall increases, such adsorption can be prevented. That is, according to experiment of the inventors, the density of the hydrogen peroxide condensed to the surface of the bottle (1) becomes high as high as the temperature of the bottle (1) because of the fact that the boiling point of the hydrogen peroxide is higher than that of water. More specifically, in the case of the bottle temperatures of 50 degrees, 65 degrees, 80 degrees, the density of the hydrogen peroxide adhering to the surface of the bottle is each approximately 70 weight %, 80 weight %, 90 weight %. Since the density of the hydrogen peroxide adhering to the surface of bacteria increases in addition to high temperature, the bottle (1) can be sterilized by the small amount of the hydrogen peroxide.

In another aspect of a preferred embodiment, in the case the bottle (1) is subjected to an air rinse treatment after the blowing of the hydrogen peroxide mist (α) or gas (β) to the bottle (1), and the bottle (1) is then filled with the beverage (a) and sealed, even if the bottle (1) is of PET bottle, the remaining hydrogen peroxide can be properly removed from the bottle (1), and the following aseptic water rinsing treatment, which requires a large amount of water and large scale of equipment, can be eliminated.

In another aspect of a preferred embodiment, in the case that the bottle (1) is subjected to a rinse treatment with heated aseptic water after the blowing of the hydrogen peroxide mist or gas into the bottle, and the bottle is then filled with the beverage and sealed, aspergillus spore such as ascomycontina relatively weak to heat can be sterilized by the aseptic hot water. Thus, beverage which is liable to be corrupted by the aspergillus spore can fill the bottle, which is then stored.

In another aspect of a preferred embodiment, in the case that the bottle (1) is subjected to a rinse treatment with aseptic water after an air rinse treatment, and the bottle (1) is then filled with the beverage (a) and sealed, the hydrogen peroxide remaining in the bottle (1) can be further reduced.

In another aspect of a preferred embodiment, in the case that the bottle (1) is subjected to a rinse treatment with aseptic water after the air rinse treatment with aseptic air (γ) containing hydrogen peroxide gas (β), and the bottle (1) is then filled with the beverage (a) and sealed, the sterilization effect to the bottle (1) can be further improved, and the hydrogen peroxide remaining in the bottle (1) can be further reduced.

In another aspect of a preferred embodiment, in the case that a travelling path is provided so that the molded bottle (1) is continuously travelled to a section at which the sealing of the bottle is performed, the travelling path being formed from a wheel row (36a and like) around which grippers (28 and like) are arranged, and the bottle (1) is transferred from an upstream side wheel to a downstream side wheel in a state that a neck portion (1a) of the bottle (1) is grasped by the gripper (28 and like) around the respective wheels (36a and like) while revolving, the bottle (1) can be smoothly and effectively sterilized by the hydrogen peroxide within a time when the remaining heat at the time of heating the preform (6) is not cooled even if the inspection process is interposed. In addition, the bottle (1) can be fast conveyed into the air rinse section (96) in a time of the hydrogen peroxide not adhering to the bottle wall and the hydrogen peroxide can be prevented from remaining in the bottle (1).

In another aspect of a preferred embodiment, in the case that all the steps of molding the bottle (1) from the heated preform (6) through the blow molding process to the beverage filling and bottle sealing process is performed while continuously travelling the bottle (1), after the molding process and before the sterilization process, a temperature of the bottle (1) to which heat at the preform heating process remains is inspected, a bottle (1) of which temperature does not reach a predetermined temperature is removed, and only a bottle (1) of which temperature reaches the predetermined temperature is sterilized and filled with the beverage, only the bottle (1) of which temperature reaches to the predetermined temperature can contact the hydrogen peroxide mist α or gas β. Accordingly, the bottle can be promptly and surely sterilized, and in addition, the using amount of the hydrogen peroxide can be reduced. Even if the bottle (1) is made of PET, which is liable to easily adsorb the hydrogen peroxide, the remaining of the hydrogen peroxide can be reduced.

In another aspect of a preferred embodiment, in the case that the inspection process is performed by inspecting the bottle temperature and imaging a shell portion of the bottle (1), the beverage (a) can fill only the bottle (1) which is properly molded.

In another aspect of a preferred embodiment, in the case that the inspection process is performed by inspecting the bottle temperature and imaging a bottom portion of the bottle (1), the beverage (a) can fill only the bottle (1) which is properly molded.

In another aspect of a preferred embodiment, in the case that the inspection process is performed by inspecting the bottle temperature and imaging a top face of a neck portion of the bottle (1), the causing of defective sealing of the bottle (1) by the capping can be prevented.

In another aspect of a preferred embodiment, in the case that the inspection process is performed by inspecting the bottle temperature and imaging a support ring of a neck portion of the bottle (1), the beverage (a) can fill only the normal bottle (1) to which any burr or injury is formed.

In another aspect of a preferred embodiment, there is provided a beverage filling apparatus comprising: a molding section (7) for molding a bottle (1) from a heated preform (6) through a blow molding process; a sterilization section (9) for sterilizing the bottle (1) molded in the molding section (7) with hydrogen peroxide mist (α) or hydrogen peroxide gas (β); and a filling section (10) for filling the bottle (1) sterilized in the sterilization section (9) with beverage (a) and then sealing the bottle (1), in which the molding section, the sterilization section and the filling section are coupled with each other, bottle travelling means is disposed for continuously travelling the bottle (1) on a travelling path from the molding section (7) to the filling section (10) through the sterilization section (9), and a portion from the sterilization section (9) to the filling section (10) is covered by a chamber, wherein an inspection section (8) for performing a predetermined inspection to the bottle (1) molded in the molding section (7) is disposed between the molding section (7) and the sterilization section (9) so as to be coupled therewith, the inspection section (8) including discharging means (53a and like) for discharging, from the bottle travelling path, a bottle judged as a defective bottle by the inspection, and positive pressure creating means (84 and like) for creating positive pressure in the inspection section (8) more than pressures in the molding section (7) and the sterilization section (9), and wherein the travelling means is provided with wheels (19a and like) disposed in a row from the molding section (7) toward the filling section (10) and a gripper (28 and like) turning around the wheels (19a and like) while gripping the bottle neck portion (1a) and transferring the bottle (1) from an upstream side wheel to a downstream side wheel, the gripper being controlled in a travelling speed such that a heat applied to the preform (6) and remaining to the bottle (1) is maintained to a temperature necessary for the sterilization of the bottle in the bottle sterilization section (9).

Furthermore, the travelling means for conveying the bottle (1) to the filling section (10) from the molding section (7) is provided with wheels (19a and like) disposed in a row from the molding section (7) toward the filling section (10) and a gripper (28 and like) turning around the wheels (19a and like) while gripping the bottle neck portion (1a) and transferring the bottle (1) from an upstream side wheel to a downstream side wheel, the gripper being controlled in a travelling speed such that a heat applied to the preform (6) and remaining to the bottle (1) is maintained to a temperature necessary for the sterilization of the bottle in the bottle sterilization section (9), and accordingly, even in the interposing of the inspection section (8), the bottle (1) can be promptly fed to the sterilization section (9) so as not to cool the remaining heat at the heating time of the preform (6) and to suitably sterilize the bottle by the hydrogen peroxide. Thus, the beverage packaging properly sterilized can be provided to the market.

In addition, since the bottle (1) is conveyed by gripping the bottle neck portion (1a) by the gripper (28 and the like), the bottles (1) can be prevented from contacting to each other. This conveying system by using the gripper (28 and like) is lowered in bio-burden invading into the sterilization section (9) from the molding section (7) and the sterility assurance level (SAL) of the product can be improved in comparison with the conventional conveying system utilizing air. Furthermore, the deformation, injury, damage and the like can be prevented. Still furthermore, in the conventional system, it is required to change a screw or guide used for introducing the bottle into the filling section from the air conveying path at the time of changing the bottle size, shape and so on in conformity with the size of the bottle shell portion and shape, but according to the present invention, such working can be eliminated. Since the shape and size of the bottle neck portion is constant regardless of the shape and size of the bottle body, by adopting the bottle conveying system using the gripper, the screw, guide and like which are required to be disposed in the conventional system can be eliminated in location, and the exchanging working or like working can be also eliminated.

Furthermore, since the positive pressure creating means (84 and like) for creating the positive pressure in the inspection section (8) than in the molding section (7) and the sterilization section (8) is disposed, the invasion of the bacteria and the hydrogen peroxide into the inspection section (8) can be blocked, and hence, the inspection equipment or like can be protected from contamination by the bacteria or corrosion by the hydrogen peroxide.

In another aspect of a preferred embodiment, in the case that an air rinse section (96) for air-rinsing, with aseptic air (γ), the bottle sterilized in the sterilization section (9) is further disposed between the sterilization section (9) and the filling section (10), even if the bottle (1) is made of PET, the remaining hydrogen peroxide can be completely removed from the bottle (1) by the air rinsing treatment, thus preventing a large amount of water from consuming in the following process and also preventing an aseptic water rinsing treatment requiring a large equipment from installing.

In another aspect of a preferred embodiment, in the case that an aseptic water rinse section (91) for rinsing, with heated aseptic water, the bottle (1) sterilized in the sterilization section (9) is further disposed between the sterilization section (9) and the filling section (10), although it is relatively difficult to perform the sterilization by the hydrogen peroxide in the sterilization section (9), aspergillus spore such as ascomycontina relatively weak to heat can be sterilized by the heated aseptic water in the aseptic water rinse section (91). Thus, it is possible to fill the bottle (1) with beverage which is liable to become corrupted by the aspergillus sporee, which is then stored.

In another aspect of a preferred embodiment, in the case that an aseptic water rinse section (91) is disposed between the air rinse section (96) and the filling section (10), the hydrogen peroxide remaining in the bottle (1) can be further removed.

In another aspect of a preferred embodiment, in the case that air (γ) containing hydrogen peroxide gas (β) is blown against the bottle (1) in the air rinse section (96), the sterilization effect to the bottle (1) can be further improved and the hydrogen peroxide remaining in the bottle (1) can be further removed.

In another aspect of a preferred embodiment, in the case that the wheels (36 and like) are sectioned into a desired number of rows, each of which is driven by an independent servo-motor (S1 and like), since the wheels arranged in the inspection section (8), the sterilization section (9), the filling section (10) and so on are driven by independent servo-motors (S1 and like), respectively, the respective sections can be synchronously driven.

In another aspect of a preferred embodiment, in the case that the inspection section (8) is provided with temperature inspection means (46 and like) for detecting a temperature of the bottle (1) and judging quality of the bottle (1), it is possible to transfer the bottle (1) having a temperature capable of enhancing the sterilization effect to the sterilization section.

In another aspect of a preferred embodiment, in the case that the gripper (28 and like) travelling in the inspection section (8) is effected with matte surface treatment, the reflection of right by the gripper or like can be prevented, thus performing the inspection with high accuracy.

In another aspect of a preferred embodiment, in the case that gripper interference prevention means (42 and like) is provided for preventing interference between grippers (28 and 37) at a time of stopping one of the molding section side wheel (19b) and the inspection section side wheel (36a) adjacent to the molding section side wheel (19b), the damage of the gripper can be prevented from causing. In addition, the bottle (1) judged to be normal in the inspection section (8) can be conveyed to the following sterilization section (9) and filling section (10) by continuously revolving the wheels, thus preventing the bottles from wasting. Furthermore, since the bottle (1) can be transferred without staying in the sections following the sterilization section (9), a defect such as excessive adhering of the hydrogen peroxide to the bottle (1) can be prevented from causing. Moreover, since the bottle (1) inspected in the inspection section (8) reaches the sterilization section (9) with the remaining heat being maintained, the sterilization can be suitably performed, thus preventing the bottle (1) from wasting.

In another aspect of a preferred embodiment, in the case that an atmosphere shutoff chamber (79) is disposed between a chamber (8a) of the inspection section (8) and a chamber (9a) of the sterilization section (9), clean air is supplied into the chamber (8a) of the inspection section (8) by air supply means, and air is discharged from the atmosphere shutoff chamber (79) by discharge means, the hydrogen peroxide can be prevented from entering the inspection section (8), thus preventing the equipment in the inspection section (8) from corroding by the hydrogen peroxide.

In another aspect of a preferred embodiment, in the case that the discharge means, for discharging outside the hydrogen peroxide mist or gas from the chamber (9a) of the sterilization section (9), is disposed at a portion at which the chamber (9a) of the sterilization section (9) contacts the atmosphere shutoff chamber (79), the hydrogen peroxide flowing into the atmosphere shutoff chamber (79) can be further reduced, and the equipment in the inspection section (8) can be appropriately prevented form corroding by the hydrogen peroxide.

In another aspect of a preferred embodiment, in the case that an air nozzle (90) forming an air curtain is disposed at a portion at which the chamber (9a) of the sterilization section (9) contacts the atmosphere shutoff chamber (79), the hydrogen peroxide flowing into the atmosphere shutoff chamber (79) can be further reduced, and the equipment in the inspection section (8) can be appropriately prevented form corroding by the hydrogen peroxide.

EXPLANATION OF REFERENCE NUMERAL

Figure 1:
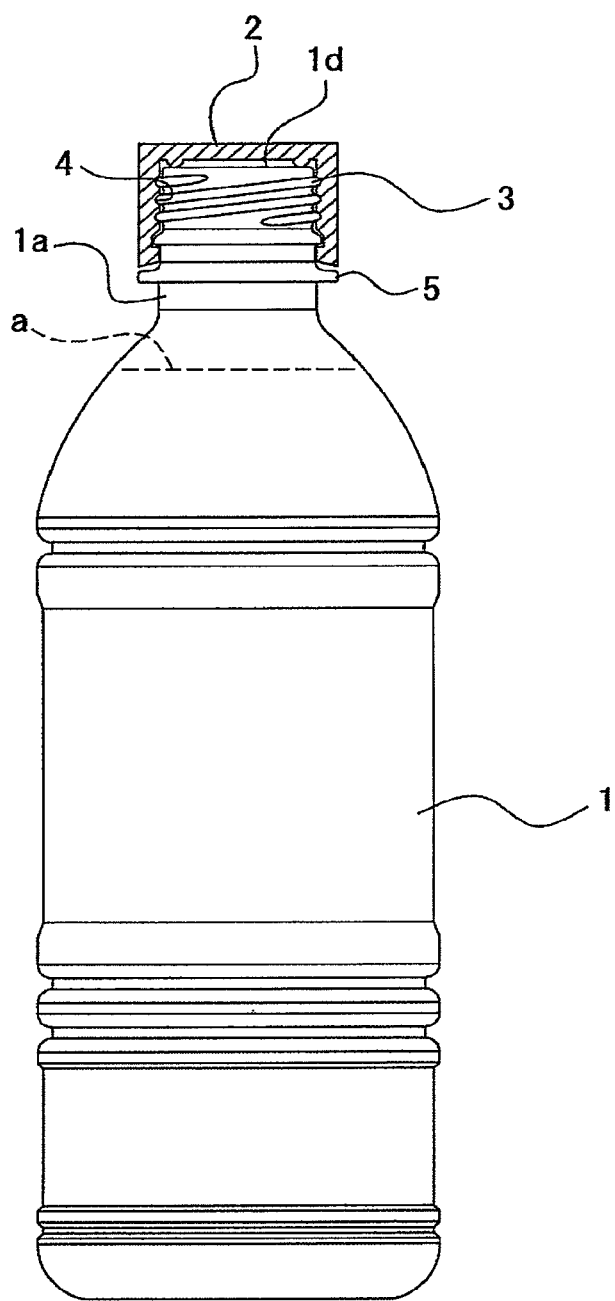
FIG. 1 is a front view of a bottle as a beverage packaging material manufactured by a beverage filling apparatus according to the present invention.

1 - - - bottle
1a - - - neck portion of bottle
1d - - - top face
5 - - - support ring
6 - - - preform
7 - - - molding section
8 - - - inspection section
8a, 9a - - - chamber
9 - - - sterilization section
10 - - - filling section
14a - - - turntable
19a, 19b, 36a - - - wheel
28, 37 - - - gripper
42 - - - piston ring
45, 48, 50, 52 - - - camera
46 - - - temperature sensor
53a - - - movable cam
85 - - - blower
79 - - - atmosphere shutoff chamber
90 - - - air nozzle
96 - - - air-rinse section
97 - - - heater
a - - - beverage
w - - - hot water
α - - - hydrogen peroxide condensed mist
β - - - hydrogen peroxide gas
γ - - - aseptic hot air
S1 - - - servo-motor

BEST MODE FOR CARRYING OUT THE INVENTION

Hereunder, exemplary modes for embodying the present invention will be described.

First Embodiment 1

First, a beverage packaging body manufactured by a beverage filling apparatus of the present invention will be described. The beverage packaging body is provided, as shown in FIG. 1, with a bottle 1 as a container and a cap 2 as a lid. In FIG. 1, a letter "a" denotes a beverage filling the bottle 1.

The bottle 1 has a shell portion substantially in a circularly cylindrical shape, but another cylindrical shape may be adopted. A bottom portion of the shell portion is closed and a neck portion 1a having a circular opening is formed to an upper portion of the shell portion.

The neck portion 1a of the bottle 1 is formed with a male threaded portion 3 and, on the other hand, a female threaded portion 4 is formed to the cap 2. When these male and female threaded portions 3 and 4 are screw-engaged, the opening of the neck portion 1a of the bottle 1 is sealed. Furthermore, the neck portion 1a of the bottle 1 is provided with a support ring 5 below the male threaded portion 4, and as mentioned hereinafter, the bottle 1 is held by the gripper through the support ring 5 and travelled in the beverage filling apparatus.

The bottle 1 is formed by blow-molding a PET preform 6 having an approximately test tube as mentioned hereinafter. However, the bottle 1 may be formed from a resin material such as polypropylene or polyethylene other than the PET. The preform 6 is molded through an injection molding process or like and is provided with a test tube shaped body portion and a neck portion 1a like that of the bottle 1. This neck portion 1a is formed with the male threaded portion at the same time of the formation of the preform 6.

The cap 2 is formed of a resin such as polyethylene or polypropylene through the injection molding process, and the female threaded portion 4 is also formed at the same time of the molding of the cap 2.

The beverage filling apparatus for filling the bottle 1 with beverage "a" will be explained hereunder.

Figure 2:
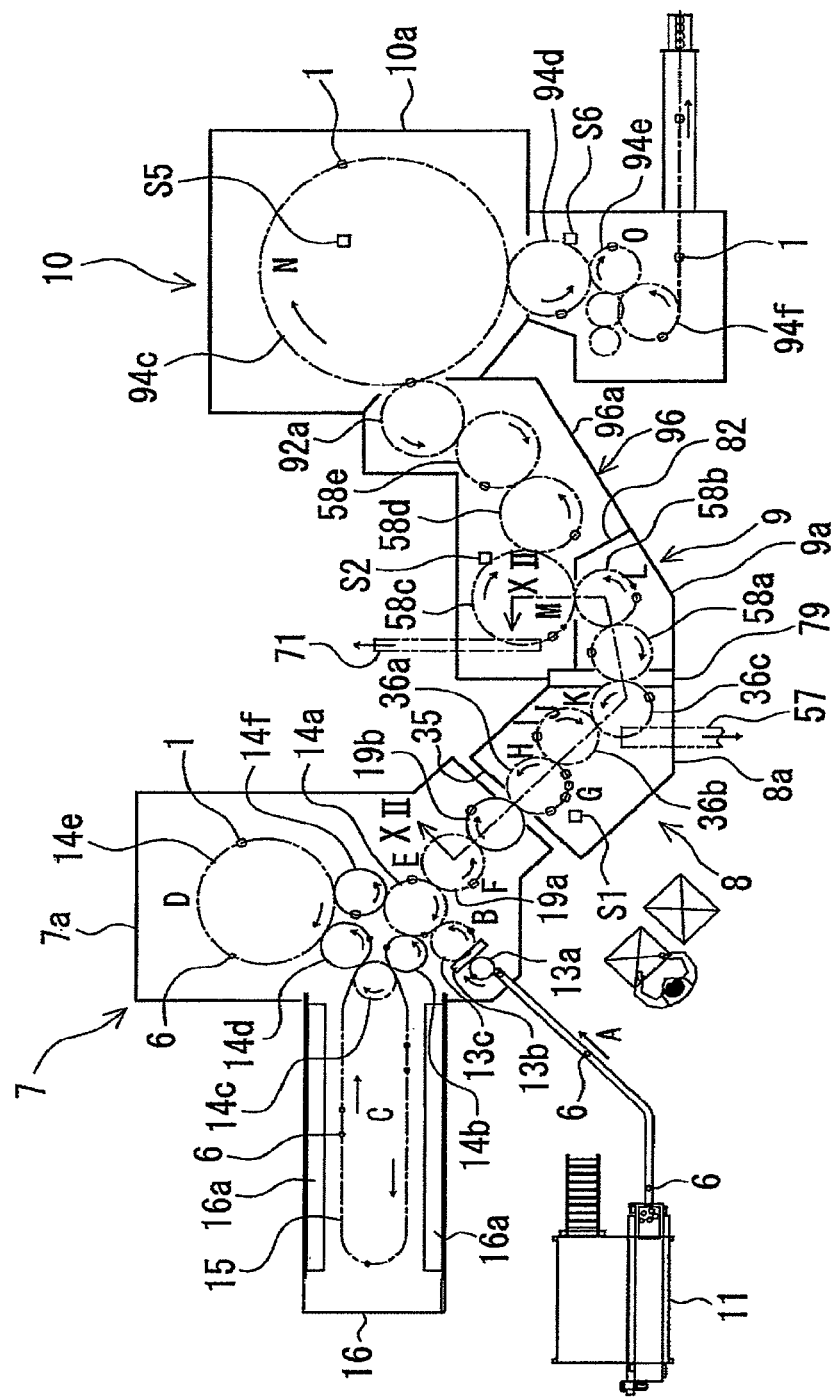
FIG. 2 is a plan view schematically showing a beverage filling apparatus according to the first embodiment of the present invention.

As shown in FIG. 2, this beverage filling apparatus is provided with a molding section 1 for molding the bottle 1, an inspection section 8 for inspecting the molded bottle 1, a sterilization section 9 for sterilizing the bottle 1, an air-rinse section 96 for air-rinsing the bottle 1, and a beverage filling section 10 for filling the bottle 1 with the beverage "a" and sealing the same.

The bottle molding section 7 is entirely covered with a chamber 7a, which is provided with a supply port for the preform 6 and a discharge port for the bottle 1.

Figure 3A:
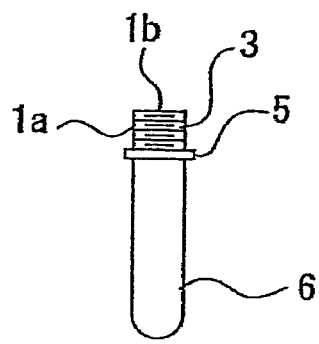
FIG. 3A is a view representing a supply process of a preform to the beverage filling apparatus.

A preform supply machine 11 is installed near the chamber 7a of the molding section 7. A plurality of preforms 6, each shown in FIG. 3A, is charged into the preform supply machine 11. The preform supply machine 11 serves to supply the preforms 6 one by one by a preform conveyer 12 into the molding section 7 through the supply port in a standing attitude with the neck portion 1a directed upward as shown in FIG. 3A.

Since the preform supply machine is per-se known machine, details thereof are omitted herein.

As shown in FIG. 2, within the chamber 7a of the molding section 7, there are arranged an upstream side wheel row, a downstream side wheel row, and a turntable row disposed between the upstream side and downstream side wheel rows.

The upstream side wheel row includes a stating end wheel 13a, as a horizontal wheel, connected to the preform conveyer 12. A plurality of grippers, not shown, for gripping the neck portions 1a of the preforms 6 are arranged at a constant pitch around the starting end wheel 13a. These grippers are rotated in accordance with the rotation of the starting end wheel 13a, and each of the preforms 6 supplied from the preform conveyer 12 is gripped at a portion near the support ring 5 by the gripper and is then conveyed to an intermediate wheel 13b.

The intermediate wheel 13b is arranged in a standing attitude, and a number of forks, not shown, are disposed at a constant pitch around the intermediate wheel 13b. This intermediate wheel 13b serves to rotate the preform 6 in an inverted state by rotating upward the preform after receiving the preform in a manner such that the forks of the intermediate wheel 13b clamp the preform 6 gripped by the gripper of the starting end wheel 13a at a portion lower than the support ring 5. The final end wheel 13c is a horizontal wheel having a gripper as like as the starting end wheel 13a, and the preform 6 inverted by the intermediate wheel 13b is gripped and received by the gripper.

The row of the turntables includes annularly arranged six turntables 14a, 14b, 14c, 14d, 14e and 14f, between which an endless chain 15 is stretched. The endless chain 15 extends and forms a circular path around the third turntable 14c. Such extended circular portion of the chain 15 travels in the heating chamber 16 disposed inside the chamber 7a. This chain 15 continuously runs in one direction shown with an arrow in FIG. 2 together with the first to six turntables 14a, 14b, 14c, 14d, 14e and 14f.

Figure 3B:
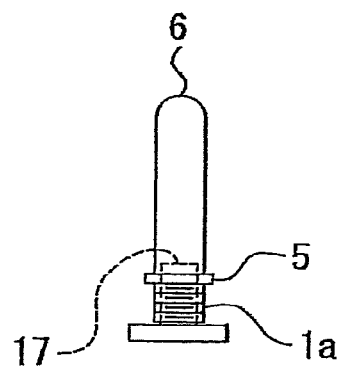
FIG. 3B is a view representing a supply process of the preform to a molding portion.

A number of mandrels 17 are coupled with the chain 15 at constant pitch as shown in FIG. 3B. The mandrel 17 may travel in an inverted attitude on the turntables 14a to 14f while being pulled by the chain 15. Further, the mandrel 17 is supported on the chain 15 to be rotatable around its axis.

The first turntable 14a is coupled with the final end wheel 13c in the upstream side wheel row, and the mandrel 17 enters, as shown in FIG. 3B, the neck portion of the inverted preform 6 held by the gripper of the final end wheel 13c and then receives the preform 6.

Figure 3C:
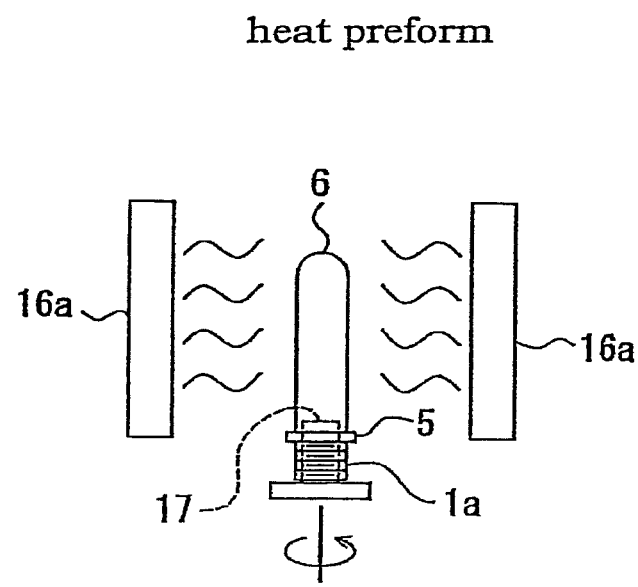
FIG. 3C is a view representing a heating process of the preform.

As shown in FIG. 3C, a heater 16a is mounted on a wall surface of the heating chamber 16. The mandrel 17 receiving the preform 6 travels along the heater 16a in the heating chamber 16, and the preform 6 held by the mandrel 17 is heated by the heater 16a as shown in FIG. 3C. According to this heating, the temperature of the preform 6 increases to a temperature by which the blow molding can be performed. The respective mandrels 17 revolve together with the preforms 6 during their running by the contact of flanged portions thereof to rails, not shown. Therefore, a portion of the preform 6 lower than the neck portion 1a thereof is heated more uniformly.

Around the fifth turntable 14e, a number of blow molding molds 18 are disposed at constant pitch. The blow molding molds 18 are rotatable in accordance with the rotation of the fifth turntable 14e.

Figure 3D:
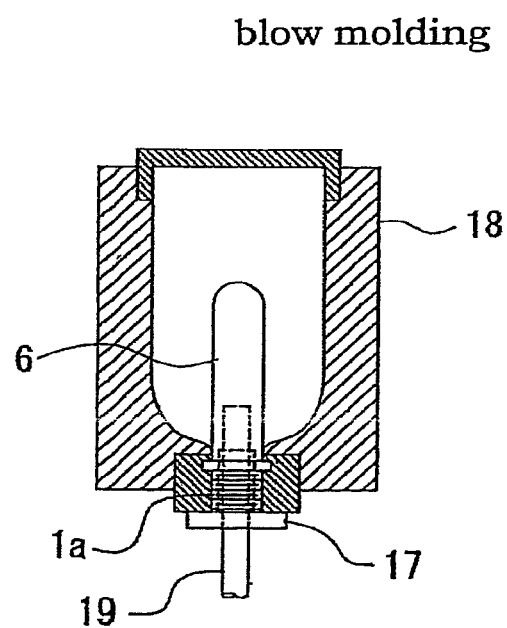
FIG. 3D is a view representing a blow molding process.

The blow molding mold 18 is splittable into a lateral pair of halves, and when the heated preform 6 is transferred from the fourth turntable 14d, the split blow molding mold halves camp the preform 6 together with the mandrel 17 as shown in FIG. 3D while rotating around the fifth turntable 14e. A through hole is formed at the central portion of the mandrel 17, and a blow nozzle 19 is inserted into this through hole toward the preform 6. Then, the bottle 1 is molded inside the mold 18 by blowing gas such as air into the preform 6 from the blow nozzle 19.

The splittable blow molding mold 18 is opened when approaching the sixth turntable 14f to thereby release the bottle 1. The bottle 1 released from the blow molding mold 18 is fed to the first turntable 14a through the sixth turntable 14f in a state being held by the mandrel 17 as shown in FIG. 3E.

The starting end wheel 19a in the downstream side wheel row is connected to the first turntable 14a mentioned above, and the final end wheel 19b contacts a discharge port of the chamber 7a of the molding portion 7.

Figure 3E:
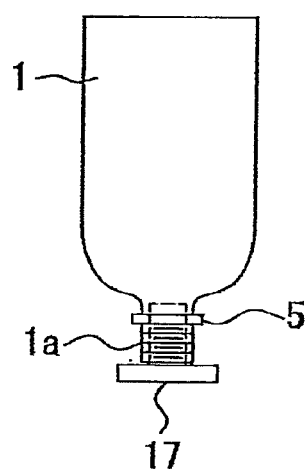
FIG. 3E is a view representing a discharge process for taking out a bottle from a molding mold.
Figure 3F:
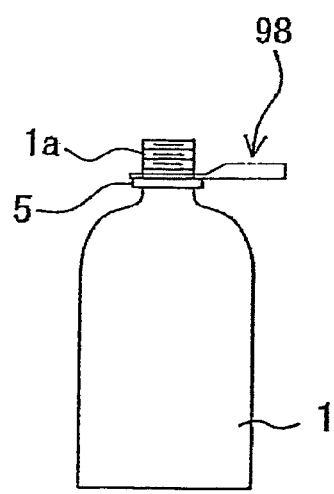
FIG. 3F is a view representing a gripping a neck portion of the bottle by means of gripper.

When the bottle 1 held by the mandrel 17 reaches as shown in FIG. 3E by the rotation of the first turntable 4a, the starting end wheel 19a grips the bottle 1 by the gripper 90 as shown in FIG. 3F and pulls off the bottle from the mandrel 17, and thereafter, the bottle 1 is inverted vertically so as to take a normal standing attitude.

Figure 4:
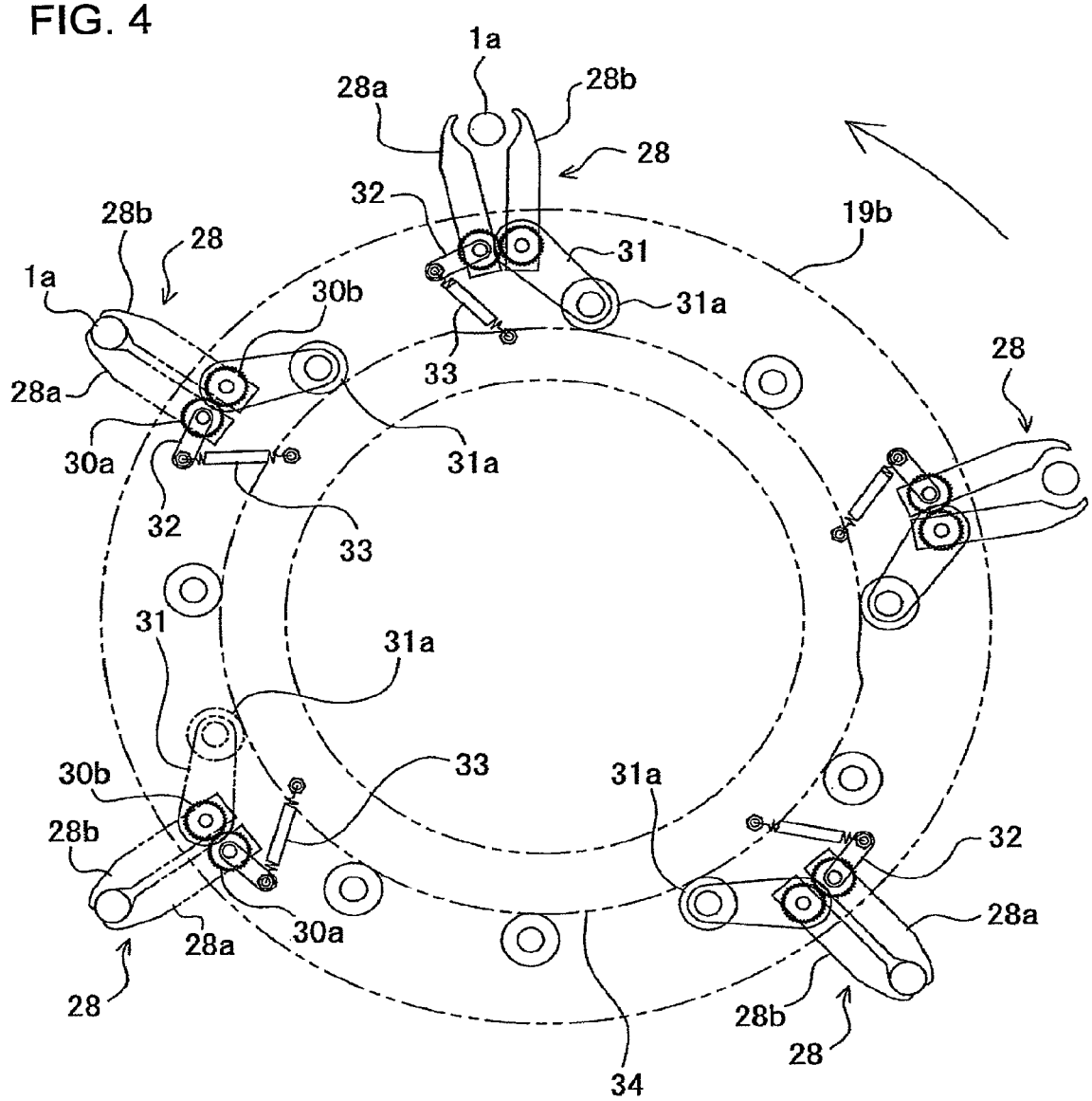
FIG. 4 is a plan view schematically showing a gripper, together with a wheel, for conveying the bottle.

The final end wheel 19b has a gripper 28 as shown in FIG. 4. This gripper 28 is provided with a pair of clamp pieces 28a, 28b clamping the neck portion 1a of the bottle 1 from the outer side thereof. The paired clamp pieces 28a and 28b are formed with base portions, respectively, which are supported by vertical pins to be rotatable. Further, a pair of gears 30a, 30b which are engageable with each other are fixed to the base portions through the vertical pins. In addition, one of the gears 30b is coupled with a cam follower 31a through a lever 31, and the other one of the gears 30a is coupled with the wheel 19b through a lever 32 and a spring 33. According to pulling force of the spring 33, a pair of clamp pieces 30a and 30b are always urged in a direction to be opened. Further, a cam 34 to which the cam follower is contacted is fixed to a frame, not shown, inside the wheel 19b.

Accordingly, when the wheel 19 is rotated, the gripper 28 serves to open the paired clamp pieces 28a and 28b through the sliding motion between the cam follower 31a and the cam 34 to thereby receive and then clamp the neck portion 1a of the bottle 1 from the gripper 28, and then the gripper 1 is turned toward the next inspection section 8 while maintaining the suspended state of the bottle 1. When the gripper 28 reaches to the inspection section 8, the paired clamp pieces 28a and 28b are opened by the sliding motion between the cam follower 31a and the cam 34 and transfer the bottle 1 to the wheel row on the inspection section side.

Figure 6:
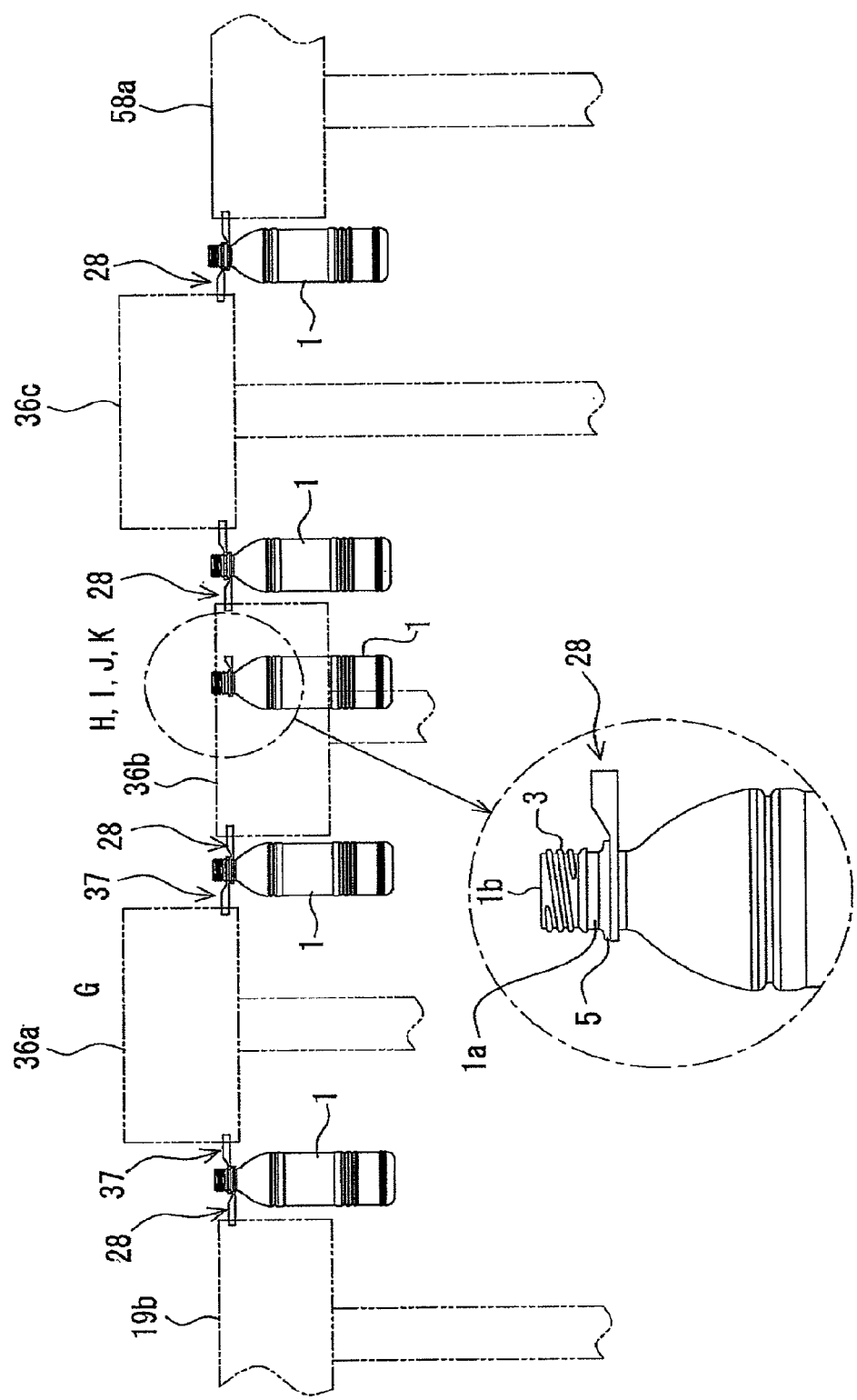
FIG. 6 is a view showing a portion arrowed with VI-VI line in FIG. 5.

When the gripper 28 of the final end wheel 19b receives the bottle 1 from the gripping member 98 of the start end wheel 19a, the gripper 28 grips the bottle 1 at a portion below the support ring 5 of the neck portion 1a of the bottle 1 as shown in FIG. 6, and the bottle 1 is conveyed in this state.

Figure 12:
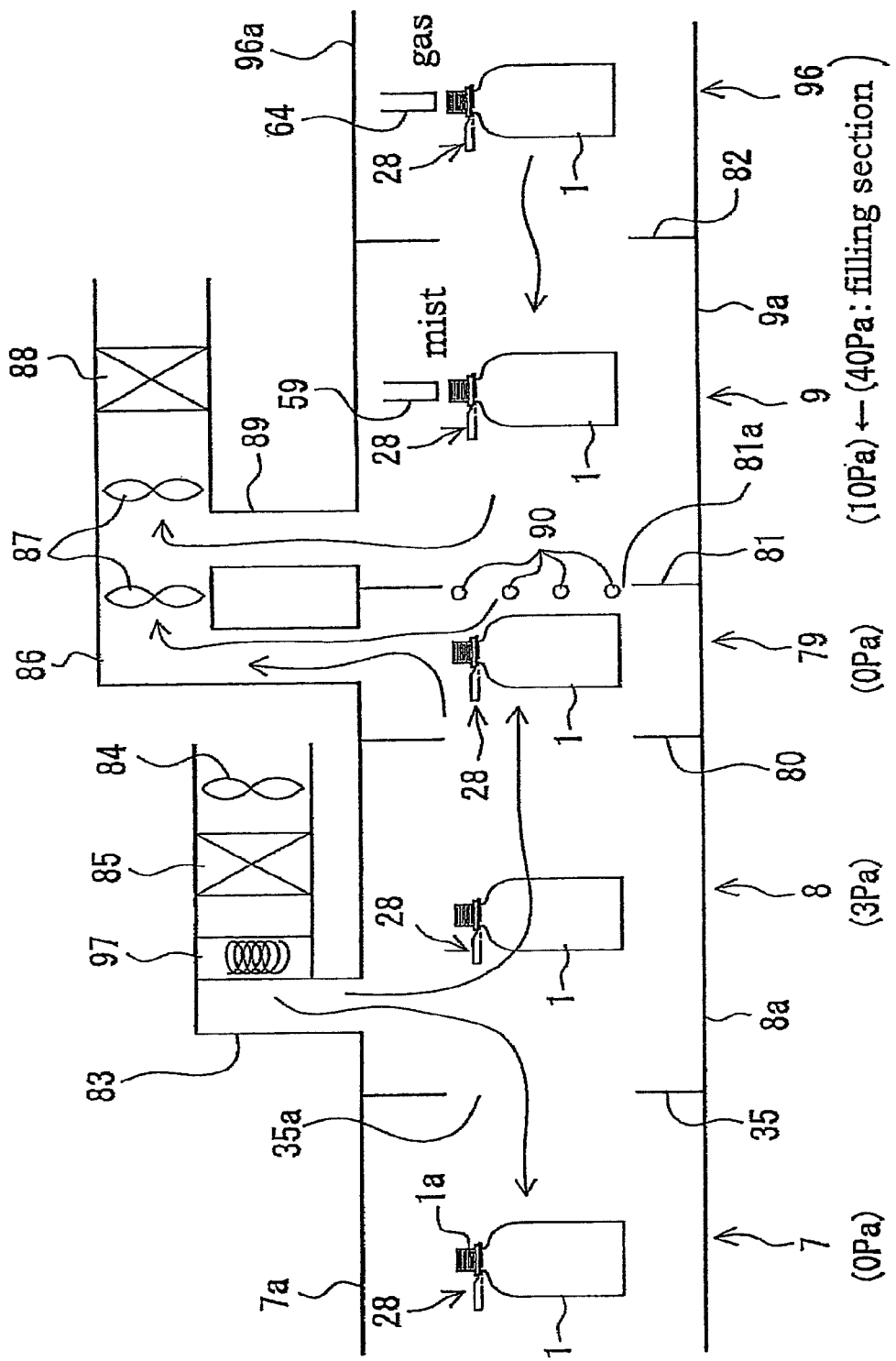
FIG. 12 is an explanation view showing positive pressure creating means and shown from arrowed direction XII-XII in FIGS. 2 and 13.

As shown in FIG. 2, the bottle inspection section 8 is connected to the bottle molding section 7. This inspection section 8 is entirely covered by the chamber 8a. As shown in FIG. 12, a bottle passing port 35a is formed to the partition wall 35 disposed between the molding section 7 and the chamber 7a thereof.

As shown in FIG. 2, the wheel row to be coupled with the final end wheel 19b as a travelling means of the bottle 1 on the molding section side is connected to the inside of the chamber 8a of the inspection section 8. More specifically, this wheel row includes three wheels 36a, 36b 36c, and a bottle travelling path is set to the outer peripheries of these wheels. Further, grippers 28 having the same structure of the gripper 28 of the final end wheel 19b is disposed around to each of these three wheels 36a, 36b and 36c. These grippers 28 grip the neck portions 1a of the bottles 1 around the wheels 36a, 36b and 36c, respectively, and then turn around, and during this motion, the bottle 1 is transferred to the final end wheel 36c from the start end wheel 36a through the intermediate wheel 36b. Thus, the bottles 1 continuously travel on the travelling path around the wheels 36a, 36b and 36c in the inspection section 8 from the final end wheel 19b in the molding section 7. During this travelling, since the clamp pieces 28a and 28b clamp the neck portion 1a of the bottle 1, the bottle 1 is conveyed in the suspended state. As shown in FIG. 6, the gripper 28 grips the neck portion 1a of the bottle 1 at a portion above the support ring 5 at the start end wheel 36a, grips the neck portion 1a of the bottle 1 at a portion below the support ring 5 at the intermediate wheel 36b, and grips the neck portion 1a of the bottle 1 at a portion above the support ring 5 at the final end wheel 36c, and in this manner, the bottle 1 is conveyed in the inspection section 8 from the upstream side toward the downstream side.

Gripper interference preventing means is disposed to the start end wheel 36a in the inspection section 8 contacting to the final end wheel 19b on the bottle molding section 7 side for the purpose of preventing interference between the gripper 28 mounted to the final end wheel 19b on the molding section side and the gripper 28 of the start end wheel 36a of the inspection section side at a time when the turntable or wheel on the bottle molding section side is emergently stopped.

Figure 7:
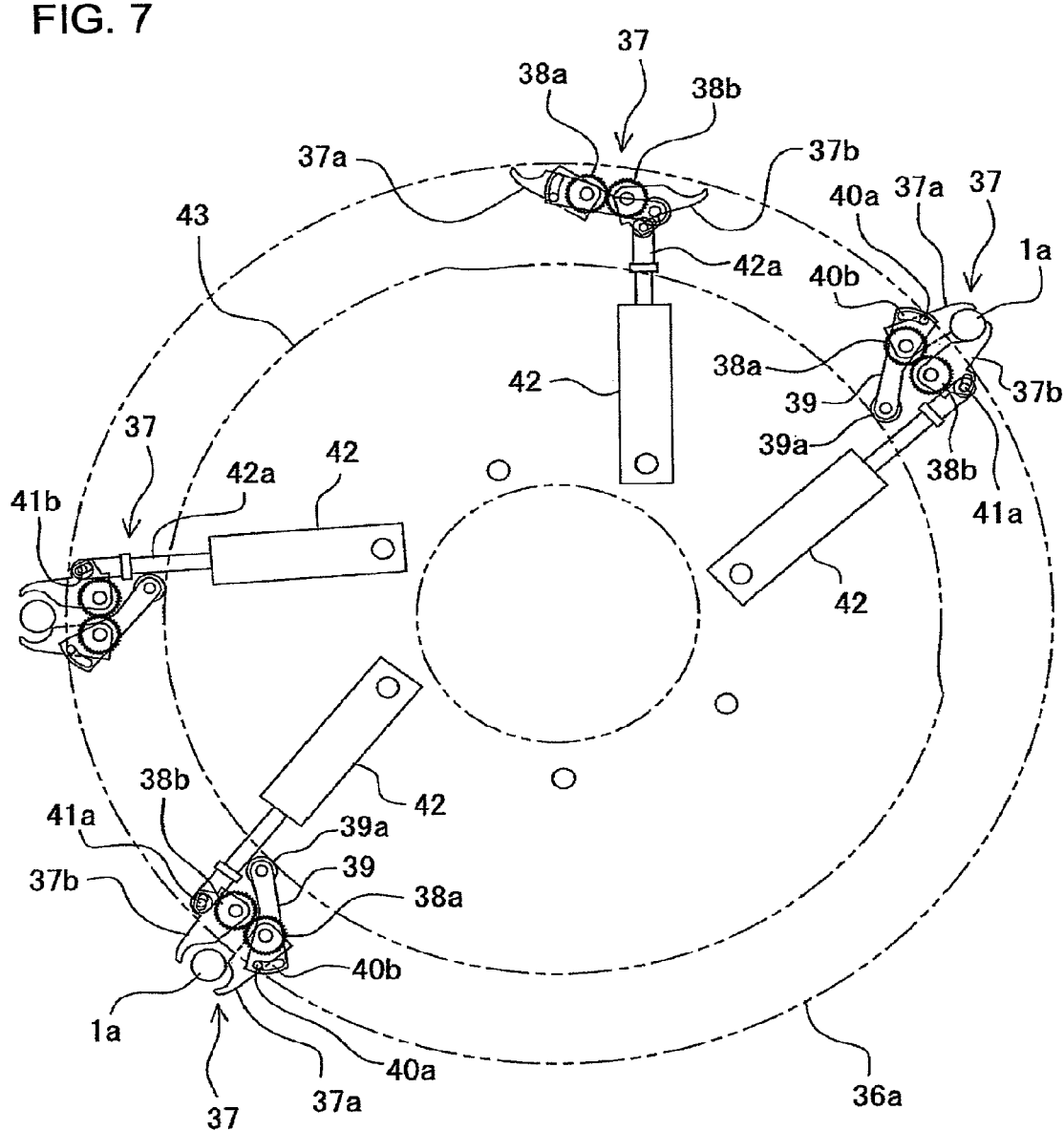
FIG. 7 is a plan view schematically showing a gripper, together with a wheel, provided with interference prevention means.

As shown in FIG. 7, a gripper 37 of the start end wheel 36a in the inspection section 8 has a structure different from the gripper 28 because of the provision of the gripper interference preventing means.

That is, as shown in FIG. 7, a plurality of grippers 37 are mounted to the start end wheel 36a in the inspection section 8 at a predetermined pitch, and each of the grippers 37 has a pair of clamp pieces 37a and 37b for clamping the neck portion 1a of the bottle 1 from the outer side thereof, and base portions of the paired clamp pieces 37a, 37b are supported to be pivotal to the wheel 36a by means of vertical pins, respectively, and a pair of mesh gears 38a and 38b are fixed to the base portions of these clamp pieces 37 and 37a by means of vertical pins.

Furthermore, a cam follower 39a is coupled with one of the gears 38a through one end of a lever 39, and one of the clamp pieces 37a is coupled with the other end of the lever 39 opposing the cam follower 39a through a pin 40a and a circular-arc-shaped slot 40b. On the other hand, the other clamp piece 37b is formed integrally with the other gear 38b, and the clamp piece 37b is coupled with a piston rod 42a of a piston-cylinder assembly 42 through a pin 41a and a circular-arc-shaped slot 41b. The piston-cylinder assembly 42 is supported by the wheel 36a.

A torsion spring, not shown, is disposed between the gears 38a, 38b and the wheel 36a, and a pair of clamp pieces 37a and 37b is always urged in the closing direction by the twisting force of the torsion spring. Further, the cam follower 39a is also always pushed against the cam 43.

According to the structure or arrangement mentioned above, when the start end wheel on the inspection side is rotated, the gripper 37 opens the paired clamp pieces 37a and 37b and receives the neck portion 1a of the bottle 1 from the gripper 28 of the final end wheel on the molding section side. Thereafter, the neck portion 1a of the bottle 1 is clamped and turned with the bottle 1 being maintained in its suspended state. The clamp pieces 37a and 37b are rotated in the opening direction against the twisting force of the torsion spring, and in this instance, the respective pins 40a and 41a are slid in the circular-arc-shaped slits 40b and 41b, respectively.

By the way, there may be caused a case where some abnormality is caused on the side of the molding section 7, and the turntable row or wheel row is emergently stopped. In such occasion, as shown in FIG. 7, the piston rod 42a of the piston-cylinder assembly 42 is contracted, thereby widening the closed paired clamp pieces 37a and 37b to about 180 degrees opened position. Accordingly, the interference between the gripper 28 mounted to the final end wheel 19b on the molding section side and the gripper 37 mounted to the start end wheel 36a can be prevented from causing. In this case, the start end wheel 36a and the subsequent wheel row of the wheel 36b are being rotated, so that the bottle 1 introduced into the inspection section 8 is continuously travelled toward the downstream side.

Figure 18:
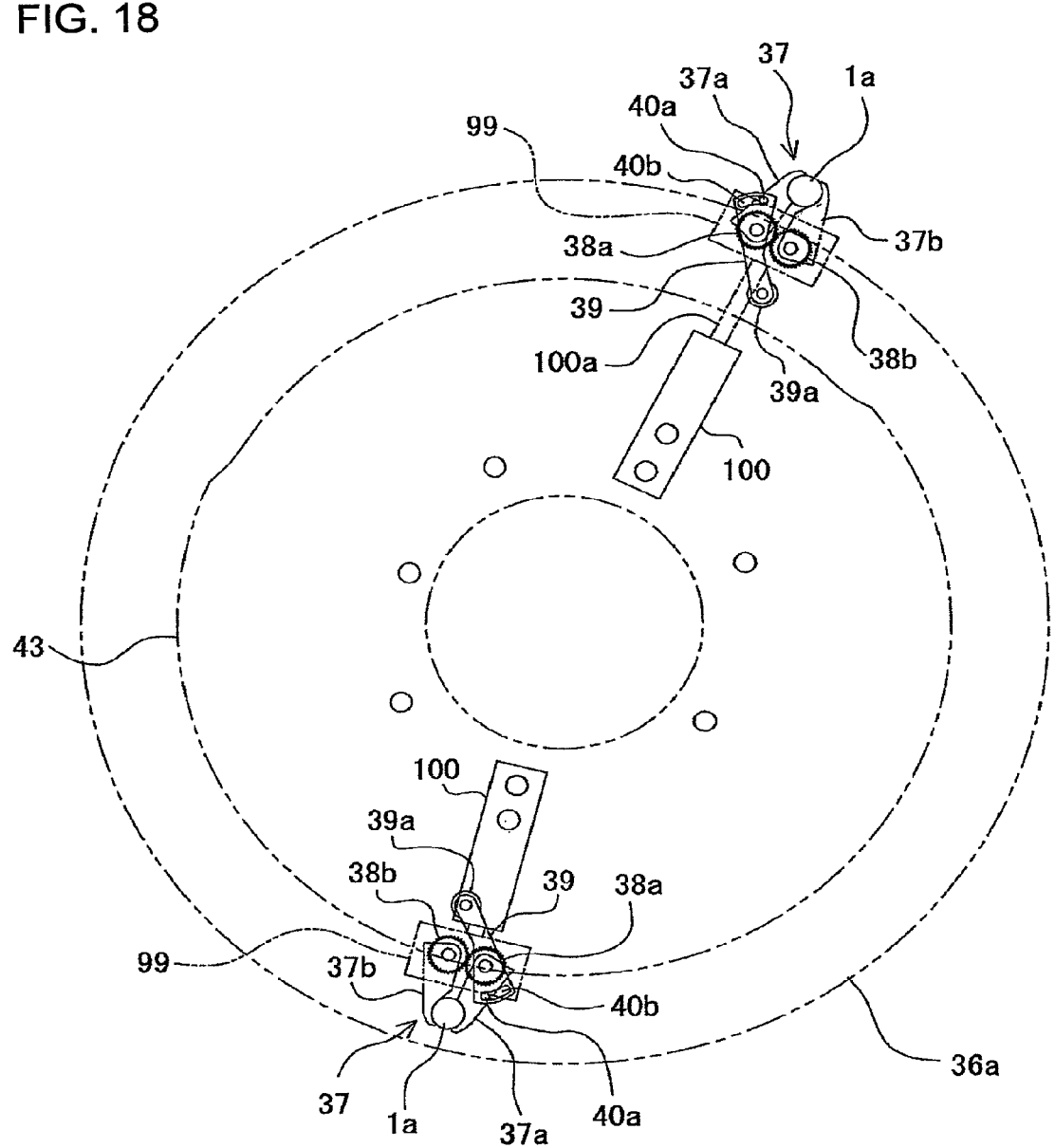
FIG. 18 is a schematic plan view, like FIG. 7, representing another example of the interference prevention means.

Further, the gripper interference preventing means is not limited to the structure mentioned above, and as shown in FIG. 18, there may be adopted a slide structure in which the gripper 37 is reciprocally slid in the radial direction of the wheel 36a. In FIG. 18, reference numeral 99 denotes a holding member holding the gripper 37, and a piston rod 100a of a piston-cylinder assembly 100 is connected to the holding member 99. The piston-cylinder assembly 100 is fixed to the wheel 36a along the radial direction thereof.

In an occasion in which when any abnormal event is generated on the molding section side and the turntable row and the wheel row on the molding section side are emergently stopped, as shown in FIG. 18, the piston rod 100a of the piston-cylinder assembly 100 is contracted and the gripper 37, which protrudes outward in the radial direction of the wheel 36a, is pulled inward in the radial direction. According to such motion, the interference between the gripper 28 mounted to the final end side wheel 19b on the molding section side and the gripper 37 of the start end wheel 36a on the inspection section side can be prevented.

Further, for the gripper interference preventing means shown in FIG. 18, when the piston rod 100a is contracted, the cam 43 operating for opening or closing the paired clamp pieces 37a, 37b of the gripper 37 is moved in the axial direction of the wheel 36a by an actuation of another piston-cylinder assembly, for example, and accordingly, the cam 43 is moved so as to escape to a position not abutting against the cam follower 39a.

Figure 19:
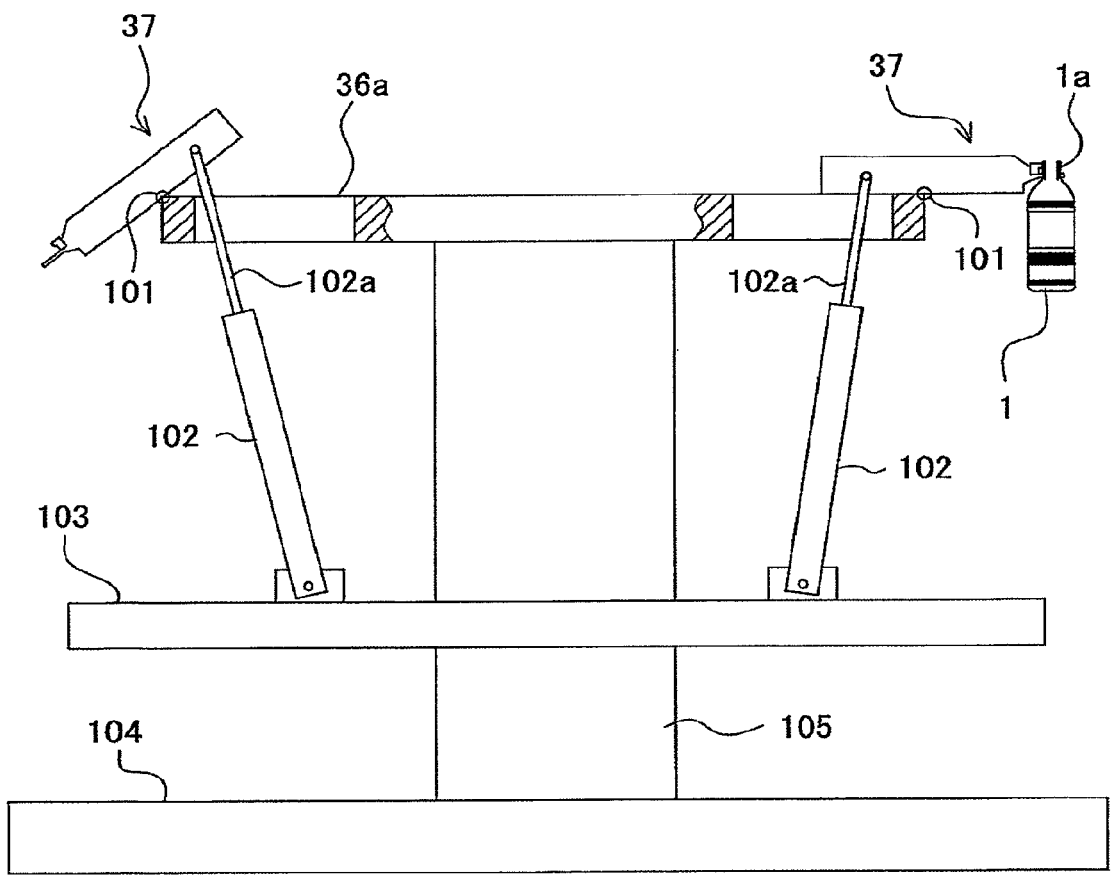
FIG. 19 is a schematic elevational view representing a further example of the interference prevention means.

Further, as the gripper interference preventing means, as shown in FIG. 19, a rotating mechanism for rotating the gripper 37 in the vertical direction of the wheel 36a may be employed. The gripper 37 is coupled with a hinge 101 to be rotatable in the vertical direction with respect to the wheel 36a and is then coupled with a wheel 103 which is integrally rotatable with the wheel 36a through a piston-cylinder assembly 102.

Figure 22:
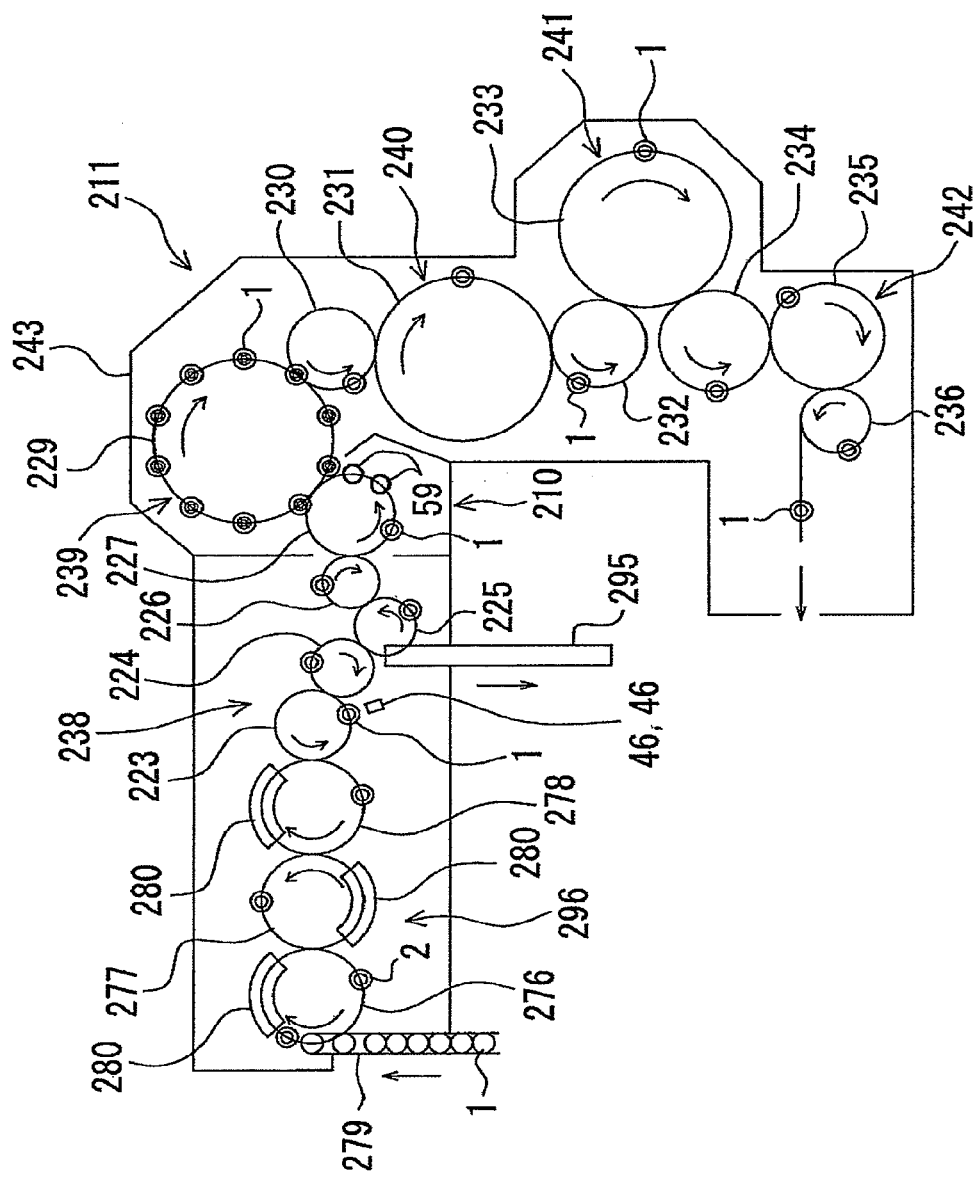
FIG. 22 is a schematic plan view representing a beverage filling apparatus according to a fourth embodiment of the present invention.

In an occasion in which when any abnormal event is generated on the molding section side and the turntable row and the wheel row on the molding section side are emergently stopped, as shown in FIG. 22, the piston rod 102a of the piston-cylinder assembly 102 is expanded and the gripper 37, which protrudes outward in the radial direction of the wheel 36a, is rotated downward as the hinge 101 being a fulcrum point. According to this motion, the interference between the gripper 28 mounted to the final end side wheel 19b on the molding section side and the gripper 37 of the start end wheel 36a on the inspection section side can be prevented. Further, in FIG. 19, reference numeral 104 denotes a machine table supporting a swivelling shaft 105 of the wheels 36a and 103.

Further, in the embodiment described above, the structure in which the gripper 37 is pivoted downward was employed, a structure in which the gripper is pivoted upward may be employed.

Figure 3G:
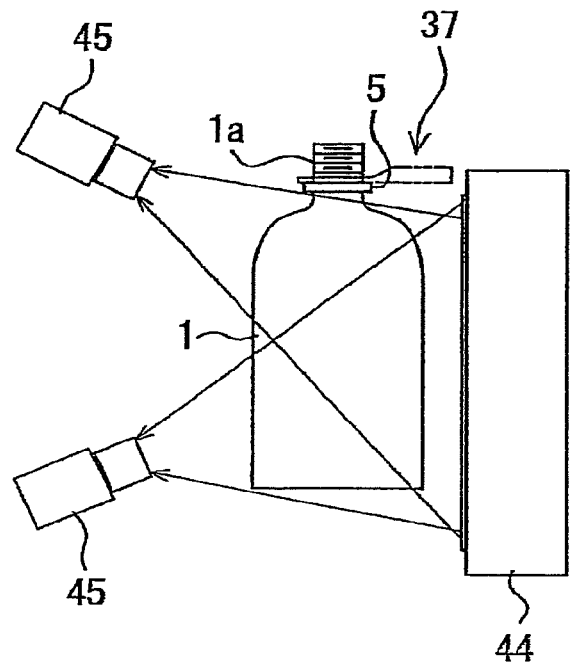
FIG. 3G is a view representing a bottle shell inspection process.
Figure 5:
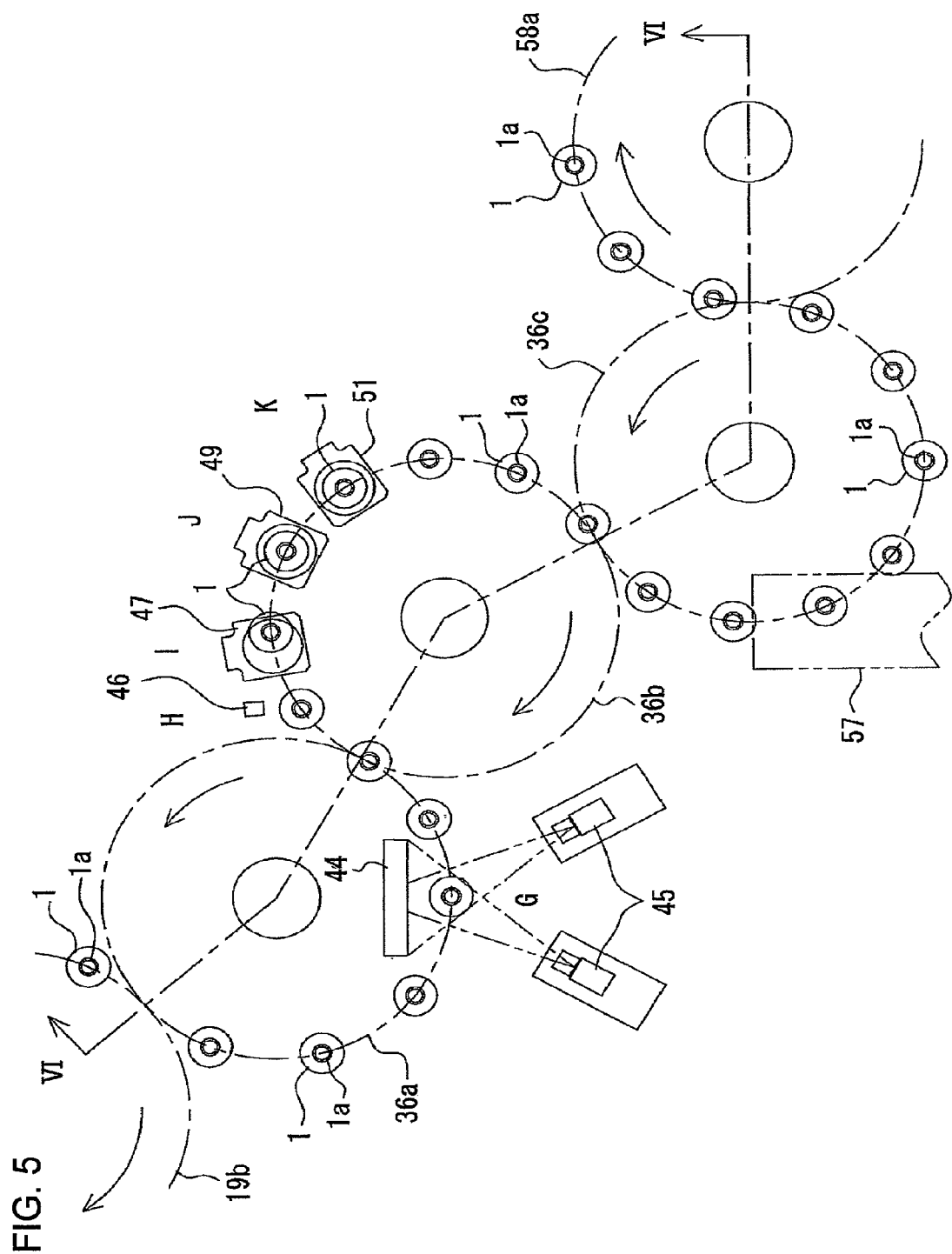
FIG. 5 is an enlarged view of an inspection portion in FIG. 2.

As shown in FIG. 3G and FIG. 5, a lamp 44 as lighting means and a camera 45 as imaging pick-up means are disposed at predetermined positions around the start end wheel 36a in the chamber 8a of the inspection section 8, and the lamp 44 and the camera 45 are arranged as bottle shell portion inspection means discriminating the quality of the bottle by imaging a circular or rectangular cylindrical shell portion of the bottle 1.

Irradiation light from the lamp 44 penetrates the shell portion of the bottle 1 and the camera 45 receives the irradiation light and then images the bottle 1. The pick-up image of the shell portion of the bottle 1 is processed by an image processing device, not shown, so as to discriminate whether any abnormality such as injury, foreign material, discoloration or like is caused or not.

As shown in FIGS. 3H, 3I, 3J and 3K, and FIG. 5, a temperature sensor 46, a lamp 47 and a camera 48, a lamp 49 and a camera 50, and a lamp 51 and a camera 52 are arranged in the described order along the intermediate wheel 36b disposed in adjacent to the start end wheel 36a. The temperature sensor 46 constitutes temperature inspection means which detects a temperature of the bottle 1 and discriminates the quality of the bottle 1. The lamp 47 as lighting means and the camera 48 as imaging means constitute support ring inspection means which images the support ring 5 of the neck portion 1a of the bottle 1 and discriminates the quality of the bottle 1. The lamp 49 as lighting means and the camera 50 as imaging means constitute bottle neck portion upper face inspection means which images the flat and smooth ring-shaped face of the neck portion 1a of the bottle 1 and discriminates the quality of the bottle 1. The lamp 51 as lighting means and the camera 52 as bottle bottom portion inspection means which images the bottom portion of the bottle 1 and discriminates the quality of the bottle 1.

The respective means mentioned above may be altered in the arrangement order and in the positions, or may be optionally eliminated in location, or another inspection means may be optionally added.

Figure 3H:
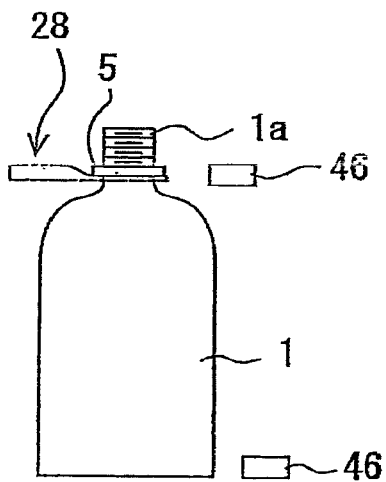
FIG. 3H is a view representing a bottle temperature inspection process.

The temperature sensor 46 is, for example, an infrared radiation thermometer, but another thermometer may be employed. The temperature sensors 46 are disposed so as to oppose to the support ring 5 of the neck portion 1a of the bottle 1 and the bottom portion thereof, respectively, as shown in FIG. 3H.

The bottle 1 travels around the start end wheel 36a and the intermediate wheel 36b at a predetermined speed while maintaining the remaining heat at the molding section 7 and being gripped by the gripper 28, and the temperature of the bottle surface is detected during this travelling. The remaining heat of the bottle 1 is necessary for appropriately sterilizing the bottle 1 with hydrogen peroxide in the latter stage, and it is desirable that the temperature of the bottle surface to be detected by the temperature sensor 46 is more than 50° C.

In the temperature detection mentioned above, when at least either one of the temperatures detected by two portions of the bottle 1 by two temperature sensors 46 does not reach the predetermined temperature, it is discriminated that the detected bottle 1 is defective one. That is, the bottle 1 of which temperature does not reach the predetermined temperature may have possibility of being insufficiently sterilized even by the hydrogen peroxide sterilization in the latter stage. On the contrary, the bottle 1 of which temperature reaches the predetermined temperature can be sufficiently sterilized by the hydrogen peroxide sterilization performed in the latter stage.

The two portions of the bottle 1 of which temperatures are to be detected are portions having thick resin thickness and which are liable to cause cold spots. However, the temperature sensors 46 may be arranged to portions other than the two portions mentioned above, and the locating number may be changed in accordance with the shape and size of the bottle 1, the kind of the molding (injection) mold or like. For example, the temperature sensor 46 may be disposed only to the portion opposing to the bottom portion of the bottle 1 at which a cold spot is liable to be caused.

Furthermore, since the heat of the thin portion of the bottle 1 is liable to escape in comparison with the thickened portion thereof, the temperature sensor 46 may be disposed so as to oppose to the thin thickness shell portion of the bottle 1. According to this arrangement, only the bottle 1 maintaining the remaining heat minimally necessary for the sterilization of the bottle in the latter stage may be transferred to the sterilization section 9.

Figure 3I:
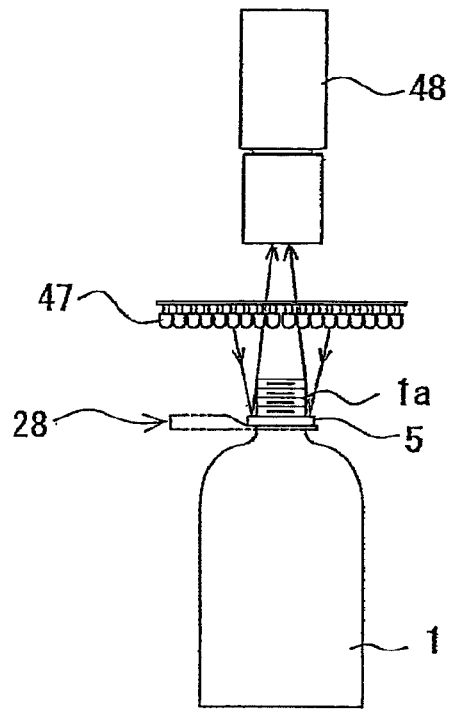
FIG. 3I is a view representing a bottle support ring inspection process.

As shown in FIG. 3I and FIG. 5, the lamp 47 as the support ring inspection means is annularly disposed above the support ring 5 of the neck portion 1a of the bottle 1. More specifically, the lamp 47 is composed of LED (light emitting diode) disposed annularly. The camera 48 is arranged so as to receive the light of the lamp 47 reflected by the upper surface of the support ring 5, thus the support ring 5 being imaged. At this time, since the clamp pieces 28a, 28b of the gripper 28 grip the neck portion 1a at the lower portion of the support ring 5, as shown in FIG. 6, the imaging operation to the support ring 5 cannot be obstructed by the clamp pieces 28a, 28b of the gripper 28. The upper surface condition of the support ring 5 is specifically inspected by this support ring inspection means.

The image of the support ring 5 picked up by the camera 48 is processed by the image processing device, not shown, and it is discriminated whether any abnormality such as injury, deformation or like may be exist. caused, Because the support ring 5 may be contacted or touched by a customer who obtains the bottle 1 as a beverage bottle when the cap thereof is opened, the existence of any injury or deformation is not desirable, and a bottle 1 having injury or deformation of an extent beyond allowance is judged as defective product.

Figure 3J:
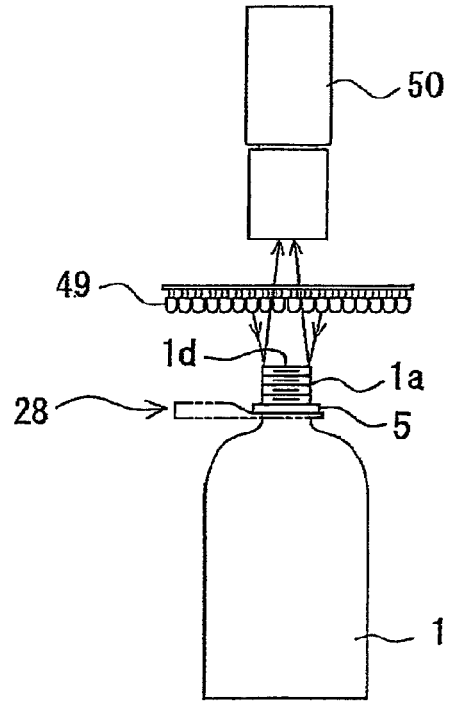
FIG. 3J is a view representing an inspection process for inspecting a top face of the neck portion of the bottle.

As shown in FIG. 3J and FIG. 5, the lamp 49 as the bottle neck portion upper face inspection means is annularly arranged above the upper (top) face 1d of the bottle neck portion 1a. More specifically, the lamp 49 is composed of LED (light emitting diode) disposed annularly. The camera 50 is arranged so as to receive the light of the lamp 49 reflected by the upper face 1d of the support ring 5, thus the upper face 1d of the support ring 5 being imaged. The image of the upper face 1d picked up by the camera 50 is processed by the image processing device, not shown, and existence of abnormality such as injury, deformation or like is discriminated. The upper face 1d of the bottle neck portion 1a is a portion for sealing the interior of the bottle 1 in contact of this upper face 1d of the bottle neck portion 1a to the ceiling portion of the cap 2 (see FIG. 1), so that the upper face 1d of the bottle neck portion 1a is required to be flat and smooth. Because of this reason, a bottle 1 detected to have injury or deformation is judged to be a defective product.

Figure 3K:
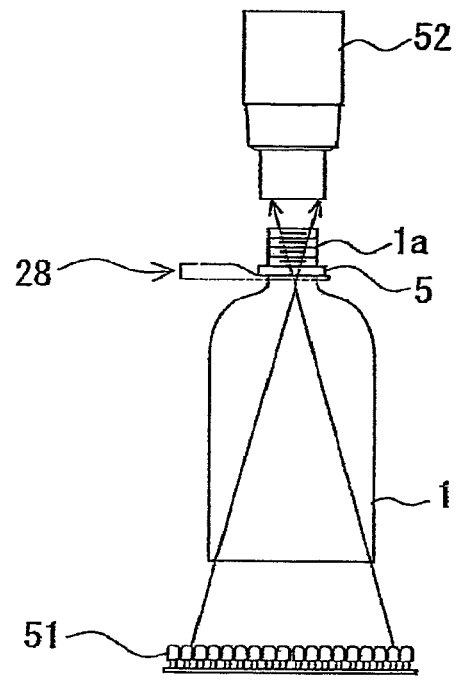
FIG. 3K is a view representing a bottle bottom portion inspection process.

As shown in FIG. 3K and FIG. 5, the lamp 51 as the bottle bottom portion inspection means is annularly arranged below the bottom portion of the bottle 1. More specifically, the lamp 49 is composed of LED (light emitting diode) disposed annularly. The camera 52 is arranged so as to receive the light of the lamp 49 passing through the bottom portion of the bottle 1, thus the bottom portion of the bottle 1 being imaged. The image of the bottom portion of the bottle 1 picked up by the camera 52 is processed by the image processing device, not shown, and existence of abnormality such as injury, deformation or like is discriminated.

Further, although not shown, the gripper 28 travelling inside the inspection section 8 is effected with a matte surface working. According to this surface working, inspection miss due to reflection of irradiation light from the respective lamps 47, 49 and 51 to the gripper 28 can be prevented from causing. In addition, a peeping (inspection) hole, not shown, is formed to the chamber 8a of the inspection section 8, and a muffled glass is fitted to the peeping hole so that outside light is prevented from entering inside the chamber 8a.

Figure 8:
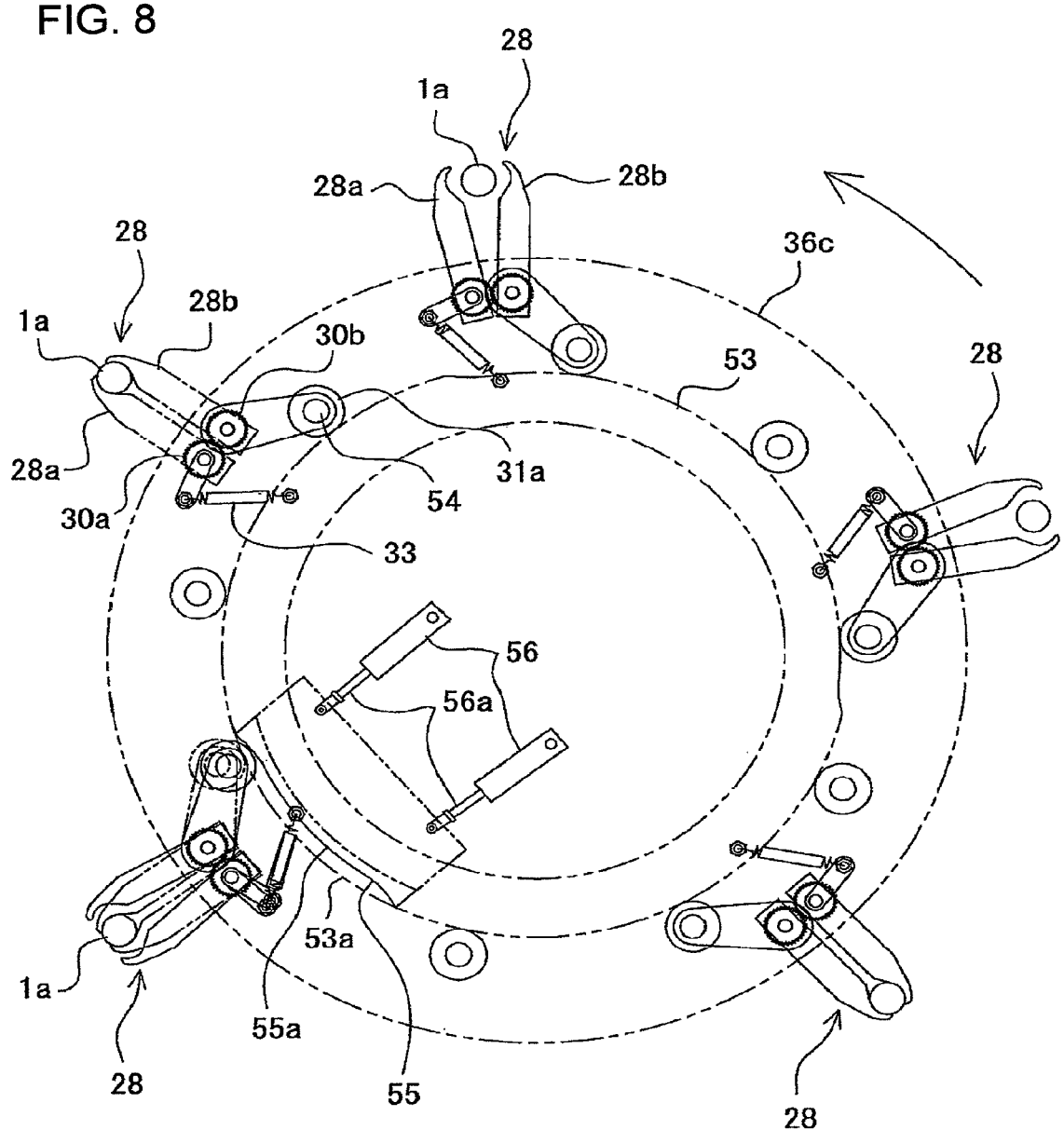
FIG. 8 is a plan view schematically showing a gripper, together with a wheel, provided with a defective bottle removing means.

The final end wheel 36c contacting the intermediate wheel 36c from the downstream side thereof is provided, as shown in FIG. 8, with a gripper 28 of the structure similar to the gripper 28 of the intermediate wheel 36b. When the final end wheel 36c is rotated, due to the slide-contact function between the cam follower 31a and the cam 53, the gripper 28 opens the paired clamping pieces 28a, 28b so as to clamp the bottle neck portion 1a after receiving the neck portion 1a of the bottle 1 from the gripper 28 of the intermediate wheel 36b, and then, swivels bottle 1 to the subsequent sterilization section 9 while holding the bottle in the suspended attitude. When the gripper 28 reaches the sterilization section 9, the paired clamp pieces 28a, 28b are opened by the slide-contact function between the cam follower 31a and the cam 53, and then, the bottle 1 is transferred to the wheel on the sterilization section side. The cam 53 is fixed to a stationary frame, not shown, disposed inside the final end wheel 36c.

The final end wheel 36c is provided with discharge means for discharging the bottle 1, which was judged as defective product by the inspection in the inspection section 8, from the bottle travelling path.

The discharge means has a gripper releasing mechanism such as shown in FIGS. 8 and 9. The gripper releasing mechanism includes an additional cam follower 31b further added to the pivot shaft 54 of the cam follower 31a and having a shape similar to the cam follower 31a, and another additional cam follower 55 contacting the additional cam follower 31b and being different partially in shape, the additional cam follower 55 being disposed below the cam 53. Furthermore, the gripper releasing mechanism further includes a movable cam 53a as one portion separated from the cam 53 to be movable.

The movable cam 53a is inserted into a portion partially cut out from the stationary cam 53 to be slidable in the radial direction thereof, and is coupled with a piston rod 56a of a piston-cylinder assembly 56 coupled with the frame, not shown, at a portion inside the wheel 36c. Further, a recessed portion 55a, into which the additional cam follower 31b is fitted, is formed to a portion of the additional cam 55 corresponding to the movable cam 53a.

The discharge means is further provided with a cylindrical shooter for discharging the defective bottle denoted by the reference numeral 57 in FIGS. 2 and 5.

Figure 9A:
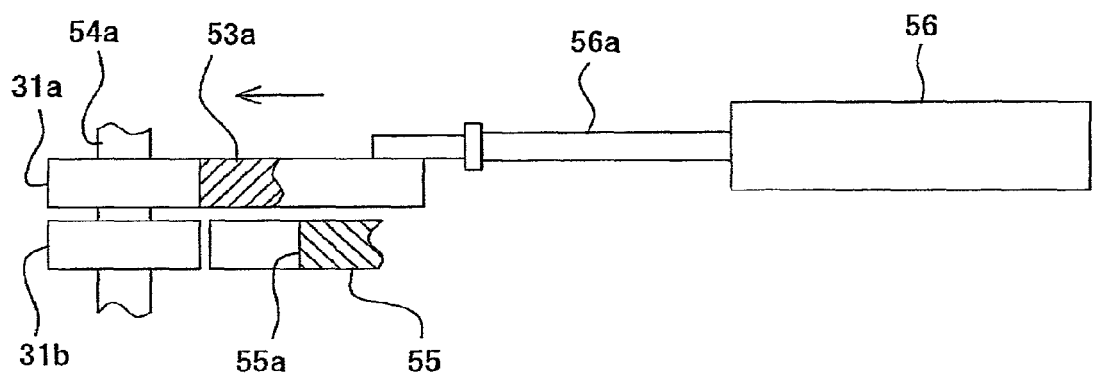
FIG. 9A is a side view showing the defective bottle removing means in a non-operative state.
Figure 9B:
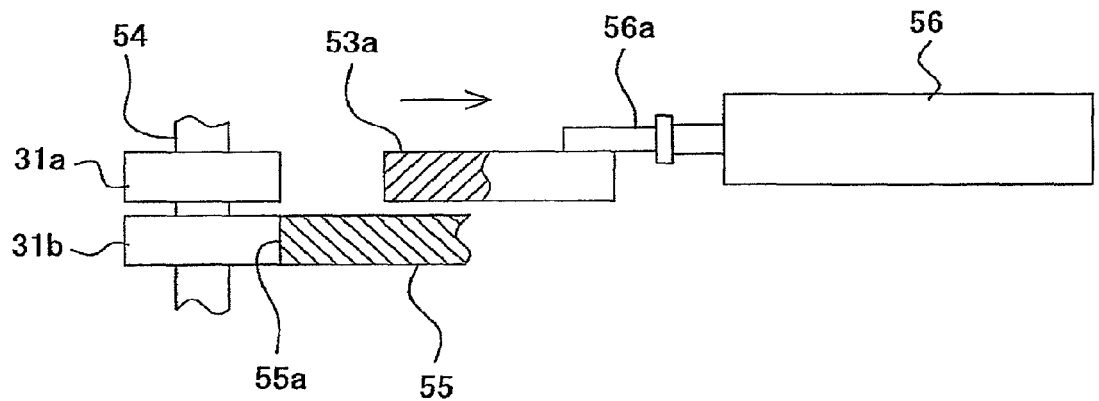
FIG. 9B is a side view showing the defective bottle removing means in an operating state.

When a signal representing that the bottle 1, which is judged as defective product by the inspection section 8, is defective, is generated, the piston-cylinder assembly in the expanded state as shown in FIG. 9A is contracted as shown in FIG. 9B, and the movable cam 53a is retired in the radially inside direction of the cam 53. Accordingly, the additional cam follower 31b is invaded into the recessed portion 55a of the additional cam 55, and the paired clamp pieces 28a, 28b of the gripper 28 are opened as shown with solid line from the closed state shown with two-dot-chain-line, thus releasing the defective bottle 1. The bottle 1 as defective product drops down from the gripper 28, and then transferred to a predetermined collecting section through the shooter 57. The bottle 1 judged to be a good product passes through the discharge means, because the movable cam 53a is held at the position shown in FIG. 9A, and then is transferred to the sterilization section 9.

As shown in FIG. 2, the sterilization section 9 is connected to the bottle inspection section 8. The bottle sterilization section 9 is also entirely covered with the chamber 9a.

The wheel row coupled with the final end wheel 36c as bottle travelling means on the inspection section side is provided inside of the chamber 9a of the sterilization section 9. More specifically, this wheel row is composed of two wheels 58a, 58b, and a bottle travelling path is formed around outer peripheral portions of these wheels 58a, 58b. Grippers 28, each having a structure similar to that of the gripper 28 shown in FIG. 4, are disposed around these wheels 58a and 58b, respectively.

The gripper 28 transfers the bottle 1 from the start end wheel 58a to the final end wheel 58b while gripping the bottle neck portion 1a and swivelling around these wheels. According to such motion, the good bottle 1 after the inspection is continuously travelled on the travelling path from the final end wheel 36c in the inspection section 8 towards the final end wheel 58b in the sterilization section 9. The gripper 28 grips the bottle neck portion 1a by the clamp pieces 28a and 28b during the travelling of the bottle 1, and the bottle 1 is hence travelled in the vertically suspended state.

Figure 3L:
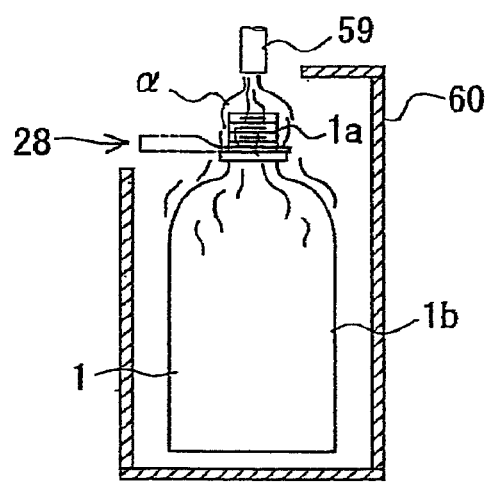
FIG. 3L is a view representing a bottle sterilization process by using condensed mist of hydrogen peroxide.

A spray tube 59 as condensed mist supply means for supplying condensed mist α of the hydrogen peroxide as a sterilizing agent for the bottle 1 is disposed to a predetermined portion around the intermediate wheel 58b contacting from the downstream side to the start end wheel 58a in the chamber 9a of the sterilization section 9 as shown in FIG. 3L. The spray tube 59 is fixed to a predetermined position so that a front end formed with a nozzle hole of the spray tube 59 directly faces the opening of the neck portion 1a of the good bottle 1 travelling just below the nozzle hole.

Furthermore, as shown in FIG. 3L, a tunnel 60 may be formed along the bottle travelling path below the spray tube 59 as occasion demands.

One or a plurality of the spray tube 59 may be disposed, which is arranged along the outer periphery of the intermediate wheel 58b. In the shown embodiment, although the spray tube 59 is disposed around the intermediate wheel 58b, the spray tube 59 may be arranged around the other wheel.

Figure 10:
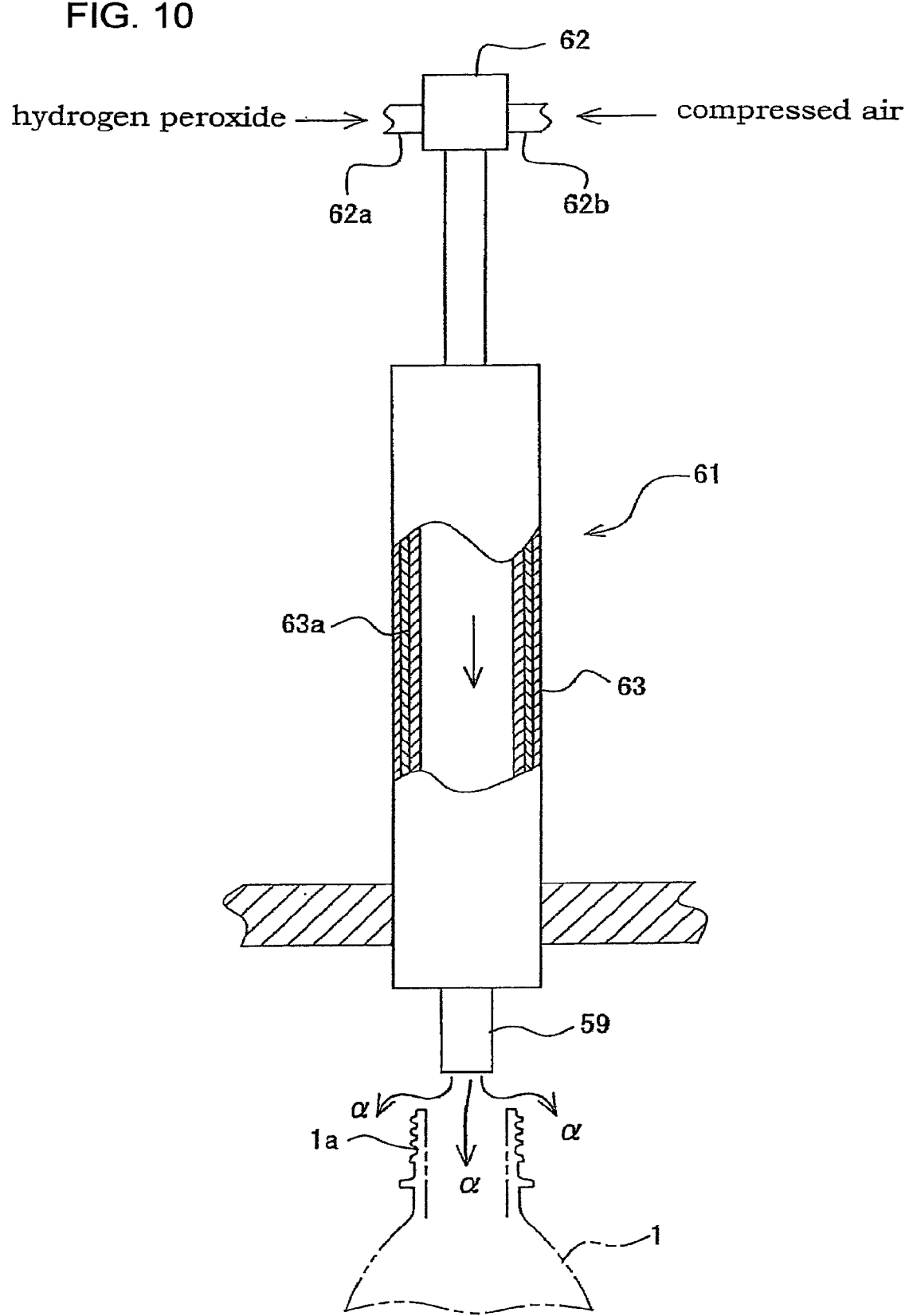
FIG. 10 is a front view of a mist generation device which is partially cut away.

The condensed mist α of the hydrogen peroxide is produced by condensing the hydrogen peroxide sprayed and heated by the mist producing device 61 shown in FIG. 10.

This mist producing device 61 is provided with a hydrogen peroxide supply unit 62 as two-fluid spray for supplying solution of the hydrogen peroxide, in form of drops, as sterilizing agent and a vaporizer 63 for heating the sprayed mist of the hydrogen peroxide supplied from the hydrogen peroxide supply unit 62 to a temperature more than boiling point and less than undecomposed temperature thereof and then gasifying it.

The hydrogen peroxide supply unit 62 sprays the solution of the hydrogen peroxide into the vaporizer 63 by introducing the solution through a hydrogen peroxide supply path 62a and a compressed air through a compressed air supply path 62b.

The vaporizer 63 is composed of a pipe including a heater 63a interposed between inner and outer wall sections thereof, and serves to heat and vaporize the spray mist of the hydrogen peroxide sprayed into the pipe. The vaporized hydrogen peroxide gas is jetted, as condensed mist α toward the opening of the neck portion 1a of the bottle 1 through a spray nozzle 59.

The bottle 1 is conveyed around the wheel 58b with the neck portion 1a being directed upward, and the lower end of the spray tube 59 is opened toward the neck portion 1a of the bottle 1 at the portion above the bottle travelling (conveying) path. The condensed mist α of the hydrogen peroxide supplied into the spray tube 59 is continuously blown toward the bottle neck portion 1a through the nozzle hole formed to the lower end of the spray tube 59. The thus blown condensed mist α flows into the bottle 1 from the neck portion 1a of the travelling bottle 1 and sterilizes the inner surface of the bottle 1, and the other condensed mist α of the hydrogen peroxide flows outside of the bottle 1 so as to sterilize the outer surface of the bottle 1. At this instance, since the bottle 1 travels in the tunnel 60, the condensed mist α can be uniformly supplied to the outer surface of the bottle 1.

As shown in FIG. 2, an air rinse section 96 for the bottle 1 is connected to the sterilization section 9 for the bottle 1. This air rinse section 96 is entirely covered with a chamber 96a.

In the chamber 96a, wheel row coupled with the final end wheel 58b as the travelling means for the bottle 1 on the sterilization section side is provided, as shown in FIG. 2. More specifically, this wheel row includes four wheels 58c, 58d, 58f and 92a, and a bottle travelling path is formed around the outer peripheries of these wheels. Further, around these wheels 58d, 58d, 58e and 92a, grippers 28 similar to the gripper 28 shown in FIG. 7 are arranged.

The grippers 28 swivel around the respective wheels 58c, 58d, 58e and 92a with the neck portions 1a of the bottles 1 being gripped and then transfer the bottles 1 from the start end wheel 58c to the final end wheel 92a subsequently. According to such motion, the good bottles after the inspection continuously travel on the travelling path from the final end wheel 58b in the sterilization section 9 to the final end wheel 92a in the air rinse section 96. Since each of the grippers 28 grips the neck portion 1a of the bottle 1 during the travelling thereof by the clamp pieces 28a and 28b, the bottle 1 is travelled in the vertically suspended state.

Air rinse means for cleaning the bottle 1 by supplying aseptic heated air or normal temperature air to the bottle 1 is further disposed around an intermediate wheel 58c in the next stage contacting to the afore-mentioned intermediate wheel 58b from the downstream side thereof.

Figure 3M:
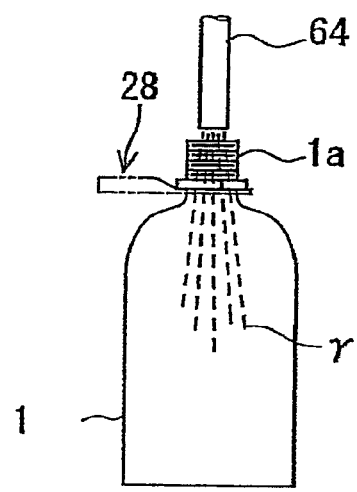
FIG. 3M is a view representing a bottle air-rinsing process.
Figure 11:
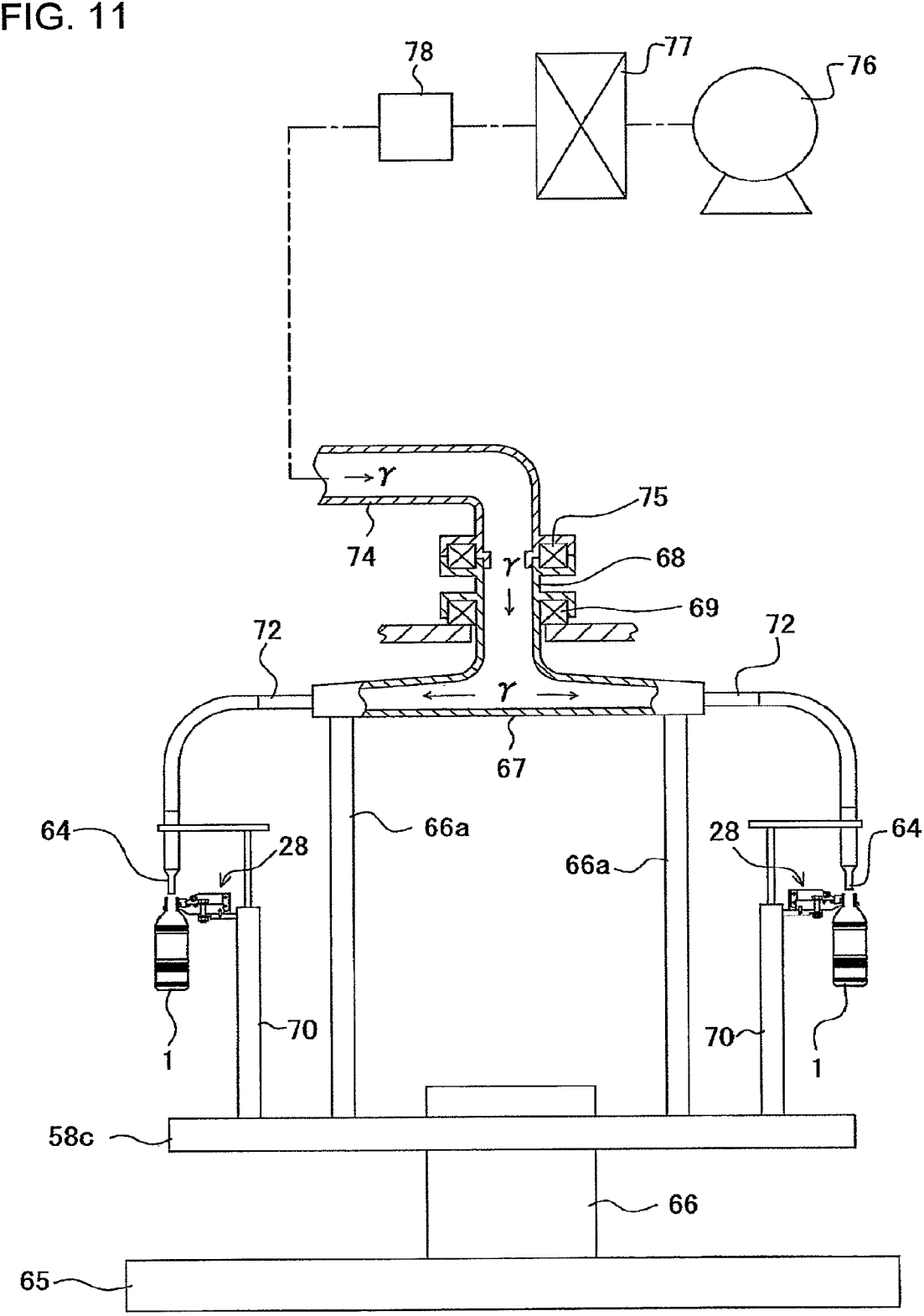
FIG. 11 is a front view of an air-rinse device which is partially cut away.

This air rinse means is provided with a nozzle 64 for jetting an aseptic air γ or normal temperature air as shown in FIG. 3M and FIG. 11.

As shown in FIG. 11, the wheel 58c rotated by the power from a predetermined drive source is mounted horizontally to a swivelling shaft 66 standing upward from the machine table 65. A column 66a extends upward from the surface of the wheel 58c, and a manifold 67 into which the heated air γ flows is fixed to the upper end portion of the column 66. A conduit 68 extends upward on a line extending from the axis of the swivelling shaft 66 at the upper central portion of the manifold 67, and the conduit 68 is held through a bearing 69 to a frame member of the chamber 9a connected to the machine table 65. Accordingly, the manifold 67 is rotatable around the swivelling shaft 66 integrally with the wheel 58c.

In addition, another column 70 extends upward from the surface of the wheel 58c, and the gripper 28 of the bottle 1 is attached to the upper portion of the column 70. A plurality of such columns 70 and grippers 28 are arranged around the wheel 58c at predetermined pitches, respectively. These grippers 28 are coupled with the wheel 58c through the columns 70 so as to be rotatable in accordance with the rotation of the wheel 58c.

These grippers 28 have substantially the same structures as those shown in FIG. 4. Further, in a case when any inconvenience is caused to the mist generating device 61 of the sterilization section 9 or like and a bottle 1 defective in sterilization effect is caused, a mechanism similar to the discharge means shown in FIGS. 8 and 9 for removing the defective bottle from the travelling path may be disposed. In FIG. 2, reference numeral 71 denotes a shooter for dropping the bottle 1 defective in sterilization effect to be removed from the bottle travelling path.

Heated air supply tubes 72 for supplying the heated air γ extend from a portion around the manifold 67 toward the grippers 28, respectively, and the nozzles 64 are mounted to the front end portions of the supply tubes 72. The nozzles 64 are fixed to the columns 70 and the nozzle holes formed to the front ends of the nozzles 64 are directed to the openings of the neck portions 1a of the bottles 1 held by the grippers 28. According to this arrangement, when the wheel 58c is rotated, the nozzle 64 is also rotated around with the swivelling shaft 66 together with the bottle 1 held by the gripper 28 so as to blow the heated air γ into the bottle 1.

Another stationary conduit 74 is connected to the upper end portion of the conduit 68 of the manifold 67 through a seal member 75. The conduit 68 is rotated integrally with the manifold 67 with respect to the conduit 74, and the seal member 75 prevents the heated air γ from leaking through the connection portion between both the conduits 68 and 75.

Furthermore, a hot air supply device composed of a blower 76, an ultra low penetration air (ULPA) filter 77 and an electric heater 78 is disposed on the upstream side of the conduit 75. The air blown from the blower 76 is cleaned by the ULPA filter 77, heated by the electric heater 78 to a predetermined temperature, and fed into the conduit 74 as the heated air γ. This heated air γ is an aseptic air, which was heated, for example, to a temperature of more than 100° C. The heated air γ then reaches the manifold 67 and blows outward into the bottles 1 through the nozzles 64 of the heated air supply tubes 72, respectively, or blows outside the bottles 1.

A tube (pipe) line extending from the conduit 74 to the nozzle 64 through the manifold 67 is formed to have a length as short as possible, and accordingly, the heated air γ can reach the bottle 1 without being condensed.

When the heated air γ is blown into the bottle 1 from the nozzle 64, the heated air γ uniformly contacts to the entire inner surface of the bottle 1 and removes extra amount of the hydrogen peroxide blown from the spray tube 59.

Further, it may be desired that the heated air γ is blown for a time during which the condensed mist α of the hydrogen peroxide floating in the inner space of the bottle 1 can be entirely exhausted. In a case where the temperature of the heated air γ is more than a resisting temperature for the bottle 1, if the blowing time is so long, the bottle 1 is heated to a temperature over the resisting temperature, which may result in deformation of the bottle. Thus, in such case, a caution should be paid.

Furthermore, as occasion demands, it may be possible to gasify the hydrogen peroxide by mixing the condensed mist α of low density hydrogen peroxide to aseptic air of normal temperature in place of the heated air γ and to supply the gasified hydrogen peroxide so as not to be condensed.

As mentioned above, by supplying the sterilized heated air γ into the bottle 1 and performing the air rinse treatment, the bottle 1 can be heated from the inner surface thereof, and the sterilizing effect by the condensed mist α of the hydrogen peroxide can be enhanced.

In the illustrated embodiment of the present invention, although the nozzle 64 serves to blow the heated air γ into the bottle 1 from the outside of the bottle 1, the nozzle 64 may be disposed to be vertically movable to be invaded into the bottle 1 when the heated air γ is blown into the bottle 1.

The travelling speed of at least the gripper 28 arranged at a portion between the start end wheel 36a of the inspection section 8 to the final end wheel 92a in the sterilization section 9 is controlled to a speed so that the heat remaining in the bottle at the bottle forming period in the molding section 7 is maintained to an extent necessary for the sterilization of the bottle 1 in the sterilization section 9.

That is, as shown in FIG. 2, a servo-motor S1 is disposed to the inspection section 8 to be driven so as to dynamically interlock the whole wheels 36a, 36b and 36c in the inspection section 8, and a servo-motor S2 is also disposed to the sterilization section 9 and the air rinse section 96 to be driven so as to dynamically interlock the whole wheels 58a, 58b, 58c, 58d, 58e and 92a in the sterilization section 8 and the air rinse section 9. By controlling these servo-motors S1 and S2, the travelling speed of the gripper 28 is regulated, and as a result, the bottle 1 gripped by the gripper is conveyed to a portion directly below the spray tube 59 in a state that the remaining heat in the bottle 1 at the bottle molding time is maintained to an extent necessary for the sterilization in the sterilization section 9. Further, the bottle 1 into which the condensed mist α of the hydrogen peroxide is blown from the spray tube 59 in the sterilization section 9 promptly reaches the air rinse section 96.

Further, it may be desired that the temperature of the bottle 1 directly below the spray tube 59 is maintained to be more than 50° C. for properly attaining the sterilization effect by the condensed mist α of the hydrogen peroxide. Especially, the bottle neck portion 1a, the thickened portion such as bottle bottom portion, and a portion, such as bottle bottom portion, to which it is hard for the condensed mist to reach, are portions hard to be sterilized. However, for the bottle 1 just after being molded, these portions are in the highly heated state, so that preferably high sterilization effect can be attained by the small amount of condensed mist α.

That is, according to the experiment performed by the inventors of the present application, it was found that the density of the hydrogen peroxide condensed on the surface of the bottle 1 becomes higher as the temperature of the bottle 1 becomes high. This is considered that the hydrogen peroxide has a boiling point higher than that of water. More concretely, in the cases of the bottle temperatures of 50° C., 65° C. and 80° C., the densities (weight %) of the hydrogen peroxide adhering to the surface of the bottle 1 were about 70%, 80% and 90%. Since the density of the hydrogen peroxide adhering to the sterilizing agent (hydrogen peroxide) on the surface of the bottle increases in addition to the increased temperature, the bottle can be sterilized by the small amount of hydrogen peroxide.

In the beverage filling apparatus of the present embodiment, there is provided positive pressure creating means for creating positive pressure in the inspection section 8 more than pressures in the molding section 7 and the sterilization section 9.

That is, as shown in FIG. 12, an atmosphere shutoff chamber 79 is disposed between the chamber 8a of the inspection section 8 and the chamber 9a of the sterilization section 9. In addition, a partition wall 35 is also disposed between the chamber 7a of the molding section 7 and the chamber 8a of the inspection section 8, and the partition wall 35 is formed with a bottle passing hole 35a through which the bottle 1 can pass. Partition walls 80 and 81 of the structure similar to that of the partition wall 35 are disposed, respectively between the chamber 8a of the inspection section 8 and the atmosphere shutoff chamber 79 and between the atmosphere shutoff chamber 79 and the chamber 9a of the sterilization section 8. Furthermore, a partition wall 82 of the structure similar to that of the above mentioned partition wall is disposed so as to separate the portion at which the condensed mist α of the hydrogen peroxide is sprayed from the spray tube 59 from the portion at which a hydrogen peroxide gas β is jetted.

An air supply duct 83 is connected to the chamber 8a of the inspection section 8 as air supply means for supplying the cleaned air, and an air supply blower 84, a filter 85 and a heater 97 are provided for this air supply duct 83. The air is heated by the heater 97, and the heated air contacts the bottle 1 travelling in the chamber 8a, so that the bottle 1 is protected from being cooled, or is further heated. Incidentally, the heating by the heater 97 may be eliminated if the remaining heat at the bottle molding time does not substantially effect the sterilization in the sterilization section 9.

By blowing the cleaned air into the chamber 8a of the inspection section 8 by the air supply means, a positive pressure state such as of 3 Pa higher than atmospheric pressure is created in the chamber 8a of the inspection section 8.

An air exhaust duct 86, as air exhaust means, is coupled with the atmosphere shutoff chamber 79, and an air exhaust blower 87 and a filter 88 are provided for this air exhaust duct 86. Another air exhaust duct 89 may be coupled with a portion adjacent to the atmosphere shutoff chamber 79 in the chamber 9a of the sterilization section 9, as occasion demands, and this air exhaust duct 89 is connected to the exhaust duct 86 coupled with the atmosphere shutoff chamber 79. According to the location of the air exhaust means, the interior of the atmosphere shutoff chamber 79 is maintained at a pressure of 0 Pa (zero Pa) substantially equal to the atmospheric pressure.

Furthermore, an air supply duct as supply means, not shown, for supplying the cleaned air is coupled with a chamber 10a of a filling section which will be mentioned herein later, and the air supply blower and the filter are provided for this air supply duct. By the location of such air supply means, the cleaned air is blown into the chamber 10a of the filling section 10 at a pressure of approximately 20 to 100 Pa. This cleaned air flows into the chamber 9a of the sterilization section 9 through the chamber 96a of the air rinse section 96, and creates the positive pressure (about 10 Pa) state in the chamber 9a of the sterilization section 9. Thereafter, the cleaned air flows outward of the chamber 9a of the sterilization section 9 and the atmosphere shutoff chamber 79 through the duct 89 of the chamber 9a and the duct 86 of the chamber 79, respectively.

Further, the interior of the chamber 7a of the molding section 7 is maintained at 0 Pa approximately equal to the atmospheric pressure.

The partition wall 81 disposed between the atmosphere shutoff chamber 79 and the chamber 9a of the sterilization section 9 is formed with a bottle passing hole 81a and an air nozzle 90 for shutting off the passing hole 81a with air curtain may be disposed as occasion demands.

By the location of such positive pressure creating means, the condensed mist α and the gas β of the hydrogen peroxide flowing into the chamber 9a of the sterilization section 9 are exhausted externally of the chamber 9a through the duct 89, and on the other hand, the cleaned air introduced into the chamber 8a of the inspection section 8 flows toward the chamber 7a of the molding section 7 and the atmosphere shutoff chamber 79, thus preventing contaminated air and air containing the hydrogen peroxide from entering the chamber 8a of the inspection section 8. Furthermore, even if the air is sucked into the chamber 8a of the inspection section 8 from the chamber 7a of the molding section 7 in accordance with the travelling of the bottle 1, such air is prevented from entering the chamber 9a of the sterilization section 9 by the exhaust gas from the atmosphere shutoff chamber 79, thus appropriately preventing the contamination in the sterilization section.

As shown in FIG. 2, the filling section 10 is coupled with the air rinse section 96 and entirely covered with a chamber 10a. A partition wall, not shown, is disposed between the chamber 96a of the air rinse section 96 and the filling section 10, and this partition wall is formed with a bottle passing hole through which the bottle 1 passes.

The chamber 10a of the beverage filling section 10 is connected, as shown in FIG. 2, to a wheel row coupled with the final end wheel 92a as the bottle travelling path on the air rinse section side.

More specifically, this wheel row includes four wheels 94c, 94d, 94e and 94f, and a bottle travelling path is formed to the outer peripheries of these four wheels. Grippers 28 similar to those shown in FIG. 4 are arranged around the wheels 94c, 94d, 94e and 94f, respectively.

Inside the chamber 10a of the beverage filling section 10, the bottles 1 are transferred from the start end wheel 94c to the final end wheel 94f while grippers 28 turning around these wheels with the bottle neck portions 1a being held. According to such motion, the bottles 1 can be continuously travelled in the beverage filling section 10 from the start end wheel 94c to the final end wheel 94f. Each of the grippers 28 grips the neck portion 1a of the bottle 1 by its clamp pieces 28a and 28b in the vertically suspended attitude of the bottle 1 during the bottle travelling.

Figure 3N:
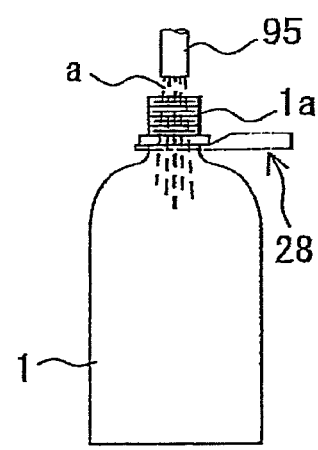
FIG. 3N is a view representing a beverage filling process.

A beverage filling machine is placed to a predetermined position around the start end wheel 94c, having a larger diameter, in the chamber 10a of the beverage filling section 10. As shown in FIG. 3N, the beverage "a", which was preliminarily subjected to the sterilization process, fills the bottle 1 through the nozzle 95 of the beverage filling machine. This nozzle 95 is travelled in synchronous with the travelling of the bottle 1, and a constant amount of the beverage "a" fills the bottle 1 during the parallel travelling with the bottle 1.

Figure 3O:
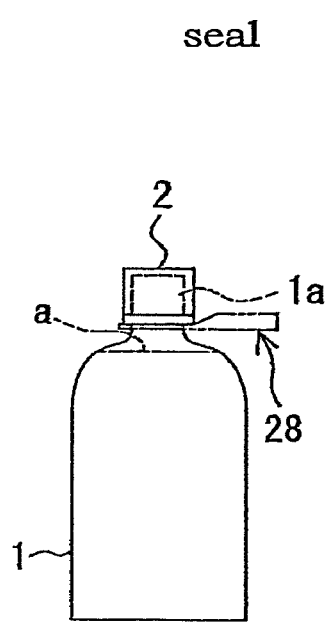
FIG. 3O is a view representing a sealing process by means of capping.

A capper is arranged to a predetermined position around the intermediate wheel 94e downstream side of the beverage filling machine. As shown in FIG. 3O, the cap 2 is mounted to the neck portion 1a of the bottle 1 by means of this capper, thus sealing the bottle 1.

The bottle 1 filled up with the beverage "a" and then sealed by the cap 2 is released from the gripper 28 of the final end wheel 94f and discharged outside of the beverage filling machine through an outlet formed to the chamber 10a.

Further, since these beverage filling machine and the capper are known ones, the detailed explanation thereof is omitted herein.

Furthermore, as shown in FIG. 2, the beverage filling section 10 is provided with two servo-motors S5 and S6 driven so as to be dynamically interlocked in a predetermined combination of the wheels 94c, 94d, 94e and 94f inside the beverage filling section 10. The first serve-motor S5 of these two servo-motors serves to drive the start end wheel 94c around which the beverage filling machine is disposed, and the second servo-motor S6 serves to drive the wheels 94d, 94e and 94f disposed downstream side of the intermediate wheel 94c.

According to the arrangement described above, even if the wheels and the grippers in the respective sections of the inspection section 8, the sterilization section 9, the air rinse section 96 and the beverage filling section 10 have the structures different from each other, the synchronous driving of the grippers can be achieved by controlling the servo-motors S1, S2, S5 and S6, and hence, the bottles 1 can be smoothly continuously travelled into the beverage filling section 10 from the molding section 7.

Further, in the described embodiment, although the molding section 7 is driven by a known electric motor, not shown, the wheels and the turntable in the molding section 7 may be driven by a servo-motor.

Hereunder, the operation of the beverage filling apparatus of the structures mentioned above will be described.

(1) First, a preform 6 shown in FIG. 3A is prepared. The preform 6 is subjected to the injection molding, and thereafter, is fed to a preform supply machine 11 of the beverage filling apparatus of the present invention. The preform 6 is fed into the molding section 7 by means of conveyer 12 of the preform supply machine 11.

(2) The preform conveyed in a vertically standing state by the conveyer 12 as shown in FIG. 3A is transferred to the gripper of the start end wheel 13a continuously rotating in the molding section 7, and is then inverted in attitude by the gripper of the intermediate wheel 13b.

The inverted preform 6 is covered to the mandrel 17 of the first turn table 14a from the neck portion 1a, as shown in FIG. 3B.

The mandrel 17 covered with the preform 6 is, as shown in FIG. 3C, travelled, while revolving, inside the heating chamber 16, and the preform 6 is also continuously travelled, while revolving with the mandrel 17, in the heating chamber 16. Accordingly, the preform 6 can be uniformly heated to a temperature capable of being subjected to the blow-forming.

(3) The heated preform 6 is clamped, as shown in FIG. 3D, by the blow-forming molds 18, and air is blown into the preform 6 through the blow nozzle 19 penetrating the mandrel 17 to thereby form the bottle 1 in the mold 18.

The molded bottle 1 is taken out of the mold 18 together with the mandrel 17 by opening the mold halves, and as shown in FIG. 3E, the bottle 1 is conveyed to the first turntable 14*a* in the inverted state through the sixth turntable 14*f*.

(4) The bottle 1 held by the mandrel 17 at the first turntable 14*a* is gripped as shown in FIG. 3F, by a gripping member 98 of the start end wheel 19*a* and inverted so as to take the normal vertical attitude. In this operation, the gripping member 98 grips a portion of the bottle 1 above the support ring 5 of the neck portion 1*a*. Subsequently, the bottle 1 is received by the gripper 28 of the final end wheel 19*b* as shown in FIG. 4. The gripper 28 grips, at this time, the portion lower than the support ring 5 of the bottle neck portion 1*a* as shown in FIG. 6.

(5) Then, the gripper 37 of the start end wheel 36*a* of the inspection section 8 grips a portion upper than the support ring 5 of the bottle neck portion 1*a* and receives the bottle 1 from the final end wheel 19*b* of the molding section 7, and the bottle 1 swivels while being held by the gripper 37.

During this swivelling operation, as shown in FIG. 3G, the shell portion of the bottle 1 is inspected by the bottle shell portion inspection means. In this inspection, the image of the shell portion of the bottle picked up by the camera 45 is processed by the image processing device, not shown, and it is discriminated whether any abnormality such as injury, foreign material, discoloration or like exists.

(6) The bottle 1 is then transferred from the gripper 37 of the start end wheel 36*a* to the gripper 28 of the intermediate wheel 36*b*, and the gripper 28 of the intermediate wheel 36*b* grips the lower side of the support ring 5 of the bottle neck portion 1*a* and swivels as shown in FIG. 3H and FIG. 6.

During this swivelling motion, as shown in FIG. 3H, the temperature of the bottle 1 is detected by the temperature sensor 46 of the temperature detecting means. In this temperature detection, if the detected temperature does not reach 50° C., it is discriminated that this bottle 1 is a defective product.

(7) Subsequently, as shown in FIG. 3I, the surface condition of the support ring 5 of the bottle 1 is inspected by the support ring inspection means. In this inspection, the image of the upper face of the support ring 5 picked up by the camera 48 is processed by the image processing device, not shown, and it is discriminated whether any abnormality such as injury, foreign material, discoloration or like exists.

(8) Subsequent to the support ring inspection, as shown in FIG. 3J, the surface condition of the upper face 1*d* of the bottle neck portion 1*a* is inspected by the bottle neck portion upper face inspection means. In this inspection, the image of the upper face 1*d* of the bottle neck portion 1*a* picked up by the camera 50 is processed by the image processing device, not shown, and it is discriminated whether any abnormality such as injury, foreign material, discoloration or like exists.

(9) Subsequent to the bottle neck portion upper face inspection, as shown in FIG. 3K, the bottom condition of the bottle 1 is inspected by the bottle bottom portion inspection means. In this inspection, the image of the bottom portion of the bottle 1 picked up by the camera 52 is processed by the image processing device, not shown, and it is discriminated whether any abnormality such as injury, foreign material, discoloration or like exists.

(10) The bottle 1 subjected to the above respective inspections is held by the gripper 28, shown in FIG. 8, of the final end wheel 36*c* of the inspection section 8. In an event that an abnormal signal informing an occurrence of an abnormality is generated from any one of the respective inspection means, as shown in FIG. 9, the gripper releasing mechanism is operated, and a pair of clamping pieces 28*a* and 28*b* of the gripper 28 is moved from the closed position shown with two-dotted-chain line to the opened position shown with solid line to thereby release the defective bottle 1.

According to such operation, the defective bottles 1, to which any abnormal condition is caused to the shell portion, the bottom portion, the neck upper face 1*d* and the support ring 5 of the bottle 1, are discharged (rejected) from the bottle travelling path, and the bottles 1, which are not subjected to sufficient sterilization effect by the hydrogen peroxide even if heated in the subsequent sterilization process, are also discharged (rejected) from the travelling path.

On the other hand, the good bottles 1 pass through the bottle discharging means, because the movable cam 53*a* is held to the position shown in FIG. 9A, and move toward the sterilization section 9.

(11) The good bottle 1 is transferred from the gripper 28 of the final end wheel 36*c* of the inspection section 8 to the gripper 28 of the start end wheel 58*a* of the sterilization section 9, and then, transferred to the gripper of the wheel disposed downstream side, thus being continuously travelled.

When the good bottle 1 is travelled around the intermediate wheel 58*b* while being held by the gripper 28, the good bottle 1 travels directly below the spray tube 59 as shown in FIG. 3L. Accordingly, the condensed mist α of the hydrogen peroxide jetted from the spray tube 59 is brown against the bottle 1 to thereby sterilize the inner and outer surfaces of the bottle 1. As mentioned above, since the good bottles 1 having proper remaining heat are only travelled, these bottles 1 can be properly sterilized by the condensed mist α of the hydrogen peroxide, and thereafter, are travelled toward the downstream side.

(12) The bottle 1 blown with the condensed mist α of the hydrogen peroxide in the sterilization section 9 is travelled around the intermediate wheel 58*c* while being held by the gripper 28. During this travelling, the heated air γ is brown through the nozzle 64 as shown in FIG. 3M. Accordingly, the inner and outer surfaces of the bottle 1 can be cleaned through the air rinse process to thereby remove the excessive hydrogen peroxide adhering to the inner and outer surfaces of the bottle 1.

Further, it is desired that the bottle 1 blown with the condensed mist α of the hydrogen peroxide from the spray tube 59 at the sterilization section 9 reaches inside the air rinse section 96 within 0.1 to 5.0 second, and in a case of less than 0.5 second, sufficient sterilization effect will not be expected because of too short sterilizing time, and on the contrary, in a case of more than 5.0 seconds, the hydrogen peroxide will intrude inside the inner layer of the PET wall, and the remaining amount of the hydrogen peroxide will increase, which will require location of such aseptic water rinse section 91 as mentioned hereinafter with respect to a second embodiment.

Test result exhibiting ground of the above matter will be shown hereunder.

The inventors of the present application measured the sterilization effects and remaining hydrogen peroxide density with respect to B. subtilis spore by using a PET bottle of 500 mL volume. The measured results are shown in the following table (Table 1).

TABLE 1

| NO. | From hydrogen peroxide spray to air-rinse | Log Reduction (LR) | | |
|---|---|---|---|---|
| | | 0.5 sec | 2 sec | 5 sec |
| 1 | Remaining hydrogen peroxide | 0.3 ppm | 0.4 ppm | 0.9 ppm |
| | Judgment | ○ | ○ | x |
| 2 | Log reduction | 4.5 Log | 6 Log | >6 Log |
| | Judgment | x | ○ | ○ |
| | Total judgment | x | ○ | x |

Evaluation method to the measurement was as follows.

Sterilization Effects (Log Reduction)=Log(Number of Adhering Bacteria/Number of Survived Bacteria)

Index Bacteria: *B. subtilis* var. *niger* ATCC9372

Remaining Hydrogen Peroxide Density Measurement: Measured by Oxygen Electrode Method Sterilizing Process: A bottle was taken out from a blow injection mold, condensed mist of hydrogen peroxide was sprayed to the bottle, and air rinse treatment was performed.

The hydrogen peroxide was supplied by 30 μL. The condensed mist of the hydrogen peroxide was sprayed within 30 seconds after the separation of the bottle from the mold. This is because the high sterilization effect by the hydrogen peroxide is obtained as high as the temperature of the bottle after the separation from the mold, and if the heat escapes from the bottle and the bottle is cooled, the hydrogen peroxide is condensed on the PET wall surface of the bottle and is likely adsorbed into the PET inner layer.

As is apparent from the Table 1, after 2 seconds from the spraying of the hydrogen peroxide, when the air rinsing process is initiated, the remaining hydrogen peroxide becomes less than 0.5 ppm and the sterilization effect becomes more than 6 Log.

(13) As shown in FIG. 12, the positive pressure creating means is arranged on the way of the travelling path of the bottle 1 which is travelled from the molding section 7 to the sterilization section 9, and accordingly, the excessive amount of the mist α of the hydrogen peroxide flowing into the chamber 9a of the sterilization section 9 is discharged outside of the chamber 9a through the ducts 86 and 89, and on the other hand, the cleaned air flowing into the chamber 8a of the inspection section 8 flows toward the chamber 7a of the molding section 7 and the atmosphere shutoff chamber 79 to thereby prevent the contaminated air or air containing hydrogen peroxide from flowing into the chamber 8a of the inspection section 8.

Furthermore, even if the air is pulled into the chamber 8a of the inspection section 8 from the chamber 7a of the molding section 7 in accordance with the travelling of the bottle 1, this air is prevented from entering into the chamber 9a of the sterilization section 9 by the exhaust from the atmosphere shutoff chamber 79, thus effectively preventing the contamination of the interior of the sterilization section 9.

(14) During the conveyance of the bottle 1 toward the downstream side of the sterilization section 9 through the inspection section 8, in occurrence of an event that any abnormality is caused on the molding section 7 and the wheel row on the molding section side emergently stops in operation, as shown in FIG. 7, the piston rod 42a of the piston-cylinder assembly 42 is contracted to thereby open the paired clamp pieces 37a, 37b in the closed state by about 180 degrees.

Accordingly, the interference between the gripper 28 mounted to the final end wheel 19b of the molding section 7 and the gripper 37 mounted to the start end wheel 36a of the inspection section 8 can be effectively prevented.

Furthermore, since the start end wheel 36a and the following wheel row are being continuously rotated, the bottle 1 introduced into the inspection section 8 is continuously travelled downstream side. Accordingly, the normally formed bottle 1 is subjected to the inspection in the inspection section 8 and the bottle 1 passing through the inspection section 8 is travelled toward the sterilization section 9, thus the bottle being processed laconically. Moreover, even if the molding section 7 stops in operation, since the respective sections following the inspection section 8 can be operated, the bottle 1 can be continuously travelled through the sections following the sterilization section 9, thus preventing the excessive adhering of the hydrogen peroxide due to the stopping of the bottle in the sterilization section 9 and also preventing the insufficient sterilization due to the cooling of the bottle 1, and accordingly, the only the normal bottles 1 can be filled with beverage.

(15) The bottle 1 subjected to the air-rinsing treatment is conveyed to the beverage filling section 10, and when the bottle is travelled around the wheel 94c while being gripped by the gripper 28, as shown in FIG. 3N, a predetermined amount of the beverage "a" from the beverage filling machine is supplied into the bottle 1.

(16) The bottle 1 filled with the beverage "a" is travelled around the wheel 94e while being gripped by the gripper 28, and at this period, as shown in FIG. 3O, the cap 2 is applied to the bottle neck portion 1a by the capper. According to this operation, the bottle 1 is sealed as a beverage packaging bottle.

The bottle 1 as the beverage packaging bottle is then fed out externally from the beverage filling apparatus.

Second Embodiment

A second embodiment of the beverage filling apparatus for filling the bottle 1 with the beverage will be described hereunder.

Figure 13:
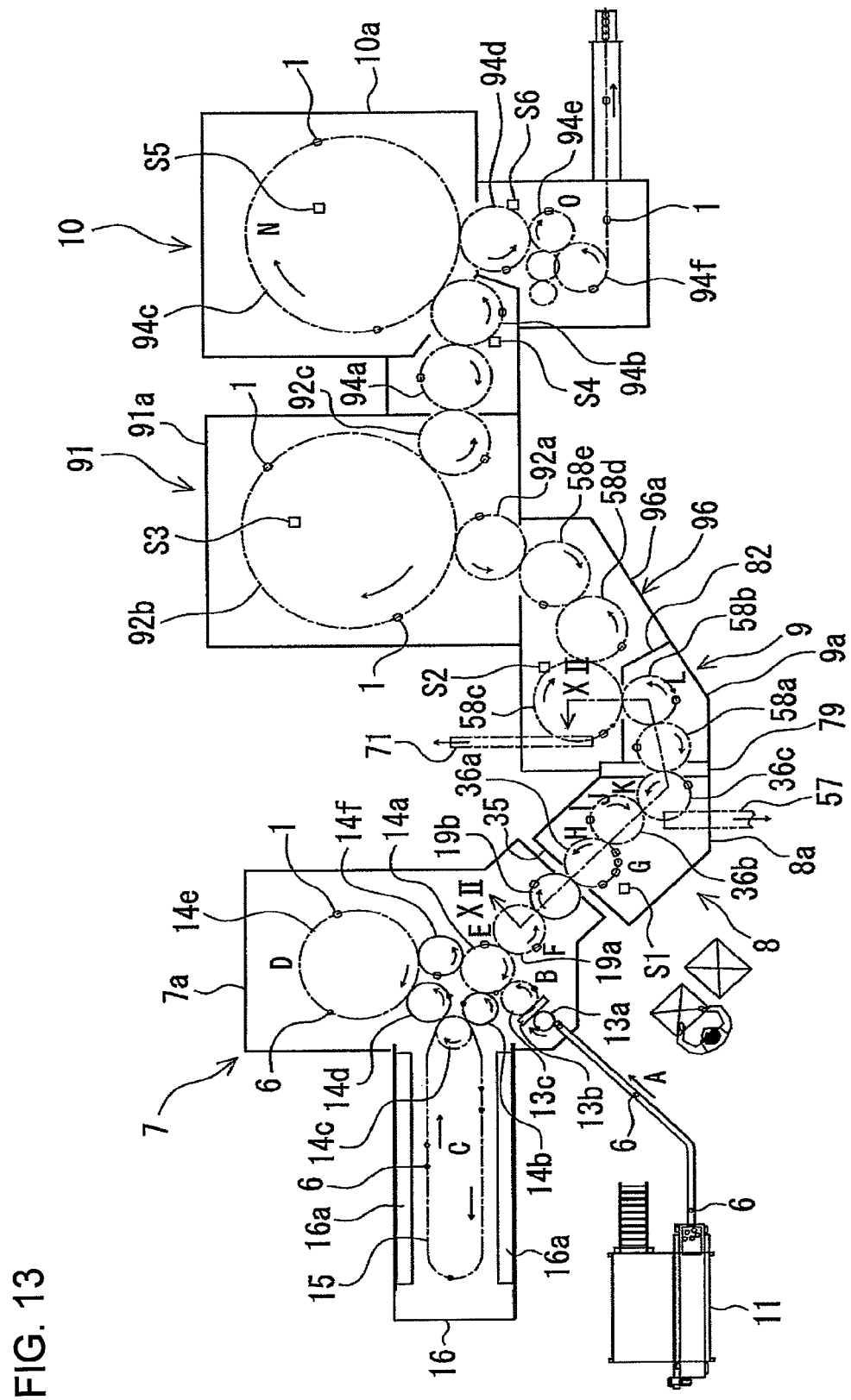
FIG. 13 is a plan view representing a beverage filling apparatus according to a second embodiment of the present invention.

As shown in FIG. 13, the beverage filling apparatus of this second embodiment is provided with the bottle molding section 7, the inspection section 8 for inspecting the molded bottle 1, the bottle sterilization section 9, the bottle air rinse section 96, the bottle aseptic water rinse section 91, and a beverage filling section 10 for filling the bottle 1 with the beverage "a" and then sealing the bottle 1.

The structure or arrangement ranging from the molding section 7 to the sterilization section 9 are substantially the same as that in the first embodiment, so that the duplicated explanation is omitted herein.

As shown in FIG. 13, the air rinse section 96 for the bottle 1 is coupled with the sterilization section 9, and the air rinse section 96 is entirely covered with the chamber 96a.

A wheel row coupled with the final end wheel 58b, as bottle travelling means, on the side of the sterilization section 9 for the bottle 1 is connected to the inside of the chamber 96a of the air rinse section 96, as shown in FIG. 13. More specifically, this wheel row includes three wheels 58c, 58d and 58e, around which a bottle travelling path is formed. Further, grippers 28 similar to the grippers 28 shown in FIG. 4 are also arranged around these wheels 58c, 58d and 58e.

The grippers 28 grip the neck portions 1a of the respective bottles 1, and in this state, the bottles 1 are turned around the respective wheels 58c, 58d and 58e and then transferred from the start end wheel 58c to the final end wheel 58e. Accordingly, the good bottles 1 after the inspection are travelled continuously along the travelling path from the final end wheel 36b in the sterilization section 9 to the final end wheel 58e in the air rinse section 96. Since the gripper 28 grips the neck portion 1a of the bottle 1, the bottle 1 is travelled in the vertically suspended attitude.

Air rinse means for cleaning the bottle 1 by supplying the heated air γ mixed with the hydrogen peroxide gas β as the sterilizing agent is disposed around the start end wheel 58c.

Figure 14A:
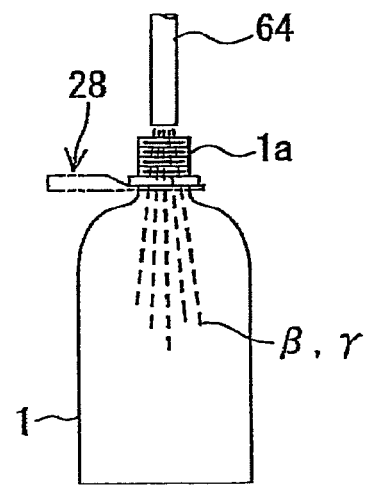
FIG. 14A is a view representing an air-rinsing process performed by the beverage filling apparatus shown in FIG. 13.
Figure 17:
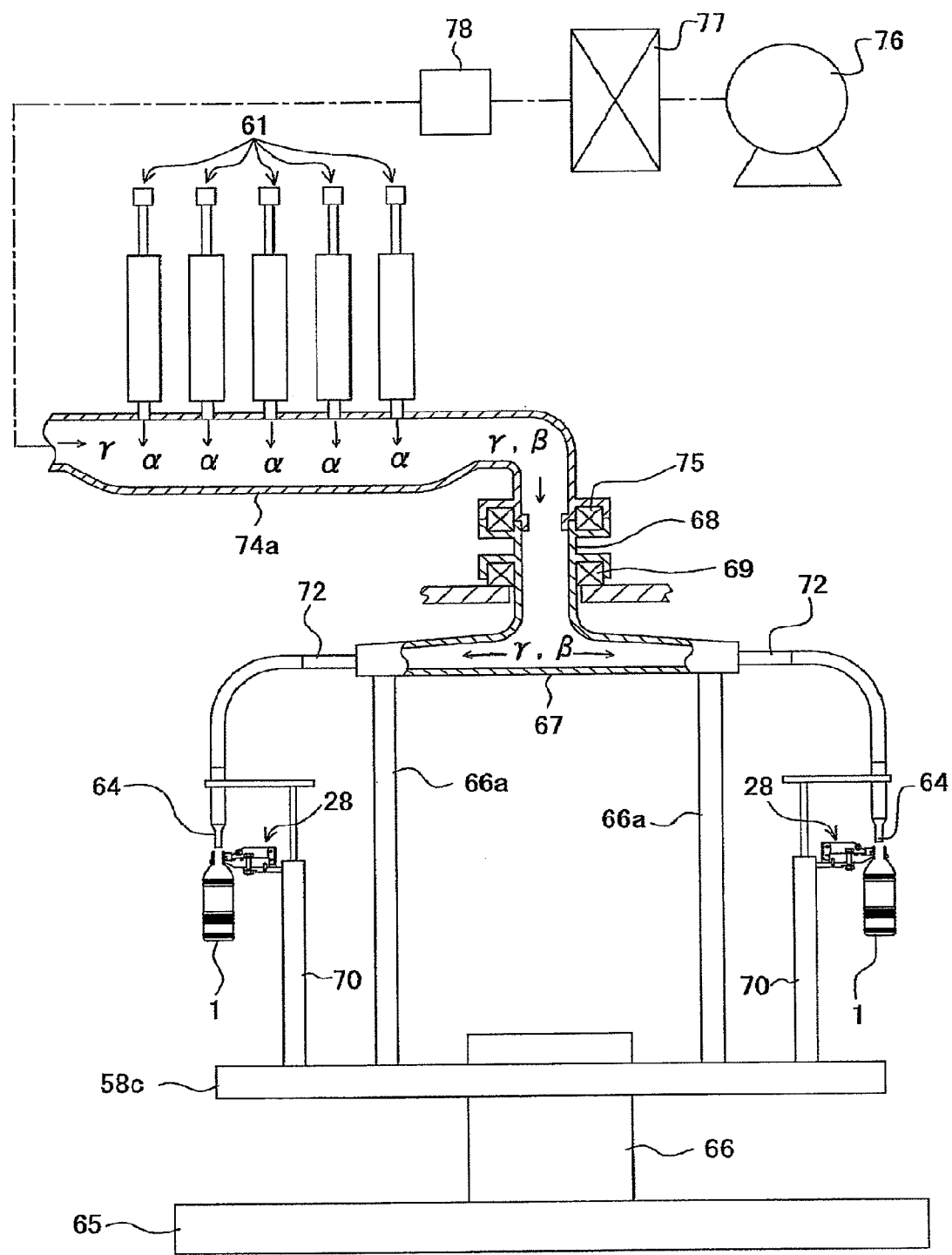
FIG. 17 is a plan view of the air-rinse device, partially cut away, of the beverage filling apparatus shown in FIG. 13.

This air rinse means is provided with a nozzle 64 discharging the heated air γ mixed with the hydrogen peroxide gas β as shown in FIG. 14A and FIG. 17.

As shown in FIG. 17, the wheel 58c rotating by the power from a predetermined power source is horizontally mounted to the swivelling shaft 66 standing from the machine table 65. Columns 66a extend upward from the surface of the wheel 58c and a manifold 67 into which the heated air γ mixed with the hydrogen peroxide gas β is fed is fixed to the upper end portions of the columns 66a. A conduit 68 extends upward on an extension of an axis of the swivelling shaft 66 from the upper central portion of the manifold 67, and the conduit 68 is held by a frame member of the chamber 9a coupled with the machine table 65 through a bearing 69. Accordingly, the manifold 67 becomes rotatable around the swivelling shaft 66 integrally with the wheel 58c.

Furthermore, other columns 70 extend upward from the surface of the wheel 58c, and grippers 28 are mounted to the upper end portions of the respective columns 70, and a plurality of columns 70 and grippers 28 are disposed around the wheel 58c at predetermined pitches. Since the grippers 28 are coupled with the wheel 58c through the columns 70, the grippers 28 are rotated together with the rotation of the wheel 58c.

These grippers 28 have substantially the same structures as those shown in FIG. 4.

Furthermore, in an event that any inconvenient matter is caused, for example, to the mist generation device 61 of the sterilization section 9 and an insufficiently sterilized bottle 1 is produced, such bottle 1 is discharged or rejected from the travelling path by a mechanism as discharging means of the structure similar to that shown in FIGS. 8 and 9. Further, in FIG. 2, reference numeral 71 denotes a shooter for falling down the insufficiently sterilized bottle 1 to be discharged by the discharging means from the travelling path.

A plurality of supply tubes 72 for supplying the heated air γ mixed with the hydrogen peroxide gas β toward the respective grippers 28 extend around the manifold 67, and the nozzles 64 are formed to the distal end portions of the respective supply tubes 72. Each of the nozzles 64 is fixed to the column 70 and a nozzle opening formed to the distal end of the nozzle 64 is directed to the opening of the neck portion 1a of the bottle 1 held by the gripper 28. According to such arrangement, when the wheel 58c is rotated, the nozzle 64 is turned around the swivelling shaft 66 together with the bottle 1 held by the gripper 28 and the heated air γ mixed with the hydrogen peroxide gas β is blown into the bottle 1.

A duct 74a is connected to the upper end of the conduit 68 of the manifold 67 through a seal member 75. The conduit 68 rotates together with the manifold 67 with respect to the duct 74a, and the seal member 75 prevents the hydrogen peroxide gas β from leaking through the connecting portion between the conduit 68 and the duct 74a. A plurality of mist generating devices 61 shown in FIG. 10 is mounted to the duct 74a, and the condensed mist α of the hydrogen peroxide is supplied into the duct 74a from the respective mist generating devices 61. The number of the mist generating devices 61 to be operated will be determined in accordance with the amount of the hydrogen peroxide gas β required for the sterilization of the bottle 1.

A hot air supply device composed of a blower 76 and ultra low air filter (ULPA Filter) 77 and a heater 78 is disposed on the upstream side of the duct 74a. The air introduced through the blower 76 is cleaned by the ULPA filter 77 and then heated by the heater 78 to a predetermined temperature so as to create the hot air γ, which is then fed into a heating tube 74a. The heated air γ is an aseptic air heated to a temperature more than a dew point of the hydrogen peroxide, for example, 100° C. The heated air γ acts to gasify the condensed mist α of the hydrogen peroxide fed to the mist generation device 61 and conveys the gasified mist to the manifold 67. The heated air γ mixed with the hydrogen peroxide gas β is blown into the bottle 1 from the nozzle 64 through each of the supply tubes 72 or is blown out of the bottle 1.

A line from the duct 74a to the nozzle 64 through the manifold 67 is formed as possible as short, and because of this reason, the hydrogen peroxide gas β is not condensed and reaches the bottle 1 together with the heated air γ.

When the heated air γ mixed with the hydrogen peroxide gas β is blown into the bottle 1 from the nozzle 64, the hydrogen peroxide gas β contacts uniformly the entire inner surface of the bottle 1 to thereby promptly and smoothly sterilize the bottle inner surface.

Further, it is desirable that the density of the hydrogen peroxide gas β to be mixed into the heated air γ is 1 mg/L to 10 mg/L (L: the hydrogen peroxide gas volume in the mixed gas), and more preferably, 2 mg/L to 8 mg/L.

As mentioned above, by supplying the sterilized hydrogen peroxide gas β and the heated air γ in the bottle 1 to thereby perform the air rinse treatment, the bottle 1 is heated from the inner surface thereof, which enhances the sterilizing effect by the condensed mist α and the hydrogen peroxide gas β. In addition, for example, a bottom portion of the bottle 1, which was insufficiently sterilized by the hydrogen peroxide condensed mist α can be more sufficiently sterilized by the hydrogen peroxide gas β contained in the heated air γ.

Further, the time for blowing the heated air γ containing the hydrogen peroxide gas β will be determined within a range by which all the condensed mist α of the hydrogen peroxide floating inside the bottle 1 can be discharged and the insufficient sterilization by the condensed mist α of the hydrogen peroxide can be compensated for. In the case where the temperature of the heated air γ containing the hydrogen peroxide gas β is more than the resisting temperature of the bottle 1, there may cause a case in which the bottle 1 is heated to a temperature more than its resisting temperature and is deformed unfairly if the heated air blowing time is too long, and hence, attention should be paid. The blowing time of this heated air γ containing the hydrogen peroxide gas β may be set to 2 to 5 seconds, for example.

Furthermore, as occasion demands, in place of the heated air γ, the hydrogen peroxide is gasified by mixing the condensed mist of the low density hydrogen peroxide with sterilized air of normal temperature and such gasified hydrogen peroxide gas may be supplied to the nozzle 64 so as not to be condensed.

As mentioned above, by performing the air rinse treatment by supplying the sterilized heated air γ containing the hydrogen peroxide gas β into the bottle 1, the bottle 1 is heated from the inner surface thereof and the sterilizing effect by the hydrogen peroxide gas β contained in the heated air γ, for example, a bottom portion of the bottle 1, which was insufficiently sterilized by the hydrogen peroxide condensed mist α supplied from the spray tube 59 can be more sufficiently sterilized by the hydrogen peroxide gas β contained in the heated air γ.

In the illustrated embodiment, although the hydrogen peroxide gas β contained in the heated air γ is blown into the bottle 1 with the nozzle 64 being disposed outside the bottle 1, each nozzle 64 may be arranged to be vertically movable so that the nozzle 64 enters the bottle 1 when the hydrogen peroxide gas β contained in the heated air γ is blown into the bottle 1. Furthermore, the nozzle 64 may be inserted into the bottle 1 in the inverted attitude to thereby perform the air rinsing treatment to thereby remove foreign materials or like.

The grippers 28 disposed between the start end wheel 36a in the inspection section 8 and the final end wheel 58b in the sterilization section 9 are controlled in their travelling speeds such that the remaining heat of the bottles 1 at the bottle molding process in the molding section 7 is maintained to an extent necessary for the sterilization of the bottles 1 in the sterilization section 9.

That is, as shown in FIG. 13, the servo-motor S1 for driving all the wheels 36a, 36b, 36c in the inspection section 8 so as to be dynamically interlocked with each other is disposed in the inspection section 8, and the servo-motor S2 for driving all the wheels 58a, 58b, 58c, 58d, 58e in the sterilization section 9 and the air rinse section 96 so as to be dynamically interlocked with each other is disposed in the sterilization section 9 and the air rinse section 96.

According to the controlling of the servo-motors S1 and S2, the travelling speed of the grippers 28 are adjusted, and as a result, the bottle 1 gripped by the gripper 28, with the remaining heat at the bottle molding time being maintained to the extent necessary for the sterilization in the sterilization section 9, is conveyed directly below the spray tube 59.

Further, the bottle 1 blown with the condensed mist α of the hydrogen peroxide from the spray tube 59 at the sterilization section 9 promptly reaches the air rinse section 96.

It may be desired that the temperature of the bottle 1 directly below the spray tube 59 is maintained more than 50° C. By maintaining the temperature more than 50° C., the sterilization effect by the condensed mist α of the hydrogen peroxide can be properly achieved. Further, although it is hard to sterilize the bottle neck portion 1a, the thickened portion such as bottle bottom portion and the portions such as bottle bottom portion to which the condensed mist hardly reaches, according to the present embodiment, since in the bottle 1 immediately after the molding process, these portions are highly heated, these portions can be effectively sterilized even by a small amount of the condensed mist α.

In the beverage filling apparatus of this embodiment, there is provided positive pressure creating means for making the pressure in the inspection section 8 higher than the pressure in the molding section 7 and the sterilization section 9 as like as in the first embodiment mentioned hereinbefore. Since this positive pressure creating means has substantially the same structure as that of the first embodiment, the details thereof are omitted herein As shown in FIG. 13, an aseptic water rinse section 91 is coupled with the air rinse section 96. This aseptic water rinse section 91 is also entirely covered by a chamber 91a. A partition wall, not shown, is disposed between the chamber 91 and the chamber 9a of the sterilization section 9 and a bottle passing hole is formed to this partition wall.

A wheel row coupled with the final end wheel 58e of the bottle travelling means on the sterilization section side is connected to the chamber 91a of the aseptic water rinse section 91. More specifically, this wheel row includes three wheels 92a, 92b, 92c, around which a bottle travelling path is formed.

Figure 15A:
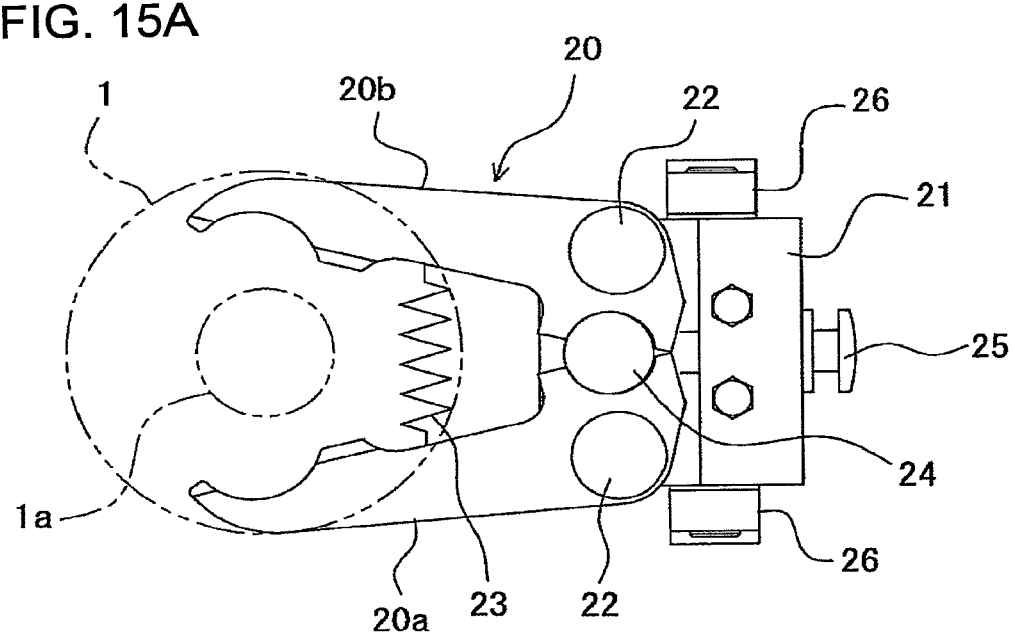
FIG. 15A is a plan view showing an opened state of a pair of clamping pieces of the gripper which inverts the bottle upside down.
Figure 15B:
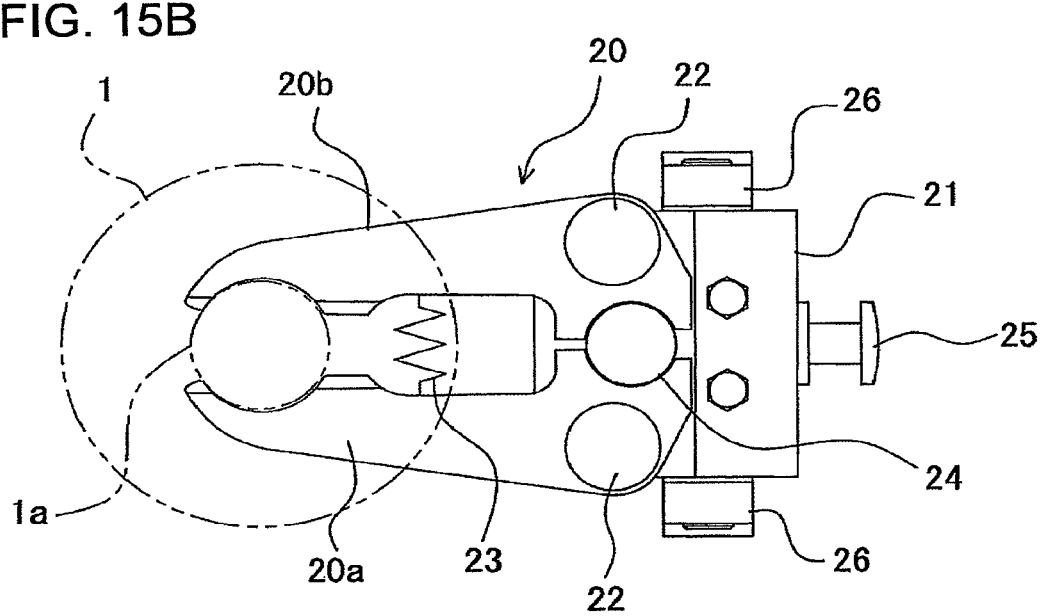
FIG. 15B is a plan view showing a closed state of a pair of clamping pieces of the gripper which inverts the bottle upside down.

Furthermore, grippers 28 similar to those shown in FIG. 4 are arranged around the start end wheel 92a and the final end wheel 92c, and a plurality of grippers 20, such as shown in FIGS. 15A and 15B, are also arranged around the intermediate wheel 92b having a larger diameter, at constant pitches.

The gripper 20 has a pair of clamp pieces 20a and 20b for clamping the neck portion 1a of the bottle 1 from the outside side thereof. The paired clamp pieces 20a, 20b are supported to the base portion 21 by means of vertical pins 22, 22 to be rotatable and always pulled in the closing direction by means of tension spring 23. According to such structure, as shown in FIG. 15B, the paired clamp pieces 20a, 20b always function to grip the neck portion 1a of the bottle 1. A column-shaped vertical shaft pin 24 is attached to the base portion 21 in a manner such that the vertical shaft pin 24 is slidable in the radial direction of the start end wheel 19a with the shaft pin 24 being fitted into recessed portions formed to root portions of the clamp pieces 20a and 20b. A cam follower 25 is coupled with the vertical shaft pin 24 also to be slidable in the radial direction of the start end wheel 19a.

Inside the intermediate wheel 92b is arranged a cam, not shown, which is engaged with the cam follower 25 so as to slide the cam follower 25 and the vertical shaft pin 24 in the radial direction of the start end wheel 19a at the predetermined position and which acts to switch the clamp pieces 20a and 20b of the gripper 20 to the opened position or closed position thereof. When the intermediate wheel 92b is rotated and the gripper 20 is moved so as to oppose to the bottle 1 gripped by the gripper 28 of the wheel 92a, the clamp pieces 20a and 20b of the gripper 20 grips bottle neck portion 1a at the lower side of the support ring 5 and conveys the bottle 1 in the vertically suspended state.

Figure 16:
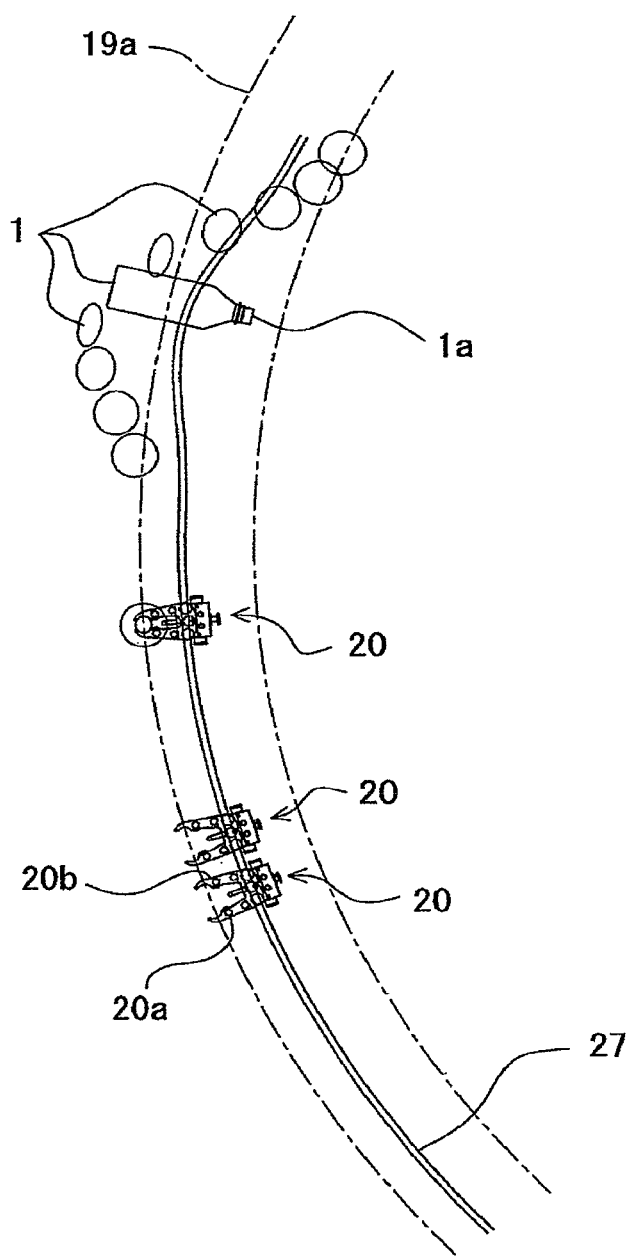
FIG. 16 is partially cutaway view showing a cam device for turning upside down the gripper shown in FIGS. 15A and 15B.

Furthermore, as shown in FIGS. 15A and 15B, the gripper 20 is provided with horizontal pivot 26 projecting in the circumferential direction of the start end wheel 19a, and the gripper 20 is held to the start end wheel 19a through the horizontal pivot 26. On the other hand, as shown in FIG. 16, another cam 27 circularly curved with the turning shaft of the start end wheel 19a being the center of the curvature is also disposed so that each of the grippers 20 contacts this cam 27. When intermediate wheel 92b is turned and the gripper 20 receiving the bottle 1 is turned, the gripper 20 is vertically inverted together with the bottle 1 with the horizontal pivot 26 being the fulcrum under the guidance of the cam 27. According to such motion, as shown in FIGS. 14A and 14B, the bottle 1 is vertically inverted with the neck portion 1a thereof being directed downward.

Figure 14B:
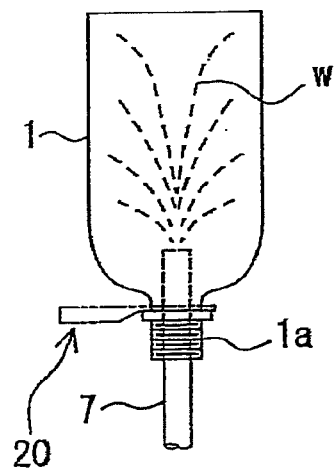
FIG. 14B is a view representing a hot water rinsing process performed by the beverage filling apparatus shown in FIG. 13.

As shown in FIG. 14A, the bottle 1 passing through the interior of the air rinse section 96 travels in the aseptic water rinse section 91 with being gripped in the vertical attitude by the gripper 28 around the start end wheel 92a, and as shown in FIG. 14B, is then inverted in its position by the gripper 20 of the intermediate wheel 92b. At this time, the hot water nozzle 93 is inserted into the bottle 1 through the bottle neck portion 1a to thereby feed the hot water "w" of the aseptic water into the bottle 1. The hot water "w" cleans the inside of the bottle 1 and then flows out of the bottle 1 from the neck portion 1*a* thereof. After the cleaning of the bottle 1 by the hot water "w", the bottle 1 is again turned to the vertically normal position by the gripper 20 of the intermediate wheel 92*b*, is received by the gripper 28 of the final end wheel 92*c*, and is then conveyed to the subsequent beverage filling section 10.

The hot water "w" is aseptic water of the temperature of about 60 to 70° C., but it may be of normal temperature.

As shown in FIG. 16, the beverage filling section 10 is connected to the aseptic water rinse section 91. The beverage filling section 10 is also entirely covered with the chamber 10*a*, and a partition wall, not shown, is disposed between this chamber 10*a* and the chamber 91*a* of the aseptic water rinse section 91. The partition wall is formed with a bottle passing hole.

A wheel row coupled with the final end wheel 92*c* as travelling means for the bottle 1 on the aseptic water rinse section side is connected, as shown in FIG. 13, to the inside of the chamber 10*a* of the beverage filling section 10.

More specifically, this wheel row includes six wheels 94*a*, 94*b*, 94*c*, 94*d*, 94*e*, 94*f*, around which a bottle travelling path is formed.

Furthermore, grippers 28 similar to those shown in FIG. 4 are arranged around the respective wheels 94*a*, 94*b*, 94*c*, 94*d*, 94*e* and 94*f*.

In the chamber 10*a* of the beverage filling section 10, the grippers 28 transfer the bottles 1 subsequently from the start end wheel 94*a* to the final end wheel 94*f* while gripping the bottle neck portions 1*a* and turning around the respective wheels 94*a*, 94*b*, 94*c*, 94*d*, 94*e* and 94*f*. According to such operation, the bottles 1 continuously travel in the beverage filling section 10 from the start end wheel 94*a* toward the final end wheel 94*f*, and during the travelling, since the gripper 28 grips the neck portion 1*a* of the bottle 1 by the paired clamp pieces 28*a* and 28*b*, the bottle 1 travels in the normally vertically suspended attitude.

The beverage filling machine is disposed in the chamber 10*a* of the bottle 1 is filled with the preliminarily sterilized beverage "a" from the nozzle 95 of the beverage filling machine. This nozzle 95 is travelled in synchronous with the bottle 1, and accordingly, a constant amount of beverage "a" fills the bottle 1 during the travelling of the bottle 1 and the nozzle 95.

Furthermore, a capper is disposed to a predetermined position around the intermediate wheel 94*e* on the downstream side of the beverage filling machine. As shown in FIG. 3O, the cap 2 is applied by the neck portion 1*a* of the bottle 1, thus sealing the bottle 1.

The bottle 1 filled with the beverage "a" and sealed by the cap 2 is then released from the gripper 28 of the final end wheel 94*f* and discharged externally from the beverage filling apparatus from an outlet of the chamber 10*a*.

Incidentally, as shown in FIG. 13, a servo-motor S3 for driving all the wheels 92*a*, 92*b*, 92*c* in the aseptic water rinse section 91 so as to be dynamically interlocked with each other is disposed in the aseptic water rinse section 91, and three servo-motors S4, S5 and S6 for driving the wheels 94*a*, 94*b*, 94*c*, 94*d*, 94*e* and 94*f* in the beverage filling section 10 so as to be dynamically interlocked in predetermined combinations thereof are disposed in the beverage filling section 10. In these servo-motors S4, S5 and S6, the servo-motor S4 drives the wheels 94*a* and 94*b* disposed on the upstream side of the intermediate wheel 94*b* for which the beverage filling machine is provided, the servo-motor S5 drives the intermediate wheel 94*c* for which the beverage filling machine is provided, and the servo-motor S6 drives the wheels 94*d*, 94*e* and 94*f* disposed downstream side of the intermediate wheel 94*c* for which the beverage filling machine is provided.

According to the arrangement mentioned above, even if the respective wheels and grippers of the inspection section 8, the air rinse section 96, the aseptic water rinse section 91 and the beverage filling section 10 have the structures different from each other, the grippers of the respective sections can be driven synchronously in accordance with the controlling of the servo-motors S1 to S6, and thus, the bottles 1 can be smoothly continuously travelled from the molding section 7 toward the beverage filling section 10.

Further, in the above second embodiment, although the molding section 7 is driven by a generally known electric motor, the wheels and the turntable of the molding section 7 may be also driven by the servo-motor.

The function or operation of the beverage filling apparatus according to the second embodiment will be described hereunder.

(1) First, the preform 6 such as shown in FIG. 3A is prepared. The preform 6 is injection-molded through the injection molding process, and thereafter, is fed into the preform supply machine 11 of the beverage filling apparatus of this embodiment.

The preform 6 is then supplied into the molding section 7 by means of conveyer 12 of the preform supply machine.

(2) The preform 6 is conveyed by the conveyer 12 in a vertically standing position as shown in FIG. 3A is received by the gripper of the start end wheel 13*a* continuously rotating in the molding section 7, and is inverted up-side-down by the gripper of the intermediate wheel 13*b*.

The preform 6 in the inverted attitude is applied to the mandrel 17 of the first turntable 14*a* from the neck portion 1*a* of the bottle 1.

The mandrel 17 applied with the preform 6 travels, as shown in FIG. 3C, while revolving, in the heating chamber 16, and then, continuously travels in the heating chamber 16, while revolving, together with the mandrel 17. Thus, the preform 6 can be uniformly heated to a temperature capable of being subjected to the blow molding treatment.

(3) The heated preform 6 is clamped by the blow molding mold 18 as shown in FIG. 3D, and air is blown through the blow nozzle 19 penetrating the mandrel 17. Thus, the bottle 1 is molded in the mold 18.

The thus molded bottle 1 is taken out of the mold 18 by opening the mold 18 together with the mandrel 17, and as shown in FIG. 3E, is conveyed in the inverted attitude toward the first turntable 14*a* through the sixth turntable 14*f*.

(4) The bottle 1 held by the mandrel 17 at the first turntable 14*a* grips by the gripper 98 of the start end wheel 19*a*, as shown in FIG. 3F, in the normally vertical attitude. In this time, the gripper 98 grips the portion of the bottle 1 above the support ring 5 of the bottle neck portion 1*a*. Subsequently, the bottle 1 is received by the gripper 28, as shown in FIG. 4, of the final end wheel 19*b*, and at this time, the gripper 28 grips the portion of the bottle 1 below the support ring 5 of the bottle neck portion 1*a* as shown in FIG. 6.

(5) The gripper 37 of the start end wheel 36*a* of the inspection section 8 grips the portion of the bottle 1 above the support ring 5 of the bottle neck portion 1*a* and receives the bottle 1. This bottle 1 is turned in a state being held by the gripper 37

During this turning motion, as shown in FIG. 3G, the shell portion of the bottle 1 is inspected by the bottle shell portion inspection means. In this inspection, the image of the bottle shell portion picked up by the camera 45 is processed by the image processing device, not shown, and it is discriminated whether any abnormality such as injury, foreign material, discoloration or like exists.

(6) The bottle 1 is transferred to the gripper 28 of the intermediate wheel 36b from the gripper 37 of the start end wheel 36a, and then, as shown in FIG. 3H and FIG. 6, is turned by the gripper 28 of the intermediate wheel 36b while being gripped at the portion below the support ring 5 of the bottle neck portion 1.

During this turning motion, as shown in FIG. 3H, the temperature of the bottle 1 is detected by the temperature sensor 46 of the temperature detecting means. In this temperature detection, if it does not reach 50° C., for example, it is judged that this bottle 1 is defective product.

(7) Subsequently, as shown in FIG. 3I, the surface condition of the support ring 5 of the bottle 1 is inspected by the support ring inspection means. In this inspection, the image of the upper face of the support ring 5 picked up by the camera 48 is processed by the image processing device, not shown, and it is discriminated whether any abnormality such as injury, foreign material, discoloration or like exists.

(8) Subsequent to the inspection of the support ring 5 of the bottle 1, as shown in FIG. 3J, the surface condition of the upper face 1d of the bottle neck portion 1a is inspected by the bottle neck portion upper face inspection means. In this inspection, the image of the upper face 1d of the bottle neck portion 1a picked up by the camera 50 is processed by the image processing device, not shown, and it is discriminated whether any abnormality such as injury, foreign material, discoloration or like exists.

(9) Subsequent to the inspection of the upper face 1d of the bottle neck portion 1a, as shown in FIG. 3K, the bottom portion of the bottle 1 is inspected. In this inspection, the image of the bottle bottom portion picked up by the camera 52 is processed by the image processing device, not shown, and it is discriminated whether any abnormality such as injury, foreign material, discoloration or like exists.

(10) The bottle 1 subjected to the above respective inspections is held by the gripper 28 shown in FIG. 8 of the final end wheel 36c of the inspection section 8. In an event that a signal representing any abnormality is generated during these various inspections, the gripper releasing mechanism is operated as shown in FIG. 9 so that the paired clamp pieces 28a and 28b of the gripper 28 are operated from the closed state shown with two-dot-chain line to the opened state shown with solid line, thus releasing the defective bottle 1.

According to such operation, the bottle 1 to which any abnormality such as injury is generated to the shell portion, the bottom portion, the upper face 1d of the bottle neck portion 1a, the support ring 5 or the like is removed from the bottle travelling path. Furthermore, the bottle 1 of a temperature such that sufficient sterilization cannot be given to the bottle 1 even if the sterilization by the hydrogen peroxide is effected in the following sterilizing process is also removed from the bottle travelling path.

On the other hand, the good bottle as non-defective product is conveyed toward the sterilization section 9 through the bottle removing section because the movable cam 53a is retained at the position shown in FIG. 9A.

(11) The bottle 1 as good product is transferred to the gripper 28 of the start end wheel 58a of the sterilization section 9 from the gripper 28 of the final end wheel 36c of the inspection section 8, and then transferred to the grippers of the downstream side wheels and continuously travelled.

When the bottle 1 as good product is travelled around the intermediate wheel 58b in the state being gripped by the gripper 28, as shown in FIG. 3L, the bottle 1 passes directly below the spray tube 59. Accordingly, the condensed mist α of the hydrogen peroxide ejected from the spray tube 59 is sprayed toward the bottle 1 to thereby sterilize the inner and outer surfaces of the bottle 1. As mentioned above, since only the bottles 1 judged as good products to which proper heat remains reach, these bottles 1 are properly sterilized by the condensed mist α of the hydrogen peroxide and then conveyed downstream side.

(12) The bottle 1 sterilized by the condensed mist α of the hydrogen peroxide is travelled around the intermediate wheel 58c in the manner of being gripped by the gripper 28, and in this time, as shown in FIG. 3M, the hydrogen gas β and the hot air γ are blown from the nozzle 64. Accordingly, the inner and outer surfaces of the bottle 1 are subjected to the air rinsing treatment to thereby remove the hydrogen peroxide adhering to the inner and outer surfaces of the bottle 1.

(13) As shown in FIG. 12, the positive pressure creating means is disposed on the way of the travelling path from the molding section 7 to the sterilization section 9 through the inspection section 8. According to the location of such positive pressure creating means, extra amounts of the condensed mist α of the hydrogen peroxide and the gas β flowing into the chamber 9a of the sterilization section 9 are exhausted outside the chamber 9a through the ducts 86 and 89. On the other hand, the cleaned air flowing into the chamber 8a of the inspection section 8 flows toward the chamber 7a of the molding section 7 and the atmosphere shutoff chamber 79 so as to prevent the contaminated air or air containing the hydrogen peroxide from flowing into the chamber 8a of the inspection section 8.

Furthermore, even if the air is sucked into the chamber 8a of the inspection section 8 from the chamber 7a of the molding section by the travelling of the bottle 1, this air is prevented from flowing into the chamber 9a of the sterilization section 9 by the exhaust from the atmosphere shutoff chamber 79, so that the inside of the sterilization section 9 can be effectively prevented from being contaminated.

(14) During the conveyance of the bottle 1 toward the downstream side of the sterilization section 9 though the inspection section 8, if any abnormality is generated on the molding section side and the wheel row on the molding section side is emergently stopped, as shown in FIG. 7, the piston rod 42a of the piston-cylinder assembly 42 is contracted so that the paired clamp pieces 37a and 37b now in closed state are opened by about 180 degrees as shown in FIG. 7. According to this operation, the interference of the gripper 28 mounted to the final end wheel 19b of the molding section 7 with the gripper 37 mounted to the start end wheel 36a of the inspection section 8 can be prevented from causing.

Furthermore, since the start end wheel 36a and the following wheel rows are continuously rotated, the bottle 1 introduced into the inspection section 8 is continuously travelled toward the downstream side. Accordingly, the normally molded bottle 1 is inspected in the inspection section 8, and the bottle 1 passing through the inspection section 8 is conveyed toward the sterilization section 9, thus preventing waste bottles 1 from generating. In addition, even if the molding section 7 stops the operation, the inspection section 8 and the following sections can be operated, so that the bottle 1 can be continuously travelled in the downstream side direction following the sterilization section 9, and hence, the excessive adhesion of the hydrogen peroxide by the stopping of the bottle 1 in the sterilization section 9 and the defective sterilization function due to the cooling of the bottle 1 can be effectively prevented. Thus, the only the good bottles 1 can be filled with the beverage.

(15) The bottle 1 blown with the condensed mist α of the hydrogen peroxide in the sterilization section 9 enters the air rinse section 96 and is subjected to the air rinsing treatment around the wheel 58c as shown in FIG. 14A. Accordingly, the excessive amount of the hydrogen peroxide adhering to the bottle 1 can be removed therefrom.

(16) The bottle 1 subjected to the air rinsing treatment is conveyed into the aseptic water rinse section 91 from the gripper 28 of the final end wheel 58e of the air rinse section 96 and then travelled around the wheels 92a, 92b and 92c in the aseptic water rinse section 91 from the upstream side toward the downstream side. The bottle 1 is then inverted up-side-down by the gripper 20 of the intermediate wheel 92b, and as shown in FIG. 14B, the interior of the bottle 1 is cleaned with the aseptic hot water "w". Thus, the excessive hydrogen peroxide adhering to the inner surface of the bottle 1 can be removed.

In the case where the air in the air rinse section does not include the gas β of the hydrogen peroxide, although such aseptic water rinsing treatment may be eliminated, even in such case, the aseptic water rinsing treatment may be performed as occasion demands. The bottle 1 after the cleaning is returned to the normal vertical position with the bottle neck portion 1a being directed upward by the inverting movement of the gripper 20.

(17) The bottle 1 subjected to the aseptic water rinsing treatment is conveyed to the beverage filling section 10, and at the time of travelling around the wheel 94c with being gripped by the gripper 28, a predetermined amount of the beverage "a" is fed from the nozzle 95 of the beverage filling machine, as shown in FIG. 3N.

(18) The bottle 1 filled up with the beverage "a" travels around the wheel 94e with the neck portion 1a thereof being gripped by the gripper 28, and during the travelling, the cap 2 is applied to the neck portion 1a by the capper as shown in FIG. 3O. According to this operation, the bottle 1 is sealed as beverage package, which is then conveyed outward the beverage filling apparatus.

Further, in the embodiment of FIG. 13, it may be possible to eliminate the air rinse section 96 and directly connect the aseptic water rinse section 91 to the sterilization section 9. In such arrangement, the bottle 1 sterilized in the sterilization section 9 is immediately sent to the aseptic water rinse section 91 so as to be subjected to the hot-water rinsing treatment of the heated aseptic water. According to this operation, although the sterilization by the hydrogen peroxide in the sterilization section 9 is relatively difficult, aspergillus spore such as ascomycontina relatively weak to heat may be sterilized by the aseptic hot water. Thus, beverage which is liable to be corrupted by the aspergillus spore can fill the bottle, which is then stored.

Third Embodiment 3

Figure 20A:
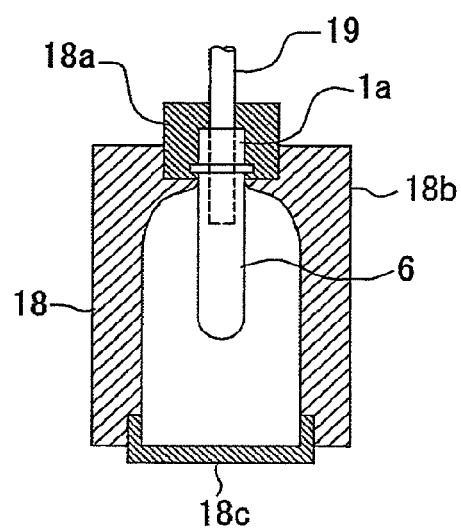
FIG. 20A is a view representing a blow molding process in a beverage filling method relating to a third embodiment of the present invention.
Figure 20B:
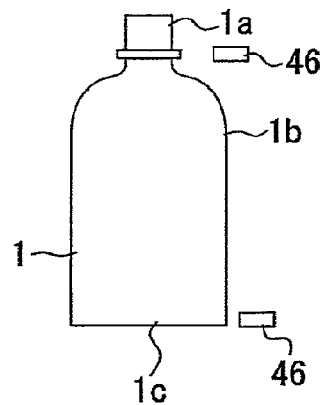
FIG. 20B is a view representing a bottle temperature inspection process.

In this third embodiment, a container or vessel to be sterilized is a bottle 1 shown in FIG. 20B, which is obtained by blow-forming the preform 6 formed of PET shown in FIG. 20A. The preform 6 has a bottomed tubular shape having a mouth portion 1a as like as the bottle 1.

This container is sterilized in a sequence shown in FIG. 20.

First, a preform as shown in FIG. 20A is prepared. The preform 6 is heated so that an entire temperature of the bottle 1 increased to a uniform temperature range suitable for the molding of the preform 6, and thereafter, as shown in FIG. 20A, the preform 6 is fed into the mold 18 so as to be molded as a bottle 1.

A blow-molding (injection) machine is provided with the mold 18 surrounding the preform 6 and the blow nozzle 19 for blowing gas. The bottle 1 is formed in the mold 18 by blowing gas such as air from the blow nozzle 19 into the preform 6 of which temperature is increased to the suitable temperature range in the mold 18. Thereafter, the mold 18 is opened and the bottle 1 is taken out of the mold 18.

In this blow forming process, the temperature of the mold 18 is maintained at substantially constant temperature, which is a temperature of the bottle 1 at the time of supplying the condensed mist α of the hydrogen peroxide into the bottle 1 and is appropriately set in accordance with substance or material of the bottle 1 or shape to be desired, and this temperature is, for example, 60 to 80° C.

As shown in FIG. 20A, the mold 18 is composed of a mold upper portion 18a corresponding to the mouth portion 1a of the bottle 1, a mold central portion 18b corresponding to the shell portion 1b of the bottle 1 and a mold bottom portion 18c corresponding to the bottom portion 1c of the bottle 1, and these mold portions are splittable and are set so as to have temperatures different from each other. For example, the temperature of the mold upper portion 18a corresponding to the mouth portion 1a of the bottle 1 may be set to a temperature lower than those of the mold central portion 18b and mold bottom portion 18c. Since the mouth portion 1a of the bottle 1 has already been formed to the preform 6, if the mouth portion 1a is excessively heated, the mouth portion 1a may be deformed. Therefore, such deformation of the mouth portion 1a can be prevented by setting the temperature of the mold upper portion 18a contacting the mouth portion 1a to be lower than those of the other portions, the deformation of the mouth portion 1a may be effectively prevented.

The molding process of the bottle 1 shown in FIG. 20A is performed synchronously with the travelling of the mold 18 of the blow molding machine, the blow nozzle 19 and the preform 6. However, it may be possible to mold the bottle 1 from the preform 6 at a fixed position by setting the blow forming machine to the fixed position.

The thus molded bottle 1 is maintained at a predetermined temperature by the remaining heat at the molding process by the mold 18, and during the following travelling at a predetermined speed, as shown in FIG. 20B, the surface temperature is detected by the temperature sensors 46, 46. This temperature is a preliminarily heating temperature for suitably sterilizing the bottle 1, and it is hence desirable to be more than 50° C. for effectively achieving the desired sterilizing effect by the hydrogen peroxide in the following process.

As the temperature sensors 46, 46, although an infrared ray thermometer may be utilized, for example, other thermometers may be also utilized. These temperature sensors 46, 46 are arranged so as to oppose to the support ring of the mouth portion 1a of the bottle 1 and the bottom portion 1c thereof as shown in FIG. 20B.

In a case where either one of the temperatures of these two portions of the bottle 1 detected by the two temperature sensors 46 and 46 does not reach the predetermined temperature, such bottle 1 is removed as defective product. Such defective bottle 1 having a temperature not reaching the predetermined temperature may be considered not to be sufficiently sterilized even if the bottle 1 is sterilized by the hydrogen peroxide in the following process. On the other hand, the bottle 1 of which temperatures of two portions reach the predetermined temperatures will be considered to be sufficiently sterilized when the bottle 1 is sterilized by the hydrogen peroxide in the following process. Such bottle 1 is continuously travelled as good product toward the sterilization section so as to be subjected to the sterilization process as shown in FIG. 20C.

Further, although the two portions of the bottle 1 mentioned above opposing to the temperature sensors 46, 46 are portions liable to cause cold spots, the number of the temperature sensors to be located is not limited to two and may be increased or decreased in accordance with the shape and size of the bottle 1, and a kind of the mold, or like. For example, only one temperature sensor 46 may be located to the position opposing to the bottle bottom portion 1c to which cold spot will be liable to be caused rather than to the portion of the support ring.

Figure 20C:
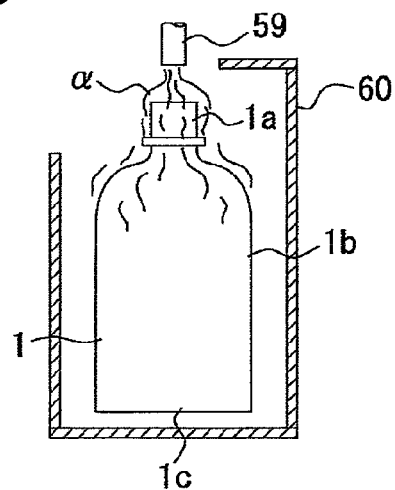
FIG. 20C is a view representing a bottle sterilization process by means of condensed mist of hydrogen peroxide.

After the molding process, the bottle 1 maintaining the preheating temperature is travelled at the predetermined speed, and as shown in FIG. 20C, during this travelling, the condensed mist α of the hydrogen peroxide as a sterilizing agent is blown to thereby sterilize the bottle 1. The bottle 1 of the temperature not reaching the preheating temperature is removed before the sterilization process shown in FIG. 20C, so that only the bottle 1 maintaining the predetermined preheating temperature is subjected to the sterilization process.

Further, the bottle 1 may be supplied for the sterilization process as shown in FIG. 20C by preparing a preliminarily molded bottle 1 without connecting the molding process of the bottle 1 to the sterilization process. In such case, it is necessary to convey the bottle 1 for the sterilization process after heating the bottle 1 to the preheating temperature while blowing hot air to the travelling bottle 1. The surface temperature of the bottle 1 is measured also by the manner mentioned with reference to FIG. 20B, and the bottle 1 to which temperature does not reach the predetermined temperature is removed.

The condensed mist α of the hydrogen peroxide is generated by gasifying the hydrogen peroxide and then condensing such gasified hydrogen peroxide such as by a mist generating device 61 shown in FIG. 10.

The bottle 1 is travelled with its mouth portion 1a being directed upward, and the spray tube 59 is arranged at the predetermined position above the travelling path, with the opening of the spray tube 59 being directed to the mouth portion 1a of the bottle 1. The condensed mist α of the hydrogen peroxide is continuously blown out towards the mouth portion 1a of the bottle 1 conveyed along the travelling path from the opening of the spray tube 59, and the sprayed condensed mist α of the hydrogen peroxide flows into the bottle 1 through the mouth portion 1a thereof and sterilizes the inner surface of the bottle 1 and also flows out of the bottle 1 to thereby sterilize the outer surface of the bottle 1.

The condensed mist α of the hydrogen peroxide sprayed from the spray tube 59 adheres by, preferably, an amount of 30 μL/bottle to 150 μL/bottle, and more preferably, an amount of 50 μL/bottle to 100 μL/bottle.

As mentioned above, it is desirable that the surface temperature of the bottle 1 at the supply time of the condensed mist α of the hydrogen peroxide is more than 50° C. that is the preheating temperature, and for this purpose, the spray tube 59 is arranged to the position at which the bottle surface temperature can be maintained at a temperature more than 50° C. The surface temperature of the bottle at this time will be determined on the basis of the heat capacity of the bottle 1, the atmospheric condition around the bottle 1, the heat amount applied by the mold 18 and so on. In this embodiment, the bottle travelling speed from the blow molding machine to the spray tube 59, the mold temperature at the bottle molding process and so on are set so that the bottle surface temperature becomes more than 50° C. at the time of supplying the condensed mist α of the hydrogen peroxide.

Further, the bottle surface temperature at the time of supplying the condensed mist α of the hydrogen peroxide is appropriately set in accordance with substance and shape of the bottle 1, kind of the sterilizing agent, and so on so as to suitably sterilize the bottle 1. It may be not necessary to set the temperature of the entire bottle surface to be more than 50° C. For example, in a case where the temperatures of the upper portion 18a of the mold 18 is lowered more than those of the central portion 18b and lower portion 18c of the mold 18 at the time of molding the bottle 1, the temperature of the mouth portion 1a of the bottle 1 may become less than 50° C. In such case, according to the present embodiment, since the condensed mist α of high density of the hydrogen peroxide is supplied to the mouth portion 1a of the bottle 1, the mouth portion 1a can be suitably sterilized.

In the sterilization process shown in FIG. 20C, it may be desired that the bottle travelling path is surrounded by a tunnel 60, and by surrounding the travelling path by the tunnel 60, the condensed mist α of the hydrogen peroxide easily adheres to the outer surface of the bottle 1, thus improving the sterilizing effect to the bottle outer surface.

Figure 20D:
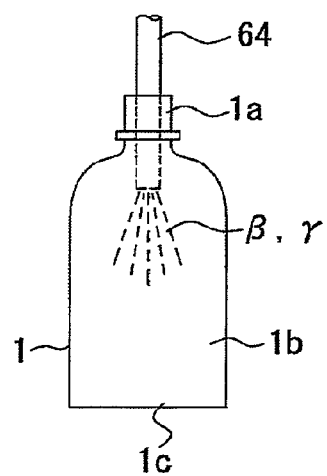
FIG. 20D is a view representing a bottle air-rinsing process.

The bottle 1 of which inner and outer surfaces are sterilized by the condensed mist α of the hydrogen peroxide is further travelled toward the air rinse section so as to be subjected to the air rinsing treatment as shown in FIG. 20D.

In this air rinsing treatment, the nozzle 64 following the travelling of the bottle 1 is disposed. The nozzle 64 is inserted into the bottle 1 through its mouth portion 1a while travelling together with the bottle 1 at the same speed. Of course, it is possible for the nozzle 64 to be arranged so as to be directed to the mouth portion 1a of the bottle 1 without inserting thereinto.

The hydrogen peroxide gas β conveyed by the sterilized and heated hot air is blown into the bottle 1 through the nozzle 64. This hydrogen peroxide gas β is generated by the air rinse device shown in FIG. 17 and then supplied to the bottle 1.

Figure 20E:
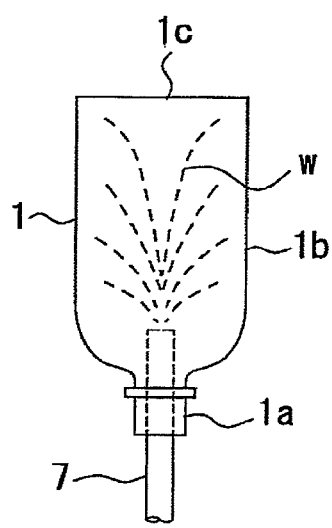
FIG. 20E is a view representing a bottle hot water rinsing process.

The bottle 1 effected with the air rinsing treatment is travelled for receiving the cleaning process shown in FIG. 20E, but the cleaning process may be performed as occasion demands.

In this cleaning process, the bottle 1 is travelled in an inverted upside-down-state, and the nozzle 7 for cleaning is inserted into the mouth portion 1a directed downward, and the heated aseptic water "w" is injected into the bottle 1 through the nozzle 7. In this manner, the hydrogen peroxide remaining inside the bottle 1 is washed out.

Although it is desirable that the aseptic water "w" is supplied for the cleaning process by being heated to about 60 to 80° C., the aseptic water of normal temperature may be supplied as occasion demands. The aseptic water supplying time is appropriately set in accordance with the capacity or shape of the bottle 1 to, for example, 1 to 10 seconds.

After the cleaning of the bottle 1 by the aseptic water "w", the bottle 1 is again inverted to the state of the mouth portion 1a being directed upward. Thereafter, the cleaned bottle 1 is filled with inner content, and after the filling of the inner content, the bottle 1 is sealed by applying the cap, not shown, to the mouth portion 1a, thus forming a sealed aseptic package.

Effects attained by the container sterilization method of the present invention will be compared with effects attained by the conventional sterilization method as in the following Table 2.

TABLE 2

| No. | $H_2O_2$ mist adhering amount (μL/bottle) | $H_2O_2$ adding amount in air (gas density) (mg/L) | Log reduction | Number of bacteria adhering on inner surface of preform | | | $H_2O_2$ using amount (mL/min) | Judgment | | |
|---|---|---|---|---|---|---|---|---|---|---|
| | | | | $10^3$ | $10^4$ | $10^5$ | | | Sterilization performance | Total |
| A1 | 50 | 0.0 | <3.4 | ●●● | ●●● | ●●● | 170 | ○ | X | △ |
| A2 | 100 | 0.0 | 6.0 | ○○○ | ○○○ | ○○● | 340 | X | ○ | △ |
| A3 | 150 | 0.0 | >6.0 | ○○○ | ○○○ | ○○○ | 510 | X | ◉ | △ |
| B1 | 50 | 3.3 | 6 | ○○○ | ○○○ | ○○● | 230 | ○ | ○ | ○ |
| B2 | 50 | 5 | >6.0 | ○○○ | ○○○ | ○○○ | 280 | ○ | ◉ | ○ |

In the column "No" in the above Table 2, A1, A2, A3, B1, B2 denotes bottle sample numbers, in which A1, A2 and A3 correspond to the conventional sterilization method, and B1 and B2 correspond to the third embodiment of the present invention mentioned above.

In the Table 2, the column "$H_2O_2$ Mist Adhering Amount" represents the hydrogen peroxide mist adhering to the inner surface of the bottle.

The column of "$H_2O_2$ Adding Amount In Air" represents the gas density of the hydrogen peroxide gas added in hot air of the air rinse process.

The column "Log Reduction" represents LRV (Logarithmic Reduction Value) as to *B. subtilis* spore.

The column of "Bacteria Amount Adhering to Preform Inner Surface" represents the numbers of bacteria adhering to the inner surfaces of the preforms before the molding of the respective bottles A1, A2, A3, B1, B2, and symbol [○] shows good sterilization effect and [●] shows insufficient sterilization effect.

In the column of "Judgment", the term "H2O2 Using Amount" shows the using amount of the hydrogen peroxide and shows the fact whether this using amount is appropriate or not, in which symbol [○] shows appropriate using amount and [X] shows excessive using amount.

In the column of "Sterilization Performance", [◉] shows the sterilizing effect (LRV) being more than 6, [○] shows LRV being 6, and [X] LVR being less than 6. In the column of "Total", [○] shows that both the using amount and the sterilizing performance are good, and [△] shows that either one of the using amount and the sterilization performance is defective.

As is apparent from the Table 2, according to the conventional method, the sterilization effect of LRV=6 can be obtained only by using large amount of the hydrogen peroxide of 340 mL/min. to 510 mL/min. However, according to the method of the present invention, the sterilization effect LRV=6, which is the same as that in the conventional method, can be obtained by using the hydrogen peroxide only of 230 mL/min. to 260 mL/min. That is, according to the present invention, substantially the same sterilization effect as that attained in the conventional method can be obtained only by reducing the using amount of the hydraulic peroxide to ½~⅓ of the conventional method.

Figure 21:
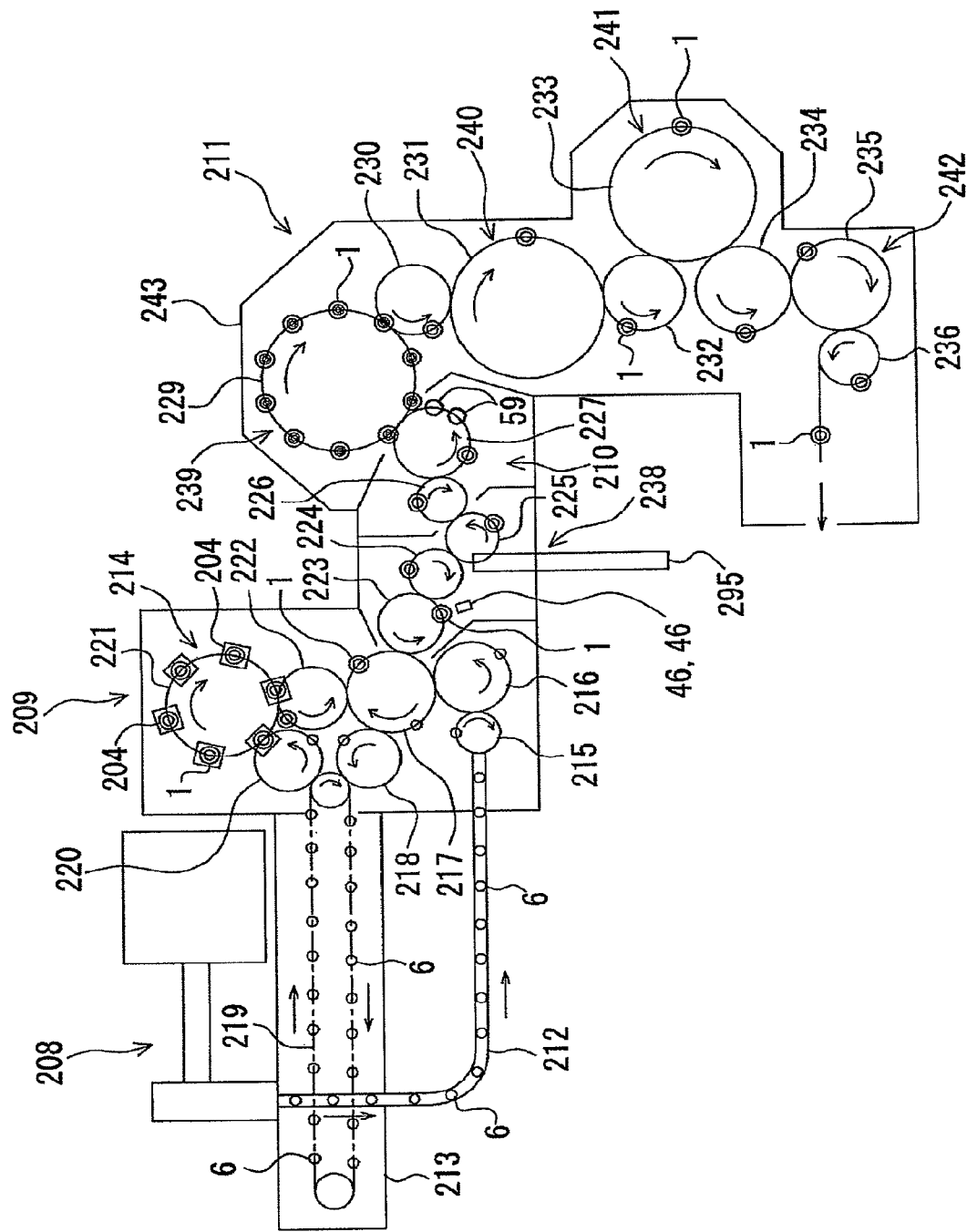
FIG. 21 is a schematic plan view representing a beverage filling apparatus according to a third embodiment of the present invention.

The device for performing the method of the third embodiment has a structure shown in FIG. 21.

As shown in FIG. 21, this sterilization device is provided with a preform supply machine 208 for continuously supplying the bottomed preforms 6 (shown in FIG. 20A) each having a mouth portion 1a at a predetermined interval, a blow molding machine 209, a bottle sterilizing machine 210 as sterilizing means for sterilizing the bottle 1 by contacting the hydrogen peroxide condensed mist α to the molded bottle 1, and a filling machine 211 as filling means for cleaning the sterilized bottle 1 and filling the bottle 1 with content such as beverage and then sealing the bottle 1.

A bottle conveying path is formed by predetermined conveying means along a line between the preform supplying machine 208 and the filling machine 211, and on the conveying path, grippers 28 (FIG. 17) and other members for holding and conveying the preforms 6 and the bottles 1 are disposed.

The preform supplying machine 208 is provided with a preform conveyer 212 for subsequently supplying the preforms 6 to the blow molding machine 209 at predetermined interval. The preforms 6 are fed to the blow molding machine 209 through the preform conveyer 212.

The blow molding machine 209 a heating section 213 for heating the preform 6 conveyed by the preform conveyer 212 and a molding section 214 for heating and forming the heated preform 6 into a bottle 1.

Inside the blow molding machine 209, there is conveying means for receiving the preform 6 at the final end portion of the preform conveyer 212 and molding the preform into the bottle 1, and then conveying the bottle 1 to the succeeding bottle sterilizing machine 210, and on this conveyer path, the heating section 213, the molding section 214 and so on are disposed.

The conveying means is provided with a first row of wheels 215, 216, 217, 218 for conveying the preform 6 from the final end portion of the preform conveyer 212 to the heating section 213, a conveyer 219 for conveying the preform 6 within the heating section 213, and a second row of wheels 220, 221, 222, 217 for receiving the heated preform 6 from the conveyer 219 and feeding the preform to the molding section 214, in which the preform 6 is molded into the bottle 1, and then feeding the molded bottle 1 to the subsequent sterilizing machine 210. The wheel 217 may be commonly utilized between the first wheel row of wheels 215, 216, 217, 218 and the second wheel row of wheels 220, 221, 222, 217.

The preform 6 is fed into the blow molding machine 209 by the preform conveyer 212, and thereafter, is transferred to the conveyer 219 through the first wheel row of wheels 215, 216, 217, 218, and according to the travelling of the conveyer 219, the preform 6 is reciprocally moved in the seating section 213. A heater, now shown, is provided for the wall portion of the heating section 213, so as to heat the preform 6 conveyed by the conveyer 219. The preform 6 heated in the heating section 213 is received by the second wheel row of the wheels 220, 221, 222, 217 and then is transferred to the molding section 214.

The molding section 214 is provided with a mold 18 (FIG. 20A) for molding the heated preform 6 into the bottle 1 and a blow nozzle 19 (FIG. 20A) blowing gas into the heated preform 6.

The mold 18 is composed of, as shown in FIG. 20A, the mold upper portion 18a for molding the mouth portion 1a of the bottle 1, the mold central portion 18b for molding the shell portion 1b of the bottle 1, and the mold bottom portion 18c for molding the bottom portion 1c of the bottle 1, and the bottle 1 is formed in the mold 18 by blowing gas such as air into the preform through the blow nozzle 19. The mold 18 molds the bottle 1 from the preform 6 while being moved together with the preform 6 in the circumferential direction of the wheel 221.

The preform 6 is heated by the heating section 213 of the preform supplying machine 208 and cooled at the time of being molded into the bottle 1 by the mold 18 of the blow molding machine 209. The bottle 1, however, discharged from the mold 18 is travelled around the wheels 222 and 217 while keeping the preliminary molding temperature by the remaining heat at the molding time.

A temperature inspection device 238 is provided to a portion between the molding section 214 of the blow molding machine 209 and the subsequent bottle sterilizing machine 210, and a wheel row including wheels 223, 224, 225 is disposed within the temperature inspection device 238.

The temperature sensors 46, 46 are arranged to the outer peripheral portion of the wheel 223 contacting the wheel 217 as shown in FIG. 20B. A discharge conveyer 295 such as air conveying device is connected to the downstream side wheel 225 contacting the wheel 223 through the intermediate wheel 224. The bottle 1, which is judged not to reach the preliminary molding temperature by the temperature sensors 46, 46 is discharged outside the conveying path from the discharge conveyer 295. On the other hand, the bottle 1, which is judged to reach the preliminary molding temperature by the temperature sensors 46, 46 is successively travelled along the conveying path and fed to the subsequent bottle sterilizing machine 210.

The bottle sterilizing machine 210 is further provided with a third wheel row including wheels 226, 227 as means for conveying the bottle 1 subjected to the temperature inspection as mentioned above and the spray tube 59 as condensed mist supply means for supplying the hydrogen peroxide condensed mist α as the sterilizing agent to the bottle 1.

One or more than one spray tubes 59 may be disposed, and are fixed to predetermined positions along the peripheries of the predetermined wheels in the third wheel row of wheels 226 and 227. In the illustrated embodiment, although the spray tube 59 is disposed around the final end wheel 227, the spray tube 59 may be disposed around the other wheel.

The condensed mist α is generated by condensing hydrogen peroxide sprayed and heated by the mist generating device 61 shown in FIG. 10. The bottle 1 is conveyed around the wheel 227 with the mouth portion 1a being directed downward, and lower end of the spray tube 59 is opened toward the mouth portion 1a of the bottle 1. The hydrogen peroxide condensed mist α is continuously brown out toward the mouth portion 1a of the bottle 1 from the lower end opening of the spray tube 59. The hydrogen peroxide condensed mist α is flown into the bottle 1 through the mouth portion 1a of the travelling bottle 1 and sterilizes the inner surface of the bottle 1, and the other hydrogen peroxide condensed mist α also sterilizes the outer surface of the bottle 1.

The amount of the hydrogen peroxide condensed mist α discharged from the spray tube 59 and adhering to the bottle 1 is that mentioned above.

The bottle 1 to which the hydrogen peroxide condensed mist α is supplied through the spray tube 59 is conveyed to the succeeding filling machine 211 after the appropriate sterilization process.

The filling machine 211 includes fourth wheel row including wheels 229, 230, 231, 232, 234, 235, 236 as means for conveying the bottles 1 sterilized in the sterilizing machine 210. An air rinse section 239 for performing the air-rinsing treatment to the bottle 1 to which the hydrogen peroxide condensed mist α was supplied, a cleaning section 240 for cleaning the bottle 1 after the air-rinsing treatment, a filler 241 for filling the cleaned bottle 1 with inner content, and a capper 242 for applying a cap, not shown, to the bottle 1 after being filled with the content and then sealing the bottle 1 are disposed in the described order along the fourth wheel row.

The air rinse section 239 is provided with the nozzle 64 (FIG. 20D) around the wheel 229. The sterilized hot air γ and the hydrogen peroxide gas β are blown into the bottle 1 through the nozzle 64 (see FIG. 2D).

A plurality of nozzles 64 are arranged so as to correspond to the bottles 1 (1:1) conveyed around the wheel 229, and as shown in FIG. 17, the nozzles 64 are attached to the periphery of the wheel 229 and moved integrally with the bottle 1 in the circumferential direction of the wheel 229.

In the illustration of FIG. 17, although the nozzles 64 serve to blow the sterilized hot air γ and the hydrogen peroxide gas β into the bottles 1 from the position outside the bottles 1, the respective nozzles 64 may be disposed so as to be vertically movable and inserted into the bottles 1, as shown in FIG. 20D, when the hot air γ and the hydrogen peroxide gas β are blown into the bottles 1.

The hot air γ and the hydrogen peroxide gas β from the nozzles 64 may be generated by the manner mentioned with reference to FIG. 17.

As mentioned hereinabove, by blowing the sterilized hot air γ and the hydrogen peroxide gas β into the bottle 1 to thereby perform the air rinsing treatment, the bottle 1 can be heated from its inside, and the sterilization effect by the hydrogen peroxide condensed mist α and the hydrogen peroxide gas β can be enhanced. In addition, a portion such as bottom portion 1c of the bottle 1, which may be insufficiently sterilized by the hydrogen peroxide condensed mist α supplied from the spray tube 59, can be also surely sterilized by the hydrogen peroxide gas β contained in the hot air γ.

Further, the time period for blowing the hot air γ and the hydrogen peroxide gas β will be determined in such a manner that the hydrogen peroxide condensed mist α floating inside the bottle 1 can be completely discharged and the defective sterilization by the condensed mist α can be compensated for, and for example, for 20 seconds.

The cleaning section 240 is provided with an inverting mechanism, not shown, disposed around the wheel 231 for vertically inverting the bottle 1 and a nozzle 7 (FIG. 20E) for supplying the heated aseptic water to the bottle 1. A plurality of nozzles 7 are arranged around the wheel 231 so as to correspond to the bottles 1 (1:1) conveyed by the wheel 231, and the nozzles 7 are moved integrally with the bottles 1, respectively. The cleaning section 240 is disposed as occasion demands, and hence, it may be eliminated in location.

Further, since conventional filler and capper are utilized as the filler 241 and the capper 242, the descriptions thereof will be eliminated herein.

Incidentally, this sterilization device is surrounded by a chamber 243, and the interior of this chamber 243 is sectioned into an aseptic zone, non-aseptic zone, and a gray zone positioned intermediately between the aseptic zone and non-aseptic zone. The preform supplying machine 208, the molding machine 209 and the temperature inspection section 238 are arranged in the non-aseptic zone, the bottle sterilizing machine 210 is arranged in the gray zone, and the filling machine 211 is arranged in the aseptic zone, respectively.

Hereunder, the operation of the sterilization device will be explained with reference to FIGS. 1 and 2.

First, the preform 6 is fed into the blow molding machine 209 by the preform conveyer 212. The preform 6 conveyed into the blow molding machine 209 is conveyed toward the heating section 213 through the first wheel row of the wheels 216, 217, 218.

The preform 6 in the heating section 213 is conveyed by the conveyer 219, and during the conveyance, is heated such that the entire temperature of the preform 6 increases to the temperature range suitable for the molding.

The preform 6 heated in the heating section 213 is conveyed by the second wheel row of the wheels 220, 221 toward the molding section 214, in which during the conveyance, the preform 6 is molded by the mold 18 and the blow nozzle 19 which are moved together with the preform 6 (refer to FIG. 20A).

In the molding section 214 of the sterilization device, the preform 6 is molded by the mold 18, which is maintained at a predetermined temperature. This predetermined temperature is appropriately set in accordance with the bottle temperature, bottle substance, bottle shape at the time of supplying the hydrogen peroxide condensed mist α to the bottle 1 mentioned hereinafter, for example, to 60 to 80° C.

The molded bottle 1 is transferred from the second wheel row of wheels 221, 222, 217 to the 223, 224, 225 of the temperature inspection section 238, and during the travelling around the wheel 223, it is judged whether the surface temperature of the bottle 1 reaches the predetermined preliminarily heating temperature or not, and in the case where the temperature of the bottle 1 does not reach the predetermined preliminarily heating temperature, such bottle 1 is discharged as defective product from the wheel 225 by the discharge conveyer 295 outside the conveying path, and on the other hand, in the case where the temperature of the bottle 1 reaches the predetermined preliminarily heating temperature, such bottle 1 is continuously travelled around the wheel 226 as good product.

The bottle 1 judged to be good product is transferred to the third wheel row of the wheels 226, 227, by which the bottle 1 is travelled into the sterilizing machine 210.

The predetermined amount of the hydrogen peroxide condensed mist α is supplied through the spray tube 59 into the bottle 1 in the bottle sterilizing machine (FIG. 20B), and during the conveyance of the bottle 1, the hydrogen peroxide condensed mist α is continuously supplied. For this purpose, the hydrogen peroxide condensed mist α is blown for several seconds to the inner and outer surfaces of the bottle 1 during the passing of the bottle 1 under the spray tube 59 by the rotation of the wheel. Since the surface temperature of the bottle 1 reaching the bottle sterilizing machine 210 is maintained more than 50° C., the bottle 1 can be appropriately sterilized by the hydrogen peroxide condensed mist α.

The sterilized bottle 1 is transferred from the third wheel row of the wheels 226, 227 to the fourth wheel row of the wheels 229, 230, 231, 232, 233, 234, 235, 236 and then travelled in the filling machine 211 by the fourth row of wheels.

In the filling machine 211, the bottle 1 is first conveyed to the air rinse section 239, in which the nozzle 64 is inserted into each of the bottles 1 around the wheel 229, and the hot air γ and the hydrogen peroxide gas β are supplied into the bottle 1 to thereby perform the air rinsing treatment (FIG. 20D).

After the air rinsing treatment, the bottle 1 is conveyed to the cleaning section 240, in which the bottle is vertically inverted around the wheel 231 by the inverting mechanism, not shown, and the nozzle 7 is inserted into the bottle 1 from the downwardly directed mouth portion 1a thereof to thereby supply the heated aseptic water "w" into the bottle 1 through the nozzle 7 (FIG. 20E). In this manner, the hydrogen peroxide remaining in the bottle 1 is washed out. Although the aseptic water "w" has a temperature of 60 to 70° C., it may be normal temperature.

After the cleaning by the aseptic water "w", the bottle 1 is again vertically inverted so that the mouth portion 1a thereof is directed upward.

This cleaning section 240 may be eliminated as occasion demands.

Thereafter, the bottle 1 is filled with the content such as beverage, which was subjected to the sterilization treatment, by the filler 241. The bottle 1 with the inner content is applied with the cap, not shown, by the capper 242 for sealing, and then discharged from an outlet of the chamber 243. As mentioned above, since the filler 241 and the capper 242 are known ones, explanations of the method of filling the bottle with the content and the method of sealing the bottle will be omitted herein.

Fourth Embodiment 4

As shown in FIG. 22, a bottle sterilization apparatus of this fourth embodiment is provided with a preliminarily heating device 296 in place of the preform supply machine 208 and the blow molding machine 209 of the sterilization apparatus of the third embodiment.

A wheel row including wheels 276, 277, 278 forming a bottle conveying path is disposed to a position corresponding to the preliminarily heating device 296.

In this wheel row, an air conveying device 279, for example, is connected to the most upstream side wheel 276 and the molded bottles 1 are subsequently supplied. The bottles 1 are conveyed around the wheels 276, 277 and 278 by being gripped by grippers similar to those 28 shown in FIG. 4.

Box members 280, each in form of tunnel through which the bottles pass, are provided around the wheels 276, 277 and 278, respectively. Hot air is supplied to each box member 280 from a hot air supply device of the structure similar to that shown in FIG. 17. The hot air blown into the box member 280 is directed toward the bottle 1 passing through the box member 280 to thereby preliminarily heat the bottle 1. According to this preliminarily heating, the bottle temperature increases to a temperature more than 50° C.

Thereafter, although the bottles 1 are conveyed toward the bottle sterilizing machine 219 to be subjected to the sterilization treatment, before this conveyance, the bottles 1 are inspected in the temperature inspection section 238 whether the surface temperature of the bottle 1 reaches the predetermined preliminarily heating temperature.

The temperature inspection section 238 has a structure similar to that of the third embodiment and is provided with the wheel row of wheels 223, 224, 225, 226 interposed between the wheel 278 of the preliminarily heating device 296 and the wheel 227 of the bottle sterilizing machine 210. The bottles 1 preliminarily heated by the preliminarily heating device 296 are travelled around the wheel 223, and during this travelling, it is discriminated whether the surface temperature of the bottle 1 reaches the predetermined preliminarily heated temperature. The bottle 1 of which surface temperature does not reach the predetermined preliminarily heated temperature is discharged outside the conveying path by the discharge conveyer 295 from the wheel 225 as defective product. On the contrary, the bottle 1 of which surface temperature reaches the predetermined preliminarily heated temperature is successively travelled as a good product around the wheel 226.

Further, the location of such temperature inspection section 238 is optional and may be omitted on demand.

The bottle 1 subjected to the temperature inspection is conveyed toward the bottle sterilizing machine 210. Since the bottle 1 is preliminarily heated, the sterilizing effect by the hydrogen peroxide condensed mist α supplied in the sterilizing machine 210 can be improved.

The structures of the sterilization apparatus downstream side of this bottle sterilizing machine 210 are substantially the same as those in the sterilization apparatus of the third embodiment, so that the details thereof will be omitted herein.

Fifth Embodiment 5

Figure 23:
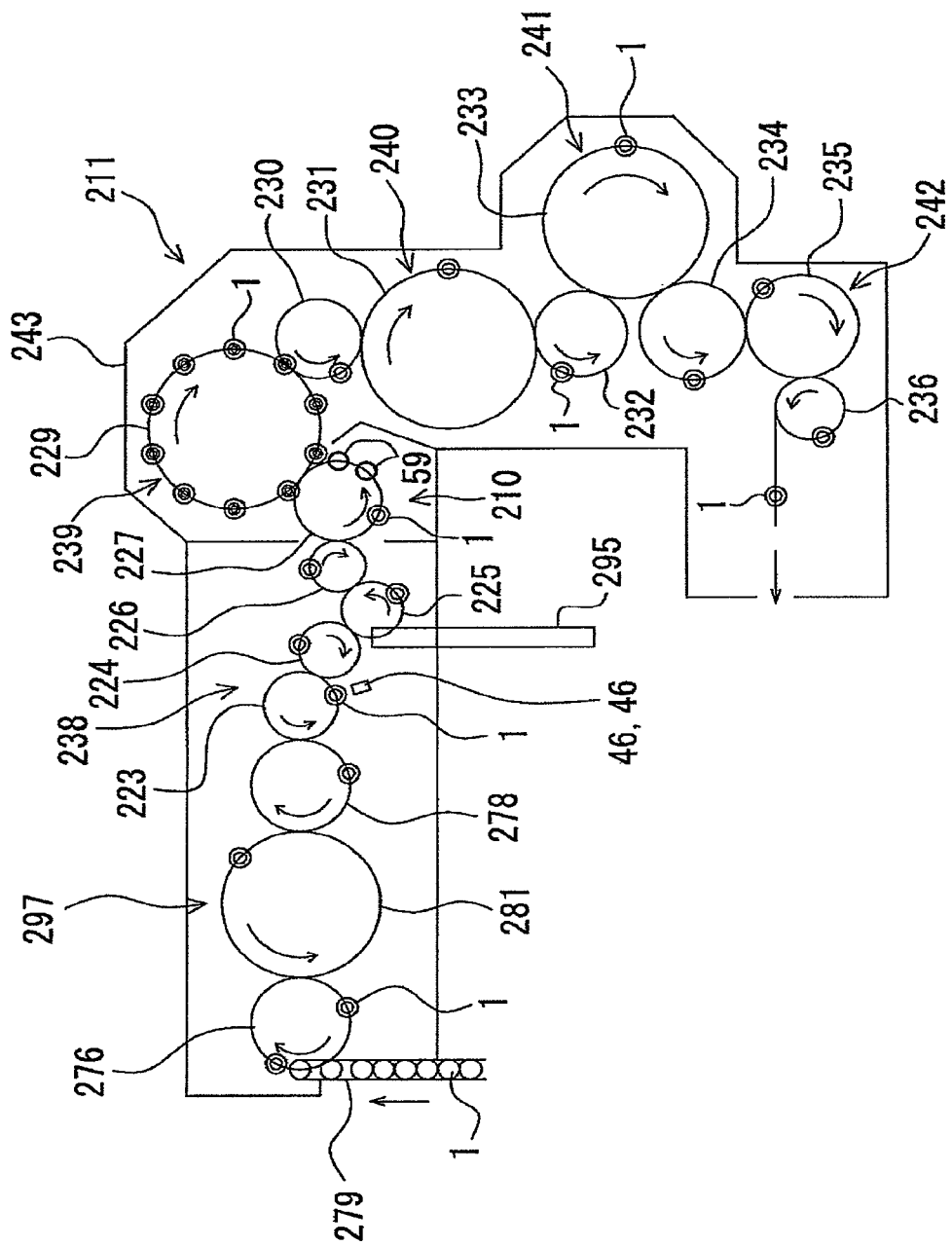
FIG. 23 is a schematic plan view representing a beverage filling apparatus according to a fifth embodiment of the present invention.

As shown in FIG. 23, a bottle sterilization apparatus of this fifth embodiment is provided with a preliminarily heating device 297 having a structure different from that of the preliminarily heating device 296 of the fourth embodiment mentioned above.

That is, another wheel 281 is provided in place of the wheel 277 of the fourth embodiment, and a hot air supplying device of the structure similar to that shown in FIG. 11 is arranged around this wheel 281.

The bottle temperature increases to a temperature more than 50° C. by this hot air supplying device.

Thereafter, although the bottles 1 are conveyed toward the bottle sterilizing machine 210 to be subjected to the sterilization treatment, before this conveyance, the bottles 1 are inspected in the temperature inspection section 238 whether the surface temperature of the bottle 1 reaches the predetermined preliminarily heating temperature.

The temperature inspection section 238 has a structure similar to that of the third embodiment and is provided with the wheel row of wheels 223, 224, 225, 226 interposed between the wheel 278 of the preliminarily heating device 296 and the wheel 227 of the bottle sterilizing machine 210. The bottles 1 preliminarily heated by the preliminarily heating device 296 are travelled around the wheel 223, and during this travelling, it is discriminated whether the surface temperature of the bottle 1 reaches the predetermined preliminarily heated temperature. The bottle 1 of which surface temperature does not reach the predetermined preliminarily heated temperature is discharged outside the conveying path by the discharge conveyer 295 from the wheel 225 as defective product. On the contrary, the bottle 1 of which surface temperature reaches the predetermined preliminarily heated temperature is successively travelled as a good product around the wheel 226.

Further, the location of such temperature inspection section 238 is optional and may be omitted on demand.

The bottle 1 subjected to the temperature inspection is conveyed toward the bottle sterilizing machine 210. Since the bottle 1 is preliminarily heated, the sterilizing effect by the hydrogen peroxide condensed mist α supplied in the sterilizing machine 210 can be improved.

The structures of the sterilization apparatus downstream side of this bottle sterilizing machine 210 are substantially the same as those in the sterilization apparatus of the third embodiment, so that the details thereof will be omitted herein.

Furthermore, it is to be noted that the present invention is not limited to the described embodiments and many other changes and modifications may be made.

For example, the container to which the beverage filling apparatus of the present invention is applicable is not limited to a PET bottle, and the present invention may be applied to various resin containers. In addition, as the beverage, liquids containing particular material, agglomerate material or like, or high viscosity material other than simple liquid may fill the container. Furthermore, the bottle may be molded by direct blow molding method, injection molding method without being limited to the injection blow molding method.

Still furthermore, the cleaning of the bottle by the aseptic water is not limited to a method performed while flowing the aseptic water. The conveying means for conveying the bottles is not limited to the wheel conveying device mentioned above, and various conveying devices capable of conveying the bottles at a predetermined conveying speed in accordance with the bottle molding order, such as air conveying device, belt conveying device, bucket conveying device and the like may be utilized.

Furthermore, the sterilizing method and sterilizing devices utilized in the beverage filling method and beverage filling apparatus according to the present invention may take the following modes or examples.

(1) Mode 1

This mode 1 for the sterilization method includes: removing a container having temperature not reaching predetermined temperature by performing the container temperature inspection while travelling the container; blowing the hydrogen peroxide condensed mist toward the mouth portion of the container through the spray tube disposed at the predetermined position while travelling the container having the predetermined temperature; and blowing the hydrogen peroxide gas into the container through the nozzle while moving the nozzle so as to follow the mouth portion of the container.

According to this mode 1, only the containers of which temperature reaches a predetermined temperature can be travelled toward the sterilization section to be subjected to the suitable sterilization treatment by the hydrogen peroxide, and accordingly, it becomes possible to prevent the content from filling the container which is insufficiently sterilized. Furthermore, since the hydrogen peroxide gas is supplied after the supplying of the hydrogen peroxide condensed mist, the container can be suitably sterilized without increasing the flow rate and consuming amount of the hydrogen peroxide and the hydrogen peroxide condensed mist even if the travelling speed of the container is increased for enhancing the productivity of the aseptic packages.

(2) Mode 2

This mode 2 includes a container sterilization method in which preliminarily heating is performed by remaining heat at the molding time of the container in the container sterilization method of the mode 1.

According to this mode 2, the container can be preheated without additionally preparing a heat source for preliminary heat, and therefore, the heat energy becomes effectively usable.

(3) Mode 3

This mode 3 includes a container sterilization method in which the hydrogen peroxide gas is a gas obtained by heating and gasifying the hydrogen peroxide condensed mist by hot air in the container sterilization method of the mode 1 or mode 2.

According to this mode 3, the hydrogen peroxide gas having a suitable density can be supplied to the container without being condensed, and therefore, the hydrogen peroxide can be prevented from falling down into the container and the container can be sufficiently sterilized.

(4) Mode 4

This mode 4 includes a container sterilization method in which the container is cleaned by the aseptic water after the blowing of the hydrogen peroxide gas into the container in the container sterilization method described in any one the mode 1, mode 2 or mode 3.

According to this mode 4, the hydrogen peroxide used for the sterilization can be effectively removed from the container.

(5) Mode 5

This mode 5 includes the container sterilization apparatus provided with conveying means for conveying the container along the predetermined path, and including; preliminarily heating means for preliminarily heating the container travelling along the conveying path to a predetermined temperature; a temperature sensor for inspecting whether a temperature of the preliminarily heated bottle reaches the predetermined temperature; removing means for removing the container of which temperature does not reach the predetermined temperature from the conveying path; a spray tube for blowing hydrogen peroxide condensed mist from a predetermined position toward a mouth portion of the container of which temperature reaches the predetermined temperature; and a nozzle through which the hydrogen peroxide gas is blown into the container while following the container travelling along the conveying path, the above means and members being arranged along the conveying path.

According to this mode 5, only the container of which temperature reaches the predetermined temperature is travelled toward the sterilization section in which the container can be appropriately sterilized by the hydrogen peroxide, and accordingly, it becomes possible to prevent the content from filling the container which is insufficiently sterilized. Furthermore, since the hydrogen peroxide gas is supplied after the supplying of the hydrogen peroxide condensed mist, the container can be suitably sterilized without increasing the flow rate and consuming amount of the hydrogen peroxide and the hydrogen peroxide condensed mist (M) even if the travelling speed of the container is increased for enhancing the productivity of the aseptic packages.

(6) Mode 6

This mode 6 includes the container sterilization apparatus provided with the container molding machine disposed upstream side of the spray tube of the conveying path commonly serves as the preliminarily heating means in the container sterilization apparatus described in the above mode 5.

According to this mode 6, the preliminarily hating utilizes the remaining heat in the container molding process, and accordingly, the energy can be effectively utilized without separately preparing a heat source for the preliminary heating.

(7) Mode 7

This mode 7 includes the container sterilization apparatus provided with the container preliminarily hating device on the upstream side of the spray tube in the container sterilization apparatus described in the above mode 5.

According to this mode 7, the preliminary heating of the container can be surely performed.

(8) Mode 8

This mode 8 includes the container sterilization apparatus, in which the hydrogen peroxide gas is generated by heating the hydrogen peroxide condensed mist with hot air, in the container sterilization apparatus described in any one of the above modes 5 to 7.

According to this mode 8, the hydrogen peroxide gas with proper density can be supplied to the container without being condensed, and therefore, the container can be suitably sterilized while preventing the hydrogen peroxide from dropping in the container.

(9) Mode 9

This mode 9 includes the container sterilization apparatus provided with the cleaning means for cleaning the interior of the container by the aseptic water on the downstream side of the nozzle for blowing the hydrogen peroxide gas, in the container sterilization apparatus described in any one of the above modes 5 to 8.

According to this mode 9, the hydrogen peroxide utilized for the sterilization can be effectively removed from the container.

The invention claimed is:

1. A beverage filling method comprising:
   forming a bottle from a heated preform through a blow molding process;
   blowing hydrogen peroxide mist or gas to the bottle within a time in which heat applied to the preform remains for a sterilization process;
   filling the bottle with beverage as a filling process; and then
   sealing the bottle,
   wherein forming the bottle from the heated preform, the blowing the hydrogen peroxide mist or gas, the filling the bottle with the beverage and the sealing the bottle are performed while continuously travelling the bottle;
   wherein during the sterilization process:
      the bottle is travelled with a neck portion directed upward, a lower end of a spray tube is opened toward the neck portion of the bottle;
      a part of the hydrogen peroxide mist or gas supplied into the spray tube is continuously blown toward the neck portion through a nozzle hole formed to the lower end of the spray tube so that the blown hydrogen peroxide mist or gas flows into the bottle from the neck portion of the bottle and sterilizes the inner surface of the bottle,
      a remaining part of the hydrogen peroxide mist or gas simultaneously flows outside of the bottle so as to sterilize an outer surface of the bottle,
   wherein an air-rinse process for air-rinsing, with aseptic air, is further performed on the bottle sterilized in the sterilization process between the sterilization process and the filling process,
   wherein the bottle blown with condensed mist of the hydrogen peroxide from the spray tube at the sterilization process reaches inside the air rinse process within 0.1 to 5.0 seconds, wherein a chamber for covering a portion from the sterilization process to the filling process is provided;

wherein an atmosphere shutoff chamber is disposed between a chamber of an inspection process and the chamber of the sterilization process, wherein partition walls are disposed, respectively between the chamber of the inspection process and the atmosphere shutoff chamber and between the atmosphere shutoff chamber and the chamber of the sterilization process, wherein a second air exhaust, as air exhaust means, is coupled with the atmosphere shutoff chamber, and wherein an air exhaust means is coupled to a portion adjacent to the atmosphere shutoff chamber in the chamber which covers the sterilization process, this air exhaust means being connected to the second air exhaust, thereby the air with hydrogen peroxide mist or hydrogen peroxide gas is exhausted out of the chamber by the air exhaust means.

2. The beverage filling method according to claim 1, wherein the bottle is subjected to an air-rinse treatment after the blowing of the hydrogen peroxide mist or gas into the bottle, and the bottle is then filled with the beverage and sealed.

3. The beverage filling method according to claim 2, wherein the bottle is subjected to a rinse treatment with aseptic water after the air-rinse treatment, and the bottle is then filled with the beverage and sealed.

4. The beverage filling method according to claim 3, wherein a traveling path is provided so that the molded bottle is continuously travelled in to a section at which the sealing of the bottle is performed, the travelling path being formed from a wheel row around which grippers are arranged, and the bottle is transferred from an upstream side wheel to a downstream side wheel in a state that a neck portion of the bottle is grasped by the gripper around the respective wheels while revolving.

5. The beverage filling method according to claim 2, wherein a traveling path is provided so that the molded bottle is continuously travelled in to a section at which the sealing of the bottle is performed, the travelling path being formed from a wheel row around which grippers are arranged, and the bottle is transferred from an upstream side wheel to a downstream side wheel in a state that a neck portion of the bottle is grasped by the gripper around the respective wheels while revolving.

6. The beverage filling method according to claim 1, wherein the bottle is subjected to a rinse treatment with aseptic water after the air-rinse treatment with A aseptic air containing hydrogen peroxide gas, and the bottle is then filled with the beverage and sealed.

7. The beverage filling method according to claim 6, wherein a traveling path is provided so that the molded bottle is continuously travelled in to a section at which the sealing of the bottle is performed, the travelling path being formed from a wheel row around which grippers are arranged, and the bottle is transferred from an upstream side wheel to a downstream side wheel in a state that a neck portion of the bottle is grasped by the gripper around the respective wheels while revolving.

8. The beverage filling method according to claim 1, wherein the bottle is subjected to a rinse treatment with heated aseptic water after the blowing of the hydrogen peroxide mist or gas into the bottle, and the battle is then filled with the beverage and sealed.

9. The beverage filling method according to claim 8, wherein a traveling path is provided so that the molded bottle is continuously travelled in to a section at which the sealing of the bottle is performed, the travelling path being formed from a wheel row around which grippers are arranged, and the bottle is transferred from an upstream side wheel to a downstream side wheel in a state that a neck portion of the bottle is grasped by the gripper around the respective wheels while revolving.

10. The beverage filling method according to claim 1, wherein a traveling path is provided so that the molded bottle is continuously travelled in to a section at which the sealing of the bottle is performed, the travelling path being formed from a wheel row around which grippers are arranged, and the bottle is transferred from an upstream side wheel to a downstream side wheel in a state that a neck portion of the bottle is grasped by the gripper around the respective wheels while revolving.

11. The beverage filling method according to claim 1, wherein while the sterilization process, the bottle travels in a tunnel, thereby mist or gas of the hydrogen peroxide is uniformly supplied to the outer surface of the bottle.

12. The beverage filling apparatus according to claim 1, wherein an aseptic water rinse section for rinsing, with heated aseptic water, the bottle sterilized in the sterilization section is further disposed between the sterilization section and the filling section.

\* \* \* \* \*